US011098348B2

(12) United States Patent
Morin et al.

(10) Patent No.: US 11,098,348 B2
(45) Date of Patent: Aug. 24, 2021

(54) NANOPORE DETECTION OF TARGET POLYNUCLEOTIDES FROM SAMPLE BACKGROUND

(71) Applicant: Ontera Inc., Santa Cruz, CA (US)

(72) Inventors: Trevor J. Morin, Santa Cruz, CA (US); Tyler Shropshire, Santa Cruz, CA (US); William B. Dunbar, Santa Cruz, CA (US); Daniel A. Heller, Santa Cruz, CA (US); Hongyun Wang, Santa Cruz, CA (US)

(73) Assignee: Ontera Inc., Santa Cruz, CA (US)

( * ) Notice: Subject to any disclaimer, the term of this patent is extended or adjusted under 35 U.S.C. 154(b) by 0 days.

(21) Appl. No.: 15/547,434

(22) PCT Filed: Feb. 2, 2016

(86) PCT No.: PCT/US2016/016233
§ 371 (c)(1),
(2) Date: Jul. 28, 2017

(87) PCT Pub. No.: WO2016/126746
PCT Pub. Date: Aug. 11, 2016

(65) Prior Publication Data
US 2018/0023115 A1    Jan. 25, 2018

Related U.S. Application Data

(60) Provisional application No. 62/111,075, filed on Feb. 2, 2015.

(51) Int. Cl.
*C12Q 1/686*    (2018.01)
*C12Q 1/6816*   (2018.01)
(Continued)

(52) U.S. Cl.
CPC .......... *C12Q 1/686* (2013.01); *C12Q 1/6806* (2013.01); *C12Q 1/6816* (2013.01); *C12Q 1/6848* (2013.01); *C12Q 1/6851* (2013.01)

(58) Field of Classification Search
CPC .... C12Q 1/686; C12Q 1/6806; C12Q 1/6816; C12Q 1/6848; C12Q 1/6851; C12Q 1/6844; C12Q 2565/631; C12Q 33/48721
See application file for complete search history.

(56) References Cited

U.S. PATENT DOCUMENTS 6,952,651 B2   10/2005  Su
8,845,880 B2    9/2014  Davis et al.
(Continued)

FOREIGN PATENT DOCUMENTS

CN    1694967      11/2005
CN    103827320    5/2014
(Continued)

OTHER PUBLICATIONS

Hyre et al. Cooperative hydrogen bond interactions in the streptavidin-biotin system. Protein Science 15:459-467. (Year: 2006).*
(Continued)

*Primary Examiner* — Samuel C Woolwine
(74) *Attorney, Agent, or Firm* — Fenwick & West LLP

(57) ABSTRACT

Disclosed herein are methods and compositions for detection of target polynucleotides in a mixed sample by amplification of the target polynucleotide and detection in a nanopore device.

59 Claims, 28 Drawing Sheets
Specification includes a Sequence Listing.

(51) Int. Cl.
*C12Q 1/6806* (2018.01)
*C12Q 1/6848* (2018.01)
*C12Q 1/6851* (2018.01)

(56) References Cited

U.S. PATENT DOCUMENTS

| | | | |
|---|---|---|---|
| 8,889,348 B2 | 11/2014 | Ju | |
| 8,926,813 B2 | 1/2015 | Oliver | |
| 9,719,980 B2 | 8/2017 | Oliver | |
| 2002/0197618 A1 | 12/2002 | Sampson | |
| 2003/0143604 A1* | 7/2003 | Storhoff | C12Q 1/6844 435/6.11 |
| 2003/0232346 A1 | 12/2003 | Su | |
| 2004/0022764 A1 | 2/2004 | Polansky | |
| 2004/0023207 A1* | 2/2004 | Polansky | A61K 31/00 435/5 |
| 2005/0186576 A1 | 8/2005 | Chan et al. | |
| 2007/0048745 A1 | 3/2007 | Joyce et al. | |
| 2007/0190543 A1* | 8/2007 | Livak | C12Q 1/6816 435/6.19 |
| 2008/0268440 A1* | 10/2008 | Liu | B01J 19/0046 435/6.12 |
| 2008/0280369 A1 | 11/2008 | Bazan et al. | |
| 2010/0130402 A1* | 5/2010 | Pfuetzner | G01N 33/74 514/5.9 |
| 2010/0267011 A1 | 10/2010 | Kim et al. | |
| 2012/0160681 A1 | 6/2012 | Davis et al. | |
| 2012/0160688 A1 | 6/2012 | Davis et al. | |
| 2012/0316075 A1 | 12/2012 | Buzby et al. | |
| 2013/0040827 A1* | 2/2013 | Macevicz | C12Q 1/6869 506/2 |
| 2013/0233709 A1 | 9/2013 | Dunbar et al. | |
| 2014/0057339 A1* | 2/2014 | Esfandyarpour | G01N 27/327 435/287.2 |
| 2014/0329225 A1 | 11/2014 | Morin | |
| 2015/0011402 A1 | 1/2015 | Davis et al. | |
| 2015/0119259 A1* | 4/2015 | Ju | C12Q 1/6869 506/2 |
| 2015/0276709 A1* | 10/2015 | O'Halloran | B01L 3/502761 506/6 |
| 2018/0080072 A1* | 3/2018 | Li | G01N 33/48721 |
| 2018/0155768 A1 | 6/2018 | Cohen et al. | |

FOREIGN PATENT DOCUMENTS

| | | |
|---|---|---|
| EA | 009302 B1 | 12/2007 |
| JP | H05273209 | 10/1993 |
| JP | H11346798 | 12/1999 |
| JP | 2013506418 | 2/2013 |
| JP | 2014145771 | 8/2014 |
| JP | 2014-531196 A | 11/2014 |
| JP | 2017-515131 A | 6/2017 |
| KR | 20070016566 | 2/2007 |
| KR | 20100031498 | 3/2010 |
| KR | 20120000520 | 1/2012 |
| WO | WO 2007/117832 A2 | 10/2007 |
| WO | WO 2013/012881 | 1/2013 |
| WO | WO-2013014451 A1 * | 1/2013 ........... C12Q 1/6869 |
| WO | WO 2014/024041 A1 | 2/2014 |
| WO | WO 2014/059046 A1 | 4/2014 |
| WO | WO 2014/144217 A1 | 9/2014 |
| WO | WO 2018/093976 A1 | 5/2018 |

OTHER PUBLICATIONS

Sumida-Yasumoto et al. (1977) Synthesis of phiX174 viral DNA in vitro depends on phiX replicative form DNA. PNAS 74(10):4195-4199. (Year: 1977).*

Weber et al. Structural Origins of High-Affinity Biotin Binding to Streptavidin. Science 243:85-88. (Year: 1989).*

Yang et al. Detection of Panton-Valentine Leukocidin DNA from methicillin-resistant *Staphylococcus aureus* by resistive pulse sensing and loop-mediated isothermal amplification with gold nanoparticles. Analytics Chimica Acta 782:46-53. (Year: 2013).*

Räty et al. Enhanced Gene Delivery by Avidin-Displaying Baculovirus. Molecular Therapy 9(2):282-291. (Year: 2004).*

Examination Report No. 1 for Australian Patent Application No. AU 2016215453, dated Jul. 27, 2017, 3 Pages.

Office Action for Canadian Patent Application No. CA 2,973,753, dated Aug. 22, 2017, 3 Pages.

Office Action for Canadian Patent Application No. CA 2,973,753, dated Jul. 28, 2017, 3 Pages.

Office Action for Israeli Patent Application No. IL 253272, dated Nov. 22, 2017, 4 Pages (With Concise Explanation of Relevance).

Carlsen, A.T., et al., "Selective detection and quantification of modified DNA with solid-state nanopores," Nano Lett., Oct. 8, 2014, vol. 14, No. 10, pp. 5488-5492.

Kim, Y.-R., et al., "Nanopore sensor for fast label-free detection of short double-stranded DNAs," Biosensors and Bioelectronics, 2007, vol. 22, pp. 2926-2931.

Maglia, G., et al., "Analysis of single nucleic acid molecules with protein nanopores," Methods Enzymol., 2010, vol. 475, pp. 591-623.

Morin, T.J., et al., "Nanopore-based target sequence detection," PLOS One, Dec. 31, 2015, pp. 1-21.

Gu, Li-Gun, et al., "Detection of miRNAs with a nanopore single-molecule counter," Expert Rev Mol Diagn., vol. 12, No. 6, pp. 573-584, Jul. 2012.

Patent Cooperation Treaty, International Search Report and Written Opinion of the International Searching Authority, International Patent Application No. PCT/US2016/016233, dated May 6, 2016, 18 Pages.

Japan Patent Office, Office Action, Japanese Application No. 2018-230605, dated Jan. 15, 2020, 18 pages.

Russian Patent Office, Office Action, Russian Application No. 2017127990, dated Dec. 18, 2019, 6 pages.

Office Action for Japanese Patent Application No. 2017-540801, dated Dec. 25, 2017, 10 Pages (With English Translation).

Office Action for Korean Patent Application No. 10-2017-7024505, dated Jan. 16, 2018, 21 Pages (With English Translation).

Briggs, K., et al., "Automated Fabrication of 2-nm Solid-State Nanopores for Nucleic Acid Analysis," Small May 28, 2014, vol. 10, No. 10, pp. 2077-2086.

* cited by examiner

NANOPORE DETECTION OF TARGET POLYNUCLEOTIDES FROM SAMPLE BACKGROUND

CROSS REFERENCE TO RELATED APPLICATIONS

This application is a 35 U.S.C. 371 national stage filing of International Application No. PCT/US2016/016233, filed on Feb. 2, 2016, which claims the benefit of U.S. Provisional Patent Application No. 62/111,075, filed Feb. 2, 2015, the disclosure of which are incorporated herein by reference.

SEQUENCE LISTING

The instant application contains a Sequence Listing which has been submitted electronically in ASCII format and is hereby incorporated by reference in its entirety. Said ASCII copy, created on Mar. 2, 2016, is named 33066PCT_CRF_sequencelisting.txt and is 1,216 bytes in size.

BACKGROUND

Nucleic acid testing, which detects specific nucleic acid sequences or portions of an organism's genome and other biochemical machinery, has far reaching utility, including pathogen detection, genetic mutation analysis, disease screening, and transgene screening. One method of nucleic acid testing is to amplify a section of DNA to generate a plurality of amplicons (i.e. DNA target clones) to obtain information about the presence and/or quantity of a nucleic acid target. This can be used to determine, e.g. whether an organism is deemed to be present (e.g. virus), a gene is mutated, or whether a gene is expressed. Common nucleic acid testing methods rely on optical detection of amplified DNA. This can limit the portability of a device when point-of-care testing is desired. Furthermore, optical methods of detection often add instrumentation cost and complexity. Emerging technologies are ameliorating these concerns by using electrochemical sensing or purely electrical sensing, much simpler chemistry free methods of detection. Unfortunately, high fabrication cost and low yield of devices hinders these technologies from becoming commercially viable. What is needed therefore are methods, devices, and compositions for robust detection of target polynucleotide sequences that are fast, simple, and accurate, and do not require expensive or time-consuming optical or chemical detection.

SUMMARY

Various aspects disclosed herein may fulfill one or more of the above-mentioned needs. The systems and methods described herein each have several aspects, no single one of which is solely responsible for its desirable attributes. Without limiting the scope of this disclosure as expressed by the claims that follow, the more prominent features will now be discussed briefly. After considering this discussion, and particularly after reading the section entitled "Detailed Description," one will understand how the sample features described herein provide for improved systems and methods.

In some embodiments, provided herein are methods, compositions, and devices for electrical detection of the presence or absence of a target molecule or condition in a sample.

In some embodiments, provided herein is a method for detecting the presence or absence of a target polynucleotide sequence suspected to be present in a sample, the method comprising: providing a set of primers, wherein at least one of said primers is hybridizable to a polynucleotide comprising said target polynucleotide sequence, and wherein at least one of said primers is modified to comprise a conjugation site capable of specifically binding to a payload molecule; performing an amplification reaction on said sample, wherein said sample comprises said primer set and reagents for amplification, such that an amplicon comprising said target polynucleotide sequence generated by said amplification reaction will comprise said conjugation site; binding said payload molecule to said conjugation site; loading said sample into a device comprising a nanopore, wherein said nanopore separates an interior space of the device into two volumes, and configuring the device to pass the nucleic acid through one or more pores, wherein the device comprises a sensor for each pore that is configured to identify objects passing through the nanopore; and detecting the presence or absence of said target polynucleotide sequence in said sample by determining whether the target polynucleotide bound to the payload molecule passed through the nanopore using data from said sensor.

In some embodiments, the sample is loaded into said device before said amplification. In some embodiments, the sample is loaded into said device after said amplification. In some embodiments, the payload molecule is bound to said conjugation site of said amplicon after said amplification. In some embodiments, the payload molecule is bound to said conjugation site of said primer before said amplification.

In some embodiments, the sample does not undergo a purification step between said amplification and said detection in a nanopore. In some embodiments, the sample is loaded into said nanopore device at a dilution of at least 1:20000, 1:10000, 1:5000, 1:2000, 1:1000, 1:500, 1:200, 1:100, 1:50, 1:20, 1:10, 1:5, 1:2, 1:1.5, 1:1.2, 1:1.1 or 1:1.05. In some embodiments, the sample is loaded into said nanopore device without dilution. In some embodiments, the sample comprises non-target polynucleotides and amplification reaction reagents. In some embodiments, the nanopore is at least 5 nm, 10 nm, 20 nm, 30 nm, 40 nm, or 50 nm in diameter.

In some embodiments, the amplification reaction is selected from the group consisting of: polymerase chain reaction (PCR), reverse transcription PCR, ligation mediated PCR, loop mediated amplification (LAMP), isothermal amplification, strand displacement amplification (SDA), multiple displacement amplification, strand displacement amplification, helicase dependent amplification, nicking enzyme amplification reaction, or recombinant polymerase amplification. In some embodiments, the amplification reaction is performed in the interior space of the device.

In some embodiments, the target polynucleotide comprises double-stranded deoxyribonucleic acid (dsDNA), single-stranded DNA (ssDNA), peptide nucleic acid (PNA), single-stranded ribonucleic acid (ssRNA), DNA/RNA hybrid, or double-stranded ribonucleic acid (dsRNA). In some embodiments, the target polynucleotide is a naturally-occurring polynucleotide. In some embodiments, the target polynucleotide is an artificially synthesized polynucleotide. In some embodiments, the target polynucleotide is a recombinant polynucleotide.

In some embodiments, the payload molecule is selected from the group consisting of: a dendrimer, double stranded DNA, single stranded DNA, a DNA aptamer, a fluorophore, a protein, an antibody, a polypeptide, a nanobead, a nanorod, a nanotube, nanoparticle, fullerene, a PEG molecule, a liposome, or a cholesterol-DNA hybrid.

In some embodiments, the payload molecule comprises an electrical charge. In some embodiments, the charged payload molecule is selected form the group consisting of: a peptide, an amino acid, a charged nanoparticle, a synthetic molecule, a nucleotide, a polynucleotide, a metal, or an ion. In some embodiments, the sensitivity or specificity of detection of the presence of absence of the target polynucleotide is increased when said target polynucleotide is bound to said charged payload molecule as compared to unbound target polynucleotide.

In some embodiments, the sensitivity or specificity of detection of the presence or absence of the target polynucleotide is increased when said target polynucleotide is bound to said payload molecule as compared to unbound target polynucleotide.

In some embodiments, the sensor comprises an electrode pair configured to apply a voltage differential between the two volumes and to measure current flow through the nanopore separating the two volumes, generating a current event signature. In some embodiments, the current event signature generated when the payload-bound target polynucleotide passes through the nanopore is distinguishable from the current event signature of background molecules by its mean depth, maximum depth, duration, number of depth levels, area of depth and duration, or noise level.

In some embodiments, the conjugation site and the payload molecule are bound via a covalent bond. In some embodiments, the covalent bond is formed by click chemistry. In some embodiments, the click chemistry is copper catalyzed. In some embodiments, the click chemistry is copper free. In some embodiments, the conjugation site and the payload molecule are bound via a non-covalent bond. In some embodiments, the non-covalent bond is a hydrogen bond, an ionic bond, a van der Waals interaction, a hydrophobic interaction, a polar bond, a cation-pi interaction, a planar stacking interaction, or a metallic bond. In some embodiments, the conjugation site is located at the 3' or the 5' end of the said primer. In some embodiments, the conjugation site is located at the 3' or the 5' end of the said amplicon.

In some embodiments, the conjugation site comprises a chemical group, a reactive group, a small molecule, or a peptide. In some embodiments, the small molecule comprises biotin. In some embodiments, the reactive group comprises dibenzocyclooctyl (DBCO) or azide. In some embodiments, two or more payload molecules are bound to said amplicon. In some embodiments, the device comprises at least two nanopores in series, and wherein said amplicon bound to said payload molecule is simultaneously in said at least two nanopores during translocation.

Also provided herein is a method for detecting the presence or absence of a target polynucleotide sequence suspected to be present in a sample, the method comprising: providing a set of primers, wherein at least one of said primers is hybridizable to a polynucleotide comprising said target polynucleotide sequence, and wherein at least one of said primers is bound to a payload molecule; performing an amplification reaction on said sample, wherein said sample comprises said primer set and reagents for amplification, such that an amplicon comprising said target polynucleotide sequence generated by said amplification reaction will be bound to said payload molecule; loading said sample into a device comprising a nanopore, wherein said nanopore separates an interior space of the device into two volumes, and configuring the device to pass the nucleic acid through one or more pores, wherein the device comprises a sensor for each pore that is configured to identify objects passing through the nanopore; and detecting the presence or absence of said target polynucleotide sequence in said sample by determining whether the target polynucleotide bound to the payload molecule passed through the nanopore using data from said sensor.

In some embodiments, the sample is loaded into said device before said amplification. In some embodiments, the sample is loaded into said device after said amplification. In some embodiments, the sample does not undergo a purification step between said amplification and said detection in a nanopore.

In some embodiments, the sample is loaded into said nanopore device at a dilution of 1:10000, 1:1000, 1:500, 1:200, 1:100, 1:50, 1:20, 1:10, 1:5, 1:2, 1:1.5, 1:1.2, 1:1.1 or 1:1.05. In some embodiments, the sample is loaded into said nanopore device without dilution. some embodiments, the sample comprises non-target polynucleotides and amplification reaction reagents. In some embodiments, the nanopore is at least 5 nm, 10 nm, 20 nm, 30 nm, 40 nm, or 50 nm in diameter.

In some embodiments, the amplification reaction is selected from the group consisting of: polymerase chain reaction (PCR), reverse transcription PCR, ligation mediated PCR, loop mediated amplification (LAMP), isothermal amplification, strand displacement amplification (SDA), multiple displacement amplification, strand displacement amplification, helicase dependent amplification, nicking enzyme amplification reaction, or recombinant polymerase amplification. In some embodiments, the amplification reaction is performed in the interior space of the device.

In some embodiments, the target polynucleotide comprises double-stranded deoxyribonucleic acid (dsDNA), single-stranded DNA (ssDNA), peptide nucleic acid (PNA), single-stranded ribonucleic acid (ssRNA), DNA/RNA hybrid, or double-stranded ribonucleic acid (dsRNA). In some embodiments, the target polynucleotide is a naturally-occurring polynucleotide. In some embodiments, the target polynucleotide is an artificially synthesized polynucleotide. In some embodiments, the target polynucleotide is a recombinant polynucleotide.

In some embodiments, the payload molecule is selected from the group consisting of: a dendrimer, double stranded DNA, single stranded DNA, a DNA aptamer, a fluorophore, a protein, an antibody, a polypeptide, a nanobead, a nanorod, a nanotube, nanoparticle, fullerene, a PEG molecule, a liposome, or a cholesterol-DNA hybrid.

In some embodiments, the payload molecule comprises an ionic charge. In some embodiments, the charged payload molecule is selected form the group consisting of: a peptide, an amino acid, a charged nanoparticle, a synthetic molecule, a nucleotide, a polynucleotide, a metal, or an ion. In some embodiments, the sensitivity or specificity of detection of the presence or absence of the target polynucleotide is increased when said target polynucleotide is bound to said charged payload molecule as compared to unbound target polynucleotide.

In some embodiments, the sensitivity or specificity of detection of the presence of absence of the target polynucleotide is increased when said target polynucleotide is bound to said payload molecule as compared to unbound target polynucleotide.

In some embodiments, the sensor comprises an electrode pair configured to apply a voltage differential between the two volumes and to measure current flow through the nanopore separating the two volumes, generating a current event signature. In some embodiments, the current event signature generated when the payload-bound target polynucleotide passes through the nanopore is distinguishable from the current event signature of background molecules by its mean depth, maximum depth, duration, number of depth levels, area of depth and duration, or noise level.

In some embodiments, the primer and the payload molecule are bound via a covalent bond. In some embodiments, the primer and the payload molecule are bound via a non-covalent bond. In some embodiments, the payload molecule is bound at the 3' or the 5' end of the said primer.

In some embodiments, two or more payload molecules are bound to said primer. some embodiments, the amplicon and the payload molecule are bound via a covalent bond. In some embodiments, the amplicon and the payload molecule are bound via a non-covalent bond. In some embodiments, two or more payload molecules are bound to said amplicon.

In some embodiments, the device comprises at least two nanopores in series, and wherein said amplicon bound to said payload molecule is simultaneously in said at least two nanopores during translocation.

Also provided herein is a method for detecting the presence or absence of a target polynucleotide sequence suspected to be present in a sample, the method comprising: providing a set of primers, wherein at least one of said primers is hybridizable to a polynucleotide comprising said target polynucleotide sequence; performing an amplification reaction on said sample, wherein said sample comprises said primer set and reagents for amplification, such that an amplicon comprising said target polynucleotide sequence generated by said amplification reaction is at least 100 base pairs in length; loading said sample into a device comprising a nanopore, wherein said nanopore separates an interior space of the device into two volumes, and configuring the device to pass the nucleic acid through one or more pores, wherein the device comprises a sensor for each pore that is configured to identify objects passing through the nanopore; and detecting the presence or absence of said target polynucleotide sequence in said amplified sample by determining whether the target polynucleotide bound to the payload molecule passed through the nanopore using data from said sensor, wherein said amplified sample has not been purified.

In some embodiments, the sample is loaded into said device before said amplification. In some embodiments, the sample is loaded into said device after said amplification. In some embodiments, the amplicon is at least 200, 500, 1,000, 2,000, 5,000 or 10,000 base pairs in length. In some embodiments, the sample does not undergo a purification step between said amplification and said detection in a nanopore.

In some embodiments, the sample is loaded into said nanopore device at a dilution of 1:10000, 1:1000, 1:500, 1:200, 1:100, 1:50, 1:20, 1:10, 1:5, 1:2, 1:1.5, 1:1.2, 1:1.1 or 1:1.05. In some embodiments, the sample is loaded into said nanopore device without dilution. In some embodiments, the sample comprises non-target polynucleotides and amplification reaction reagents.

In some embodiments, the nanopore is at least 2 nm, 3 nm, 5 nm, 10 nm, 20 nm, 30 nm, 40 nm, or 50 nm in diameter.

In some embodiments, the amplification reaction is selected from the group consisting of: polymerase chain reaction (PCR), reverse transcription PCR, ligation mediated PCR, loop mediated amplification (LAMP), isothermal amplification, strand displacement amplification (SDA), multiple displacement amplification, strand displacement amplification, helicase dependent amplification, nicking enzyme amplification reaction, recombinant polymerase amplification, loop mediated isothermal amplification (LAMP<self-sustained sequence replication, whole genome amplification, or ligase mediated PCR. In some embodiments, the amplification reaction is performed in the interior space of the device.

In some embodiments, the target polynucleotide comprises double-stranded deoxyribonucleic acid (dsDNA), single-stranded DNA (ssDNA), DNA/RNA hybrid, peptide nucleic acid (PNA), single-stranded ribonucleic acid (ssRNA), or double-stranded ribonucleic acid (dsRNA). In some embodiments, the target polynucleotide is a naturally-occurring polynucleotide. In some embodiments, the target polynucleotide is an artificially synthesized polynucleotide. In some embodiments, the target polynucleotide is a recombinant polynucleotide.

In some embodiments, the sensor comprises an electrode pair configured to apply a voltage differential between the two volumes and to measure current flow through the nanopore separating the two volumes, generating a current event signature. In some embodiments, the current event signature generated when the target polynucleotide passes through the nanopore is distinguishable from the current event signature of background molecules by its mean depth, maximum depth, duration, number of depth levels, area of depth and duration, or noise level.

In some embodiments, the device comprises at least two nanopores in series, and wherein said amplicon is simultaneously in said at least two nanopores during translocation.

Also provided herein is a kit comprising: a device comprising a nanopore, wherein said nanopore separates an interior space of the device into two volumes, and configuring the device to pass the nucleic acid through one or more pores, wherein the device comprises a sensor for each pore that is configured to identify objects passing through the nanopore; a primer set, wherein at least one of said primers is hybridizable to a polynucleotide comprising said target polynucleotide sequence, and wherein at least one of said primers is modified to comprise a conjugation site capable of specifically binding to a payload molecule; a payload molecule for binding to said conjugation site prior to, during, or after amplification; instructions for use to detect the presence or absence of said target polynucleotide in a sample.

Also provided herein is a kit comprising: a device comprising a nanopore, wherein said nanopore separates an interior space of the device into two volumes, and configuring the device to pass the nucleic acid through one or more pores, wherein the device comprises a sensor for each pore that is configured to identify objects passing through the nanopore; a primer set, wherein at least one of said primers is hybridizable to a polynucleotide comprising said target polynucleotide sequence, and wherein at least one of said primers is bound to a payload molecule; instructions for use to detect the presence or absence of said target polynucleotide in a sample.

Also provided herein is a kit comprising: a device comprising a nanopore, wherein said nanopore separates an interior space of the device into two volumes, and configuring the device to pass the nucleic acid through one or more pores, wherein the device comprises a sensor for each pore that is configured to identify objects passing through the nanopore; a primer set, wherein at least one of said primers is hybridizable to a polynucleotide comprising said target polynucleotide sequence, wherein said primers generate an amplicon comprising said target polynucleotide sequence of at least 100, 200, 500, 1,000, 2,000, 5,000, or 10,000 base pairs during an amplification reaction; and instructions for use to detect the presence or absence of said target polynucleotide in a sample.

Also provided herein is a method for quantifying the amount of target polynucleotide sequence present in a sample, comprising: providing a control sample comprising a known amount of a control polynucleotide and an experimental sample comprising an unknown amount of target polynucleotide; amplifying said control sample to generate a first amplicon comprising said control polynucleotide and amplifying said experimental sample to generate a second amplicon comprising said target polynucleotide; loading said control sample and said experimental sample separately into a device comprising a nanopore, wherein said nanopore separates an interior space of the device into two volumes, and configuring the device to pass the first or second amplicon through one or more pores, wherein the device comprises a sensor for each pore that is configured to identify objects passing through the nanopore; and comparing the capture rate of said first amplicon in the nanopore with the capture rate of said second amplicon in the nanopore to quantify the amount of target polynucleotide sequence in said experimental sample.

In some embodiments, the amplification is performed after loading said control sample or said experimental sample into said device. In some embodiments, the control sample and said experimental sample are amplified under identical conditions. In some embodiments, the control polynucleotide and said target polynucleotide are of the same length or sequence. In some embodiments, the capture rate of the first and second amplicon are determined using the same nanopore under the same conditions. In some embodiments, the capture rate of the first and second amplicon are determined using nanopores of similar size.

In some embodiments, an estimate for the concentration of the target polynucleotide in the experimental sample is mathematically generated by aggregating the set of sensor measurements recorded over time for said control sample and said experimental sample and comparing the two sets of data to convert capture rate to concentration. In some embodiments, an estimate for the concentration of the target polynucleotide is mathematically generated by aggregating the set of sensor measurements recorded over time for said control sample and said experimental sample after each cycle within an amplification reaction and comparing the two sets of data to convert capture rate to concentration.

In some embodiments, the method further comprises determining the amount of target polynucleotide in said experimental sample before amplification from said comparison of sensor measurements.

Also provided herein is a method for quantifying the amount of target polynucleotide sequence present in a sample, comprising: providing a control sample comprising a known amount of a control polynucleotide and an experimental sample comprising an unknown amount of target polynucleotide; diluting said control sample to generate at least two different known concentrations of said control polynucleotide; loading said control sample into a device comprising a nanopore at said at least two different known concentrations of said control polynucleotide, wherein said nanopore separates an interior space of the device into two volumes, and configuring the device to pass the control polynucleotide through one or more pores, wherein the device comprises a sensor for each pore that is configured to identify objects passing through the nanopore; detecting the capture rate in said nanopore of the control polynucleotide at each of said at least two known concentrations; amplifying said experimental sample to generate an amplicon comprising said target polynucleotide; loading the experimental sample into said device comprising a nanopore; detecting the capture rate of the target polynucleotide in said nanopore; and comparing the capture rate of said first amplicon in the nanopore with the capture rate of said second amplicon in the nanopore to quantify the amount of target polynucleotide sequence in said experimental sample.

In some embodiments, the dilution is a serial dilution. In some embodiments, the method further comprises amplifying said control polynucleotide. In some embodiments, the dilution is performed after loading said control sample into said device. In some embodiments, the amplification is performed after loading said experimental sample in to said device.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention. Provided also as embodiments of this disclosure are data figures that illustrate features by exemplification only, and not limitation.

DETAILED DESCRIPTION

Figure 1:
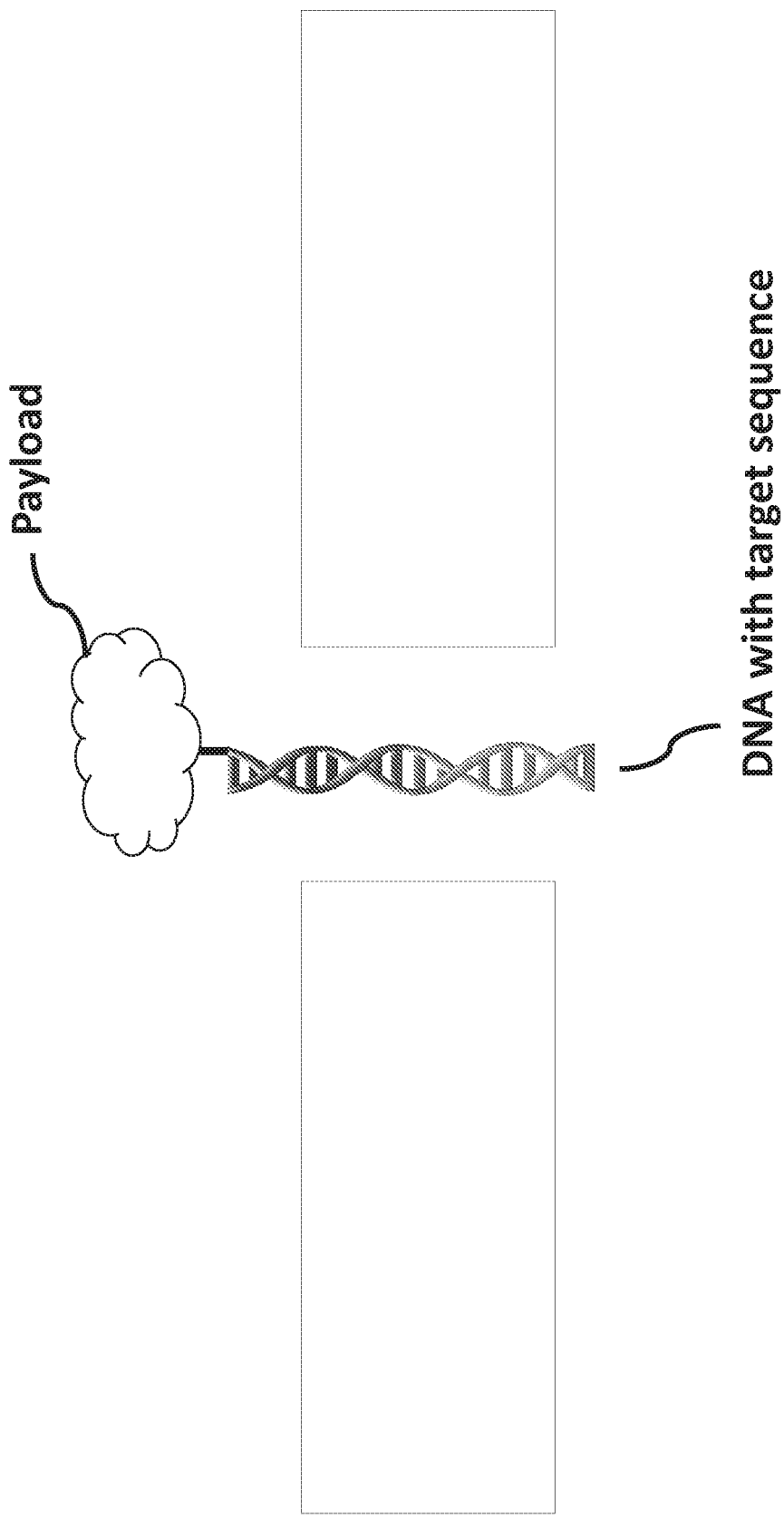
FIG. 1 depicts a polynucleotide comprising a target polynucleotide sequence bound to a payload molecule passing through the nanopore.

Throughout this application, the text refers to various embodiments of the present devices, compositions, systems, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

Also throughout this disclosure, various publications, patents and published patent specifications are referenced by an identifying citation. The disclosures of these publications, patents and published patent specifications are hereby incorporated by reference into the present disclosure in their entireties As used herein, the term "comprising" is intended to mean that the systems, devices, and methods include the recited components or steps, but not excluding others. "Consisting essentially of" when used to define systems, devices, and methods, shall mean excluding other components or steps of any essential significance to the combination. "Consisting of" shall mean excluding other components or steps. Embodiments defined by each of these transition terms are within the scope of this invention.

All numerical designations, e.g., distance, size, temperature, time, voltage and concentration, including ranges, are approximations which are varied (+) or (−) by increments of 0.1. It is to be understood, although not always explicitly stated that all numerical designations are preceded by the term "about". It also is to be understood, although not always explicitly stated, that the components described herein are merely exemplary, and that equivalents of such are known in the art.

As used herein, "a device comprising a nanopore that separates an interior space" shall refer to a device having a pore that comprises an opening within a structure, the structure separating an interior space into two volumes or chambers. The device can also have more than one nanopore, and with one common chamber between every pair of pores.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA.

As used herein, the term "target polynucleotide" refers to a polynucleotide comprising a sequence of interest (i.e., a target polynucleotide sequence or a target sequence). A target polynucleotide can include regions (e.g., sufficiently complementary sequences) for hybridizing to primers for amplification of the target polynucleotide. These regions can be part of the sequence of interest, flanking the sequence of interest, or further upstream or downstream of the sequence of interest in sufficient proximity to allow amplification of the sequence of interest via an amplification reaction. In some embodiments, these regions for hybridizing to primers are located at the two ends of the amplicon generated by an amplification reaction. Described herein are methods, devices, and compositions for detecting a target polynucleotide comprising a sequence of interest.

The term "primer" as used herein refers to an oligomer which is capable of acting as a point of initiation of synthesis of a polynucleotide strand (e.g., a target polynucleotide) to be copied. Thus, under conditions conducive to hybridization, the primer will anneal to the complementary region of the polynucleotide comprising the target sequence. Upon addition of suitable reactants, (e.g., a polymerase, nucleotide triphosphates, and the like), the primer is extended by the polymerizing agent to form a copy of the target polynucleotide. The primer may be single-stranded, or alternatively may be partially or fully double-stranded.

As used herein, the term "hybridizable" refers to capable of hybridizing, i.e., forming a double strand molecule such as RNA:RNA, RNA:DNA and/or DNA:DNA molecules. For purposes of amplification, a primer is hybridizable to a target polynucleotide when it is capable of forming a duplex with a strand of the target polynucleotide via complementary base pairing interactions sufficient to act as a starting point for DNA synthesis for the amplification reaction.

As used herein, the term binding refers to the formation of a chemical bond, e.g., a covalent bond, an ionic bond, or a metallic bond. Binding can include a stable association between two molecules via a van der Waals force, a hydrophobic interaction, a cation-pi interaction, and/or a planar stacking interaction. Binding includes conjugation of two molecules via click chemistry.

As used herein, the term "conjugation site" refers to a site on a molecule for conjugation of one biomolecule to another. In some embodiments, primers disclosed herein comprise a conjugation site for conjugating either the primer itself, or an amplicon generated by the primer, to a payload molecule for detection of a payload-bound amplicon in a nanopore. The mechanism of binding to the conjugation site can include any stable binding interaction, e.g., click chemistry.

As used herein, the term "amplification" or "amplification reaction" refers to a reaction that generates a plurality of clonal amplicons comprising a target polynucleotide sequence from the target polynucleotide sequence. As used herein, amplification reaction reagents include any molecules that are necessary to perform amplification of the target polynucleotide sequence. Amplification reaction reagents can include, but are not limited to, free primers, dNTPs (deoxynucleotide triphosphates, dATP, dGTP, dCTP, dTTP), polymerase enzymes (e.g., Taq or Pfu), salts (Magnesium chloride, Magnesium Sulfate, Ammonium sulfate, sodium chloride, potassium chloride), BSA (bovine serum albumin) stabilizer, and detergents (e.g., triton X-100). Amplification reactions can include, but are not limited to, e.g., PCR, ligase chain reaction (LCR), transcription mediated amplification (TMA), reverse transcriptase initiated PCR, DNA or RNA hybridization techniques, sequencing, isothermal amplification, and loop-mediated isothermal amplification (LAMP). Techniques of amplification to generate an amplicon from a target polynucleotide sequence are well known to one of skill in the art.

As used herein, the term "scaffold" or "polymer scaffold" refers to a negatively or positively charged polymer that translocates through a nanopore upon application of voltage. In some embodiments, a polymer scaffold comprises a cleavable domain or cleavable linker. In some embodiments, a polymer scaffold capable of binding or bound to a fusion molecule comprising a cleavable linker and translocating through a pore upon application of voltage. In some aspects, the polymer scaffold comprises a deoxyribonucleic acid (DNA), a ribonucleic acid (RNA), a peptide nucleic acid (PNA), a DNA/RNA hybrid, or a polypeptide. The scaffold may also be a chemically synthesized polymer, and not a naturally occurring or biological molecule. In a preferred embodiment, the polymer scaffold is dsDNA to allow more predictable signals upon translocation through the nanopore and reduce secondary structure present in ssDNA or RNA. In some embodiments, the polymer scaffold comprises a fusion molecule binding site that may reside on the end of the scaffold, or at both ends of the scaffold. The scaffold and fusion molecule may be connected via a covalent bond, a hydrogen bond, an ionic bond, a van der Waals force, a hydrophobic interaction, a cation-pi interaction, a planar stacking interaction, or a metallic bond. Alternatively, direct covalent tethering of the cleavable linker component to the scaffold may connect the scaffold and the fusion molecule. Alternatively, a connector component of the fusion may join the cleavable linker to the scaffold via direct covalent tethering. In a preferred embodiment, the fusion molecule comprises a scaffold-binding domain can be a DNA, RNA, PNA, polypeptide, a cholesterol/DNA hybrid, or a DNA/RNA hybrid.

As used herein, the term "payload" or "payload molecule" refers to molecules or compounds that are bound to a polynucleotide (e.g., a primer) to enhance selectivity and/or sensitivity of detection in a nanopore. In some embodiments, the payload molecule can be a dendrimer, double stranded DNA, single stranded DNA, a DNA aptamer, a fluorophore, a protein, a polypeptide, a nanorod, a nanotube, fullerene, a PEG molecule, a liposome, or a cholesterol-DNA hybrid. In preferred embodiments, the polynucleotide and the payload are connected directly or indirectly via a covalent bond, a hydrogen bond, an ionic bond, a van der Waals force, a hydrophobic interaction, a cation-pi interaction, a planar stacking interaction, or a metallic bond. The payload adds size to the target polynucleotide or amplicon, and facilitates detection, with the amplicon bound to the payload having a markedly different current signature when passing through the nanopore than background molecules.

As used herein, the term "background" refers to molecules in a sample that are detectable by a nanopore but do not include the target polynucleotide sequence of interest. An important aspect of this invention is the discrimination of target polynucleotides from background in a mixed sample.

As used herein, the term "nanopore" refers to an opening (hole or channel) of sufficient size to allow the passage of particularly sized polymers. With an amplifier, voltage is applied to drive negatively charged polymers through the nanopore, and the current through the pore detects if molecules are passing through it.

As used herein, the term "sensor" refers to a device that collects a signal from a nanopore device. In many embodiments, the sensor includes a pair of electrodes placed at two sides of a pore to measure an ionic current across the pore when a molecule or other entity, in particular a polymer scaffold, moves through the pore. In addition to the electrodes, an additional sensor, e.g., an optical sensor, may be to detect an optical signal in the nanopore device. Other sensors may be used to detect such properties as current blockade, electron tunneling current, charge-induced field effect, nanopore transit time, optical signal, light scattering, and plasmon resonance.

As used herein, the term "current measurement" refers to a series of measurements of current flow at an applied voltage through the nanopore over time. The current is expressed as a measurement to quantitate events, and the current normalized by voltage (conductance) is also used to quantitate events.

As used herein, the term "open channel" refers to the baseline level of current through a nanopore channel within a noise range where the current does not deviate from a threshold of value defined by the analysis software.

As used herein, the term "event" refers to a set of current impedance measurements that begins when the current measurement deviates from the open channel value by a defined threshold, and ends when the current returns to within a threshold of the open channel value.

As used herein, the term "current impedance signature" refers to a collection of current measurements and/or patterns identified within a detected event. Multiple signatures may also exist within an event to enhance discrimination between molecule types.

As used herein, the term "capture rate" refers to the number of events detected over time in a nanopore device. In some embodiments, the capture rate can refer specifically to the rate of capture and/or translocation of events associated with a specific target molecule, e.g., translocation of a payload-bound amplicon. As described herein, the capture rate can be used to infer concentration as compared to a control with a similar mass/charge ratio under similar nanopore conditions.

Overview

Disclosed herein are method of detecting target polynucleotides by generation of modified amplicons detectable in a nanopore device. The methods, compositions, and devices disclosed herein allow purely electrical counting of DNA molecules as they pass through a nanopore. Examples provided within demonstrate "payload attached DNA" provides a definitive and robust signal each time a single DNA molecule passes through the nanopore. This allows a fast and simple means of accurate and precise DNA quantitation from a mixed sample, allowing 100s to 1000s of target molecules to be counted and distinguished from background non-target molecules in minutes using an electrical detection method that does not require chemical or optical detection. Additionally, given the inexpensive hardware of the device, low power requirements, small size, and the tolerance to a range of nanopore geometries, fabrication and device costs are extremely low. The features provided by several embodiments of the inventions disclosed herein, along with a small nanopore device size that allows portability, provides a novel and efficient method of polynucleotide target sequence detection and diagnostics.

Background Discrimination

In some aspects, the target polynucleotide present in the sample can be from original (even filtered) natural fluids (blood, saliva, urine, etc.), which have a vast population of background molecules. Such background molecules, when sufficiently negatively charged with a positive applied voltage, and pass through the nanopore. In some cases, such nanopore events may appear to look like the target polynucleotide. As such, these background molecules can produce false positives, generating a high error rate of detection. Adding sufficient sample prep to remove larger molecules will help this, but background molecules that create false positive events will still be present, harming the sensitivity and specificity of detection of the target polynucleotides in a nanopore device.

To provide discrimination between background molecules and target polynucleotides, a primer-labeling scheme can be used.

Specifically, a label or a sequence of labels (e.g., payload molecules) are bound to a primer or probe that is hybridizable to a sequence of the target polynucleotide. Alternatively, the primer or probe has a label binding site that specifically binds to a chosen label or payload molecule. During amplification of the target polynucleotide, these primers or probes are incorporated into an amplicon, thus incorporating the label or payload molecule or the label/payload molecule binding site into the amplicon comprising the target polynucleotide. An amplicon bound to the payload molecule provides a unique current signature that can be used to identify the presence and/or identity of a target polynucleotide/amplicon product containing the target sequence that has translocated through a nanopore.

In another embodiment, the amplicon alone (not bound to a label) provides a discriminatory signature that is sufficient distinct from background. These embodiments generally require smaller nanopores and/or longer amplicons to generate sufficient signal to discriminate from background.

Detection of target polynucleotides in a mixed sample

A solid-state nanopore can be used to electrically detect an amplicon DNA, and a payload attachment facilitates detection of a target DNA when payloads bind only to target DNA (FIG. 1).

Figure 2:
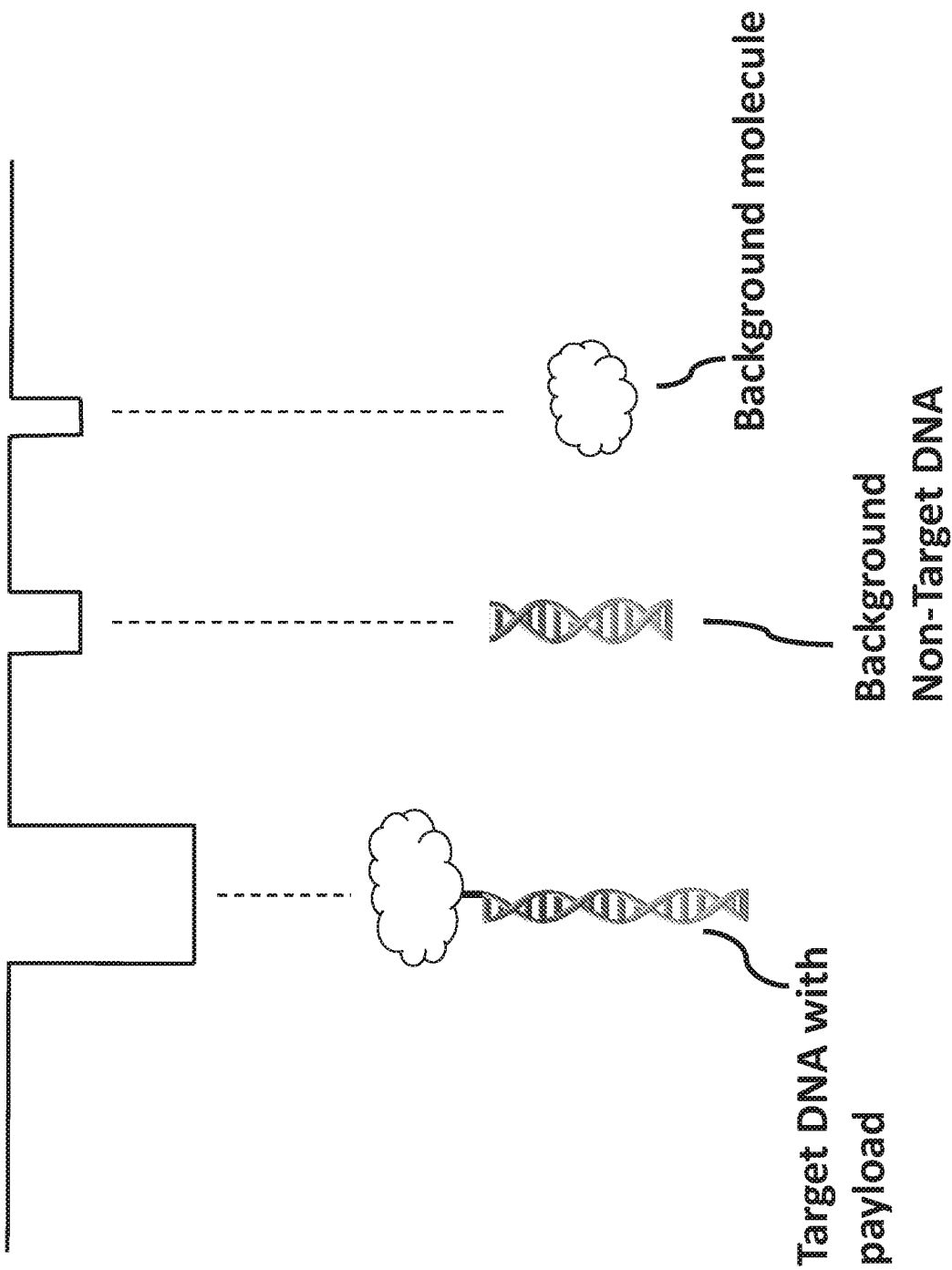
FIG. 2 depicts differences in current signatures when a payload-bound target polynucleotide passes through the pore, compared to a non-target polynucleotide and a generic non-polynucleotide background molecule.
Figure 3:
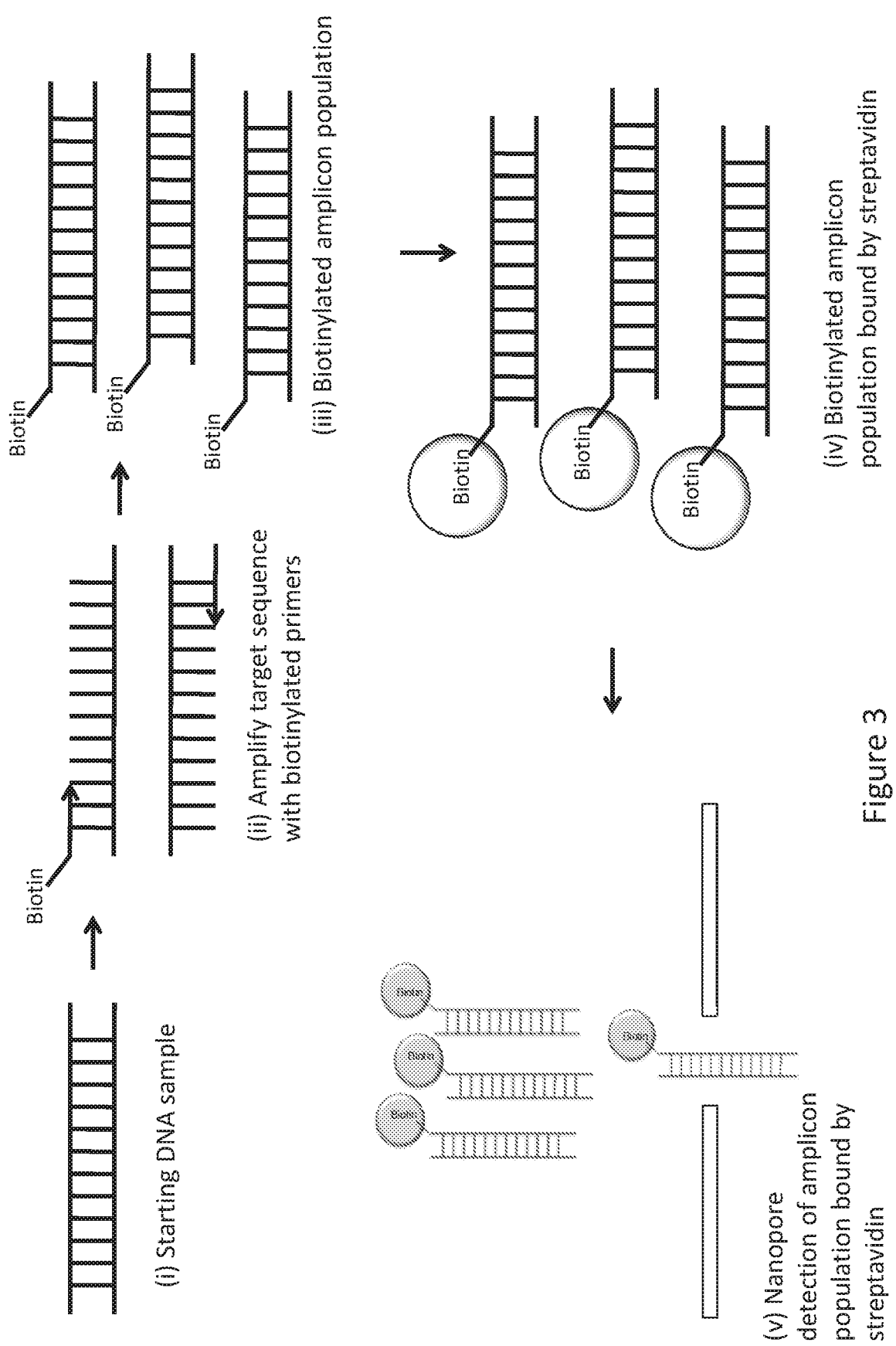
FIG. 3 depicts a process for amplifying a target sequence with biotinylated primers, and then detecting the biotinylated amplicons bound by streptavidin with a nanopore.

In particular, a solid state nanopore can be used to electrically detect the amplicon if it provides an impedance signal, while traversing through the pore, that is sufficiently greater than the open channel conductance and any noise or background molecules present while recording (FIG. 2). Adding "bulk" to a target sequence enables nanopore detection in larger pores (5-100 nm) since the bulk will provide the necessary signal that is easily measured above background noise and molecules. Without the bulk, for amplicons shorter than 500 bp, the majority of amplicons are also missed for nanopores ~5 nm and larger, preventing accurate quantitation of PCR product. For example, by performing an amplification reaction with modified primer(s), the modification in the primer will be incorporated into the amplicon, and this modification can be used to tag the amplicon with the necessary payload "bulk" to enable detection in the nanopore. In one embodiment, as shown in FIG. 3, the primer is modified with biotin. The resulting PCR amplicons are bound to a streptavidin payload and their presence is detected in a nanopore.

The examples of bulking presented include biotin/streptavidin, and epitope/antibody, and are two example methods. Alternatively, the primer can be modified with a chemically reactive group, for example an alkyne. This would enable the alkyne containing amplicons to be modified by a bulky azide containing molecule, azido-polyethyleneglycol (PEG) for example, using click chemistry. If optical detection through the pore is to be used, the primer can be modified by a fluorophore, thus the amplicon can be detected by means of fluorescence. In summary, any method that incorporates a molecule whose incorporation is dependent on the amplification reaction, is incorporated in the disclosures herein.

The binding reaction is of such high affinity, PCR amplicons can be tagged without first purifying it or extracting from the amplification buffer and components. After tagging, the amplicon is detected using a nanopore in an appropriate nanopore recording buffer (e.g. 1 M LiCl, 10 mM Tris, 1 mM EDTA). Background related to the PCR reaction mixture or from the sample will be given distinctly different nanopore current impedance signatures than the payload-bound target DNA molecule (FIG. 2). In this way, quantitation can be performed in the presence of background, eliminating the need for purification of the sample or of the PCR reaction mixture, greatly simplifying the workflow. In turn, a device that implements cyclical PCR reactions, and performs nanopore measurements of amplicon product between cycles, can be packaged and made inexpensively, by requiring only dilutions of the reaction mixture prior to measurements. A device requiring complex purification steps, on the other hand, would be more intensive in infrastructure and thus more expensive and complex.

Figure 4:
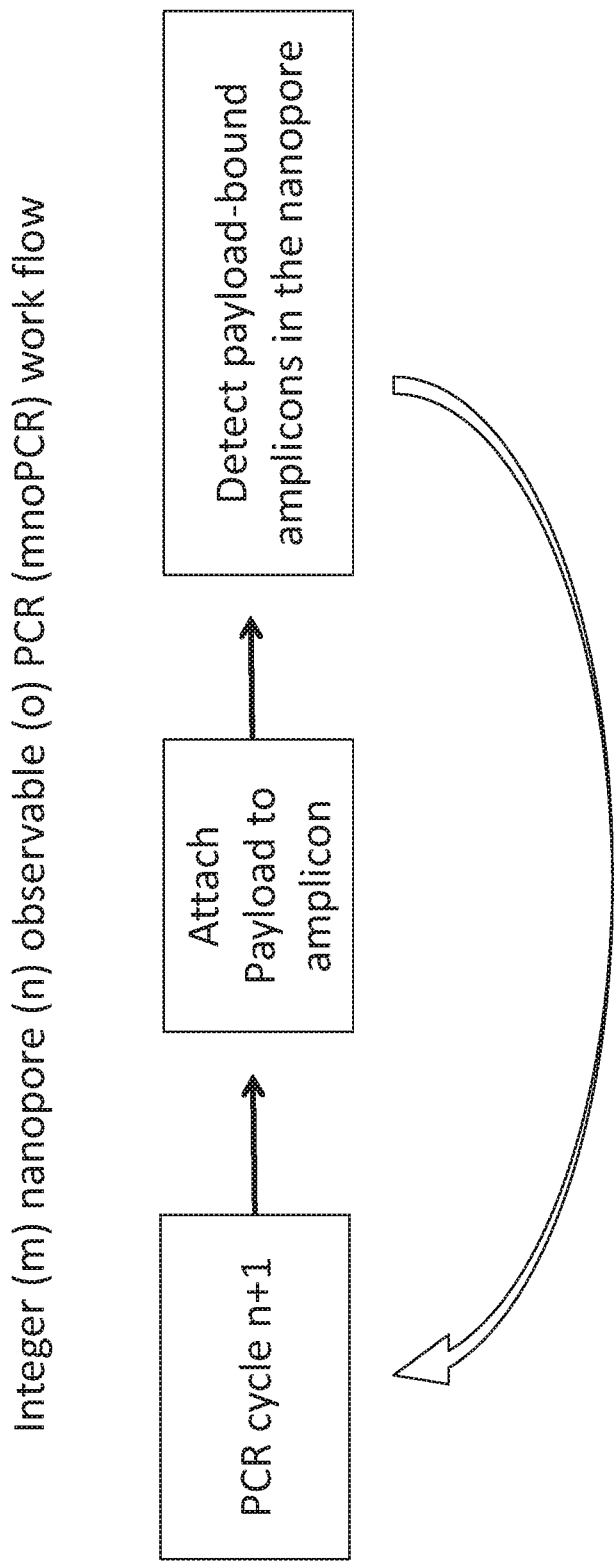
FIG. 4 depicts our Integer (m) nanopore (n) observable (o) PCR (mnoPCR) workflow, as part of the method of quantitating PCR amplicons.

FIG. 4 shows a method of real-time amplicon detection and quantitation, entitled "mnoPCR" (Integer (m) nanopore (n) observable (o) PCR). As mnoPCR proceeds, the product generated after each cycle is payload-bound and then detected in the nanopore. This real-time detection method is realized since the PCR amplicons do not need to be purified prior to binding the bulky payload that facilitates detection. The measurement is tolerant to PCR reaction mixture background at varying dilutions (including no dilution), sample background at varying dilutions (according to the requirements for optimizing the PCR reaction), and payload background (excess payload not attached to target polynucleotides).

The ability to measure product as the reaction progresses provides a very efficient way of comparing two or more samples that may differ in template/target number or concentration. Furthermore, since the nanopore detect and counts single molecules, accurate quantitation of the amount of resulting amplicon is achievable as shown in the Examples.

Using the methods described herein, two or more samples that differ in the amount of target nucleotide sequence can be compared and contrasted. Two non-limiting scenarios of this are 1) samples that contain a mix of mutant transcripts and wild-type sequence, and 2) samples that differ in the content of transgene.

For scenario 1, by amplifying samples with a primer set that amplifies target sequence regardless of whether it contains mutation, and then comparing the amount of product generated to that generated with a primer set that only amplifies the mutant sequence, one can infer the amount of mutant transcript in a sample and compare that value between samples. For example, one could tell sample A contains 20% KRAS mutation, while sample B contains 30% KRAS mutation.

For scenario 2, one can amplify a section of DNA that is present in every transcript (housekeeping region) and compare its abundance to the amount of transcript generated from a reaction that only targets the transgene. Total amount of material can be determined using the nanopore to quantitate the housekeeping amplicons and a comparison can be made to the amount of transgene amplicon produced. Two different samples that differ in starting concentration can be compared for transgene abundance since the housekeeping gene amplicons are used to determine total concentration of the sample.

These same concepts can be used to determine if a genus of bacteria is present in a sample, e.g., from a mouth swab, and then further delineate the species contained from the genus. Specifically, a gene present in all bacteria is first quantitated, e.g. *Staphylococcus* bacteria, followed by specifically amplifying and quantitating a gene present only in antibiotic resistant Staph, such as mecA.

Figure 5:
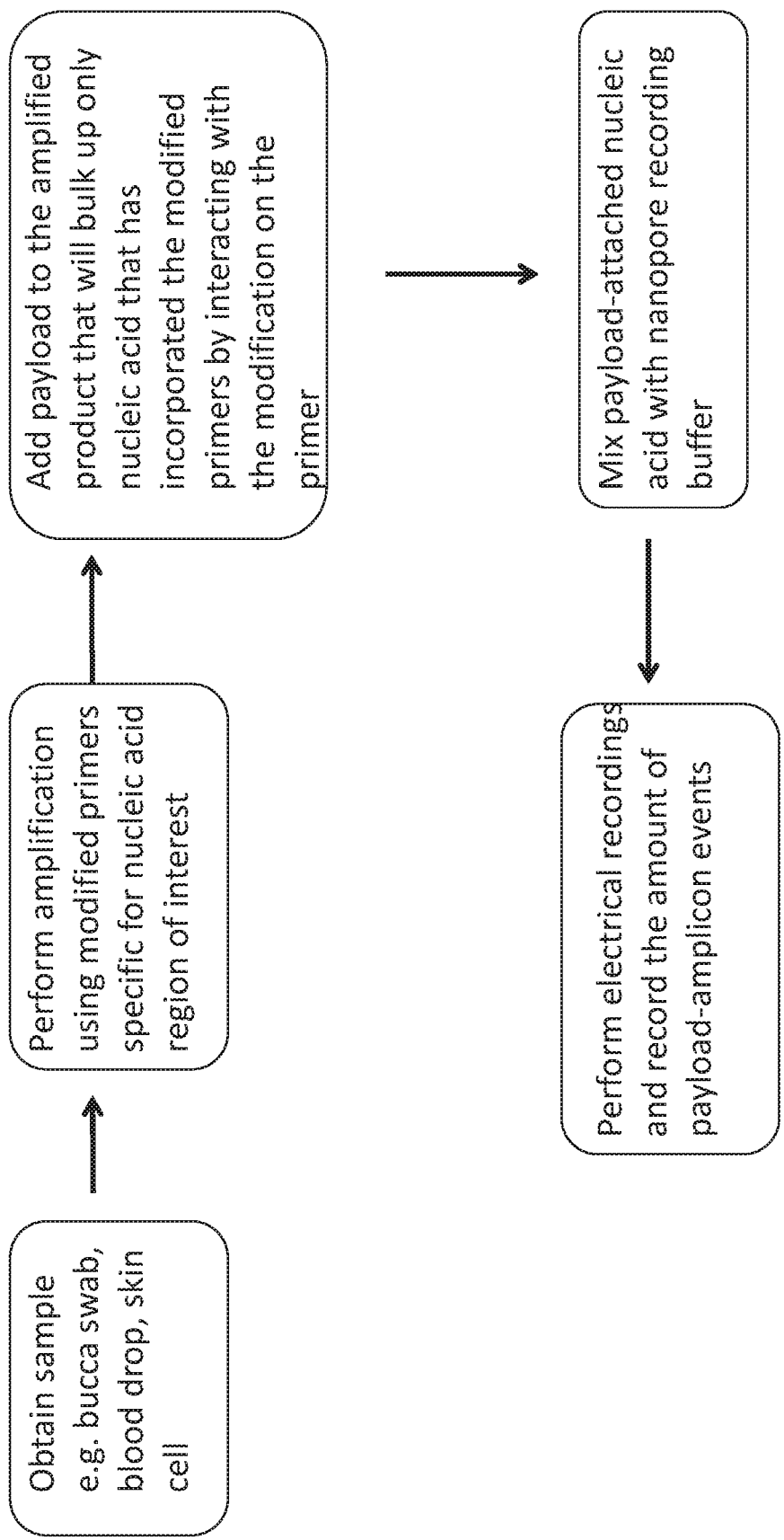
FIG. 5 depicts a workflow for detecting the target sequence that does not require purification before or after amplification or the attachment of payloads.

FIG. 5 depicts a workflow for detecting a nucleic acid sequence of interest using the disclosed method.

Assigning Statistical Significance to Detection

In some embodiments, aggregating the set of sensor measurements recorded over time and applying mathematical tools are performed to assign a numerical confidence value to detection of the target polynucleotide suspected to be present in a sample, as detailed in the previous section.

A quantitative method of discriminating a molecule type from background (i.e., other molecule types) based on differences in nanopore event population characteristics was recently developed (Morin, T. J., et al., "Nanopore-based target sequence detection," submitted to *PloS One*, Dec. 31, 2015). This method of discrimination means a specific molecule type can be detected among the presence of varying types of other background molecules, and that the statistical significance of detection can be assigned (e.g., detection of reagent X with 99% confidence). To apply the method to the examples provided below, we first summarize the method here.

In general terms, there are two categories of molecules in the chamber above the pore: type 1 are all the background molecules, and type 2 are the molecules of interest. In Examples below, target DNA-payload is commonly considered as the type 2 molecules, with non-target DNA or free payload, primers, or molecules from the sample or PCR reaction mixture being considered as background (type 1). Based on data from experiments, we identify an event signature criterion that is present in a significant fraction of type 2 events, and present in a relatively smaller fraction of type 1 events. The signature criterion could depend on $\delta G$, duration, the number and characteristics of levels within each event, and/or any other numeric value or combination of values computed from the event signal.

Note that the event signature criterion can be chosen manually, or by table look-up, or in an automated fashion. For example, prior experiments can establish the performance of positive and negative controls for a range of pore sizes and other conditions expected to be present in a given test, and the chosen criteria identified from such controls can be used (in a table look-up fashion) when comparable conditions are encountered for a given test (i.e., for a given amplicon length and for a given payload type). Automated criteria can be identified in real-time also, based on a control run just prior to a sample, for example. For quantitation of PCR amplicons in real-time, as disclosed in this application, automated criteria selection is a suitable and preferred approach. Specifically, as the controls emulate the amplicons in molecular size/charge and in nanopore event characteristics/shape, the control events can be used to build a capture-rate vs. concentration trend, as disclosed, while also providing the event population with which to automate the calculation of a "type 2 event boundary" that establishes the criteria for flagging "amplicon" type 2 events from among background, when measuring the amplified sample. The boundary could be computed by any method of fitting a curve around points in a 2D plot (e.g., the points being the events within the mean shift vs. duration plot). Curve fitting methods can involve least-squares, linear or quadratic programming, or any form of numerical optimization, and parameterizing the boundary via the coefficients of piecewise polynomials or splines. Computing the convex hull can provide a boundary. Higher dimensional boundary fitting routines are also possible, e.g., using 3 properties that characterize the events (3D boundary). The resulting boundary could be polygonal, or smooth. A relevant technique, for the purpose of enclosing a subset of the events with a boundary that includes a specific percentage of the events (i.e., as a mechanism to trim outliers when enclosing the points for automated criteria identification), is to compute a z-quantile boundary, defined as the boundary of the smallest region that contains z fraction of total probability. For example, the 95%-quantile boundary is the boundary of the smallest region that contains 95% of total probability (95% of the data). Although the probability density is unknown, it can be estimated using the data, using standard techniques.

Once a criterion is chosen (manually, by table look up, or in an automated fashion), an event is "tagged" as being type 2 if the signature criterion is met for that event. We define p as the probability that a capture event is type 2. In control experiments without type 2 molecules p=0, and in experiments with type 2 molecules p>0 but its value is not known. We define the false positive probability q1=Pr(tagged|type 1 event). In a control experiment or set of experiments without type 2 molecules (e.g., with PCR reaction mixture after 20 cycles using a non-target DNA, and diluted into recording buffer adjacent to the nanopore), q1 is determined with good accuracy from a reasonable number of capture events. In a detection experiment to determine if type 2 molecules are present in bulk solution, the probability that a capture event is tagged is a function of p and can be approximated as:

$Q(p)$=(Number of tagged events)/$N$

In the formula, N is the total number of events. The 99% confidence interval $Q(p) \pm Q_{sd}(p)$ can be computed with $Q_{sd}(p)=2.57*\text{sqrt}\{Q(p)*(1-Q(p))/N\}$, with sqrt{ } the square root function. During the course of an experiment, the value for Q(p) converges and the uncertainty bounds attenuate as the number of events N increases. A plot of $Q(p) \pm Q_{sd}(p)$ as a function of recording time shows how it evolves for each reagent type (FIGS. 10, 17, 19 and 22). In a control experiment without type 2 molecules, observe that Q(0)=q1. In a control experiment with type 2 molecules known to be present at some probability p*>0, the computed value Q(p*) can be used in a detection experiment to determine if type 2 molecules are absent, as defined below.

In a detection experiment, type 2 molecules are present with 99% confidence when the following criteria is true:

$$Q(p) - Q_{sd}(p) > q1 \qquad (1.)$$

If the criteria above is true, we conclude p>0; if it is untrue, we cannot say p>0. The framework is utilized in the Examples provided below.

Estimating the Concentration from Measured Capture Rates

Here we discuss how to estimate the concentration based on a linear relation represented by measured capture rates corresponding to a sequence of known concentrations of a target molecule. This is established using controls. Let C denote the concentration, and r(C) denote the true/exact capture rate corresponding to concentration C. We expect that r(C) is proportional to C.

$r(C) = a\, C$

We collect measured capture rates corresponding to a sequence of known concentrations $\{C_1, C_2, \ldots, C_N\}$. Each of the measured capture rates is in the form of Measured capture rate for $C_j$: $r_j \pm d_j$ We interpret the measured capture rate for as follows: $r_j$ is a random sample from the normal distribution $N(a\, C_j, d_j^2)$, where $a\, C_j$ is the exact capture rate and the rate constant a is unknown. Given the data set $\{r_j \pm d_j, j=1, 2, \square, N\}$, the posterior distribution of a has a normal distribution: $a \sim N(u, s^2)$, where u and s have the expressions $$s^2 = \frac{1}{\sum_{j=1}^{N} \left(\frac{C_j}{d_j}\right)^2},$$

$$u = \frac{1}{\sum_{j=1}^{N} \left(\frac{C_j}{d_j}\right)^2} \sum_{j=1}^{N} \frac{r_j}{C_j}\left(\frac{C_j}{d_j}\right)^2$$

Representative examples for fitting to the controls in capture rate vs. concentration plots are shown in FIGS. 23-25, 28.

Next, we describe how to estimate concentration of an unknown by using the capture rate vs. concentration trend establishing first using the controls (as detailed above), followed by measuring the capture rate of the target molecule at unknown concentration. In terms of notation, we measure the capture rate corresponding to an unknown concentration $C_X$, and let:

Measured capture rate for $C_X$: $r_X \pm d_X$

We write $C_X$ as $$C_X = \frac{a C_X}{a} = \frac{r_X + d_X \varepsilon_1}{u + s \varepsilon_2}$$

where $e_1$ and $e_2$ are independent standard normal random variables.

$\varepsilon_1 \sim N(0,1)$ and $\varepsilon_2 \sim N(0,1)$

Assume that slope a is determined from other data points with small relative uncertainty: s/u<<1. Under this assumption, we can approximate $C_X$. Specifically, We will report the estimated value of $C_X$ as $$C_X = \frac{r_X}{u}\left(1 + \sqrt{\left(\frac{d_X}{r_X}\right)^2 + \left(\frac{s}{u}\right)^2}\right)$$

where u and s are calculated from data points using $$s^2 = \frac{1}{\sum_{j=1}^{N} \left(\frac{C_j}{d_j}\right)^2},$$

$$u = \frac{1}{\sum_{j=1}^{N} \left(\frac{C_j}{d_j}\right)^2} \sum_{j=1}^{N} \frac{r_j}{C_j}\left(\frac{C_j}{d_j}\right)^2$$

Representative examples for estimating an unknown concentration by fitting a measured capture rate to the capture rate vs. concentration trend (established with controls) are shown in FIGS. 23-25, 28.

In the Examples provided, "Example 9: Quantitation of Amplicon Concentration" teaches by example how the methods presented in this section can be implemented.

Compositions

In some embodiments, provided herein are primers bound to a payload molecule. In some embodiments, provided herein are primers comprising a payload molecule binding site. In either embodiment, the primer can generate an amplicon that is bound or capable of binding to a payload molecule to enhance detection in a nanopore.

In some embodiments, the payload molecule can be a dendrimer, double stranded DNA, single stranded DNA, a DNA aptamer, a fluorophore, a protein, a polypeptide, a nanorod, a nanotube, fullerene, a PEG molecule, a liposome, or a cholesterol-DNA hybrid. In preferred embodiments, the polynucleotide and the payload are connected directly or indirectly via a covalent bond, a hydrogen bond, an ionic bond, a van der Waals force, a hydrophobic interaction, a cation-pi interaction, a planar stacking interaction, or a metallic bond. The payload adds size to the target polynucleotide or amplicon, and facilitates detection, with the amplicon bound to the payload having a markedly different current signature when passing through the nanopore than background molecules. In some embodiments, the payload molecule comprises an azide chemical handle for attachment to the primer. In some embodiments, the primer is bound to a biotin molecule. In some embodiments, the payload molecule can bind to another molecule to affect the bulkiness of the molecule, thereby enhancing the sensitivity of detection of the amplicon in a nanopore. In some embodiments, the primer is bound to or comprises a binding site for binding to a biotin molecule. In some embodiments, the biotin is further bound by streptavidin to increase the size of the payload molecule for enhanced detection in a nanopore over background molecules. The added bulk can produce a more distinct signature difference between amplicon comprising a target sequence and background molecules.

In this embodiment, attachment of a payload to a primer or amplicon can be achieved in a variety of ways. For example, the primer may be a dibenzocyclooctyne (DBCO) modified primer, effectively labeling all amplicons with a DBCO chemical group to be used for conjugation purposes via copper-free "click" chemistry to an azide-tagged amplicon or primer.

In some aspects, the primer comprises a chemical modification that causes or facilitates recognition and binding of a payload molecule. For example, methylated DNA sequences can be recognized by transcription factors, DNA methyltransferases or methylation repair enzymes. In other embodiments, biotin may be incorporated into, and recognized by, avidin family members. In such embodiments, biotin forms the fusion binding domain and avidin or an avidin family member is the polymer scaffold-binding domain on the fusion. Due to their binding complementarity, payload molecule binding domains on a primer/amplicon and primer binding domains on a payload molecule may be reversed so that the payload binding domain becomes the primer binding domain, and vice versa.

Molecules, in particular proteins, that are capable of specifically recognizing nucleotide binding motifs are known in the art. For instance, protein domains such as helix-turn-helix, a zinc finger, a leucine zipper, a winged helix, a winged helix turn helix, a helix-loop-helix and an HMG-box, are known to be able to bind to nucleotide sequences. Any of these molecules may act as a payload molecule binding to the amplicon or primer.

In some aspects, the payload binding domains can be locked nucleic acids (LNAs), bridged nucleic acids (BNA), Protein Nucleic Acids of all types (e.g. bisPNAs, gamma-PNAs), transcription activator-like effector nucleases (TALENs), clustered regularly interspaced short palindromic repeats (CRISPRs), or aptamers (e.g., DNA, RNA, protein, or combinations thereof).

In some aspects, the payload binding domains are one or more of DNA binding proteins (e.g., zinc finger proteins), antibody fragments (Fab), chemically synthesized binders (e.g., PNA, LNA, TALENS, or CRISPR), or a chemical modification (i.e., reactive moieties) in the synthetic polymer scaffold (e.g., thiolate, biotin, amines, carboxylates).

Nanopore Devices

A nanopore device, as provided, includes at least a pore that forms an opening in a structure separating an interior space of the device into two volumes, and at least a sensor configured to identify objects (for example, by detecting changes in parameters indicative of objects) passing through the pore. Nanopore devices used for the methods described herein are also disclosed in PCT Publication WO/2013/012881, incorporated by reference in entirety.

The pore(s) in the nanopore device are of a nano scale or micro scale. In one aspect, each pore has a size that allows a small or large molecule or microorganism to pass. In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm, or 100 nm in diameter.

In one aspect, the pore is no more than about 100 nm in diameter. Alternatively, the pore is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, or 10 nm in diameter.

In one aspect, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In some aspects, the nanopore device further includes means to move a polymer scaffold across the pore and/or means to identify objects that pass through the pore. Further details are provided below, described in the context of a two-pore device.

Compared to a single-pore nanopore device, a two-pore device can be more easily configured to provide good control of speed and direction of the movement of the polymer scaffold across the pores.

In one embodiment, the nanopore device includes a plurality of chambers, each chamber in communication with an adjacent chamber through at least one pore. Among these pores, two pores, namely a first pore and a second pore, are placed so as to allow at least a portion of a target polynucleotide to move out of the first pore and into the second pore. Further, the device includes a sensor at each pore capable of identifying the target polynucleotide during the movement. In one aspect, the identification entails identifying individual components of the target polynucleotide. In another aspect, the identification entails identifying payload molecules bound to the target polynucleotide. When a single sensor is employed, the single sensor may include two electrodes placed at both ends of a pore to measure an ionic current across the pore. In another embodiment, the single sensor comprises a component other than electrodes.

In one aspect, the device includes three chambers connected through two pores. Devices with more than three chambers can be readily designed to include one or more additional chambers on either side of a three-chamber device, or between any two of the three chambers. Likewise, more than two pores can be included in the device to connect the chambers.

In one aspect, there can be two or more pores between two adjacent chambers, to allow multiple polymer scaffolds to move from one chamber to the next simultaneously. Such a multi-pore design can enhance throughput of target polynucleotide analysis in the device. For multiplexing, one chamber could have a one type of target polynucleotide, and another chamber could have another target polynucleotide type.

In some aspects, the device further includes means to move a target polynucleotide from one chamber to another. In one aspect, the movement results in loading the target polynucleotide (e.g., the amplification product or amplicon comprising the target sequence) across both the first pore and the second pore at the same time. In another aspect, the means further enables the movement of the target polynucleotide, through both pores, in the same direction.

For instance, in a three-chamber two-pore device (a "two-pore" device), each of the chambers can contain an electrode for connecting to a power supply so that a separate voltage can be applied across each of the pores between the chambers.

In accordance with one embodiment of the present disclosure, provided is a device comprising an upper chamber, a middle chamber and a lower chamber, wherein the upper chamber is in communication with the middle chamber through a first pore, and the middle chamber is in communication with the lower chamber through a second pore. Such a device may have any of the dimensions or other characteristics previously disclosed in U.S. Publ. No. 2013-0233709, entitled Dual-Pore Device, which is herein incorporated by reference in its entirety.

In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm, or 100 nm in diameter.

In one aspect, each pore is no more than about 100 nm in diameter. Alternatively, the pore is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, or 10 nm in diameter.

In one aspect, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In some aspects, the pore has a substantially round shape. "Substantially round", as used here, refers to a shape that is at least about 80 or 90% in the form of a cylinder. In some embodiments, the pore is square, rectangular, triangular, oval, or hexagonal in shape.

In one aspect, the pore has a depth that is between about 1 nm and about 10,000 nm, or alternatively, between about 2 nm and about 9,000 nm, or between about 3 nm and about 8,000 nm, etc.

In some aspects, the nanopore extends through a membrane. For example, the pore may be a protein channel inserted in a lipid bilayer membrane or it may be engineered by drilling, etching, or otherwise forming the pore through a solid-state substrate such as silicon dioxide, silicon nitride, grapheme, or layers formed of combinations of these or other materials. Nanopores are sized to permit passage through the pore of the scaffold:fusion:payload, or the product of this molecule following enzyme activity. In other embodiments, temporary blockage of the pore may be desirable for discrimination of molecule types.

In some aspects, the length or depth of the nanopore is sufficiently large so as to form a channel connecting two otherwise separate volumes. In some such aspects, the depth of each pore is greater than 100 nm, 200 nm, 300 nm, 400 nm, 500 nm, 600 nm, 700 nm, 800 nm, or 900 nm. In some aspects, the depth of each pore is no more than 2000 nm or 1000 nm.

In one aspect, the pores are spaced apart at a distance that is between about 10 nm and about 1000 nm. In some aspects, the distance between the pores is greater than 1000 nm, 2000 nm, 3000 nm, 4000 nm, 5000 nm, 6000 nm, 7000 nm, 8000 nm, or 9000 nm. In some aspects, the pores are spaced no more than 30000 nm, 20000 nm, or 10000 nm apart. In one aspect, the distance is at least about 10 nm, or alternatively, at least about 20 nm, 30 nm, 40 nm, 50 nm, 60 nm, 70 nm, 80 nm, 90 nm, 100 nm, 150 nm, 200 nm, 250 nm, or 300 nm. In another aspect, the distance is no more than about 1000 nm, 900 nm, 800 nm, 700 nm, 600 nm, 500 nm, 400 nm, 300 nm, 250 nm, 200 nm, 150 nm, or 100 nm.

In yet another aspect, the distance between the pores is between about 20 nm and about 800 nm, between about 30 nm and about 700 nm, between about 40 nm and about 500 nm, or between about 50 nm and about 300 nm.

The two pores can be arranged in any position so long as they allow fluid communication between the chambers and have the prescribed size and distance between them. In one aspect, the pores are placed so that there is no direct blockage between them. Still, in one aspect, the pores are substantially coaxial.

In one aspect, the device has electrodes in the chambers connected to one or more power supplies. In some aspects, the power supply includes a voltage-clamp or a patch-clamp, which can supply a voltage across each pore and measure the current through each pore independently. In this respect, the power supply and the electrode configuration can set the middle chamber to a common ground for both power supplies. In one aspect, the power supply or supplies are configured to apply a first voltage $V_1$ between the upper chamber (Chamber A) and the middle chamber (Chamber B), and a second voltage $V_2$ between the middle chamber and the lower chamber (Chamber C).

In some aspects, the first voltage $V_1$ and the second voltage $V_2$ are independently adjustable. In one aspect, the middle chamber is adjusted to be a ground relative to the two voltages. In one aspect, the middle chamber comprises a medium for providing conductance between each of the pores and the electrode in the middle chamber. In one aspect, the middle chamber includes a medium for providing a resistance between each of the pores and the electrode in the middle chamber. Keeping such a resistance sufficiently small relative to the nanopore resistances is useful for decoupling the two voltages and currents across the pores, which is helpful for the independent adjustment of the voltages.

Adjustment of the voltages can be used to control the movement of charged particles in the chambers. For instance, when both voltages are set in the same polarity, a properly charged particle can be moved from the upper chamber to the middle chamber and to the lower chamber, or the other way around, sequentially. In some aspects, when the two voltages are set to opposite polarity, a charged particle can be moved from either the upper or the lower chamber to the middle chamber and kept there.

The adjustment of the voltages in the device can be particularly useful for controlling the movement of a large molecule, such as a charged polymer scaffold, that is long enough to cross both pores at the same time. In such an aspect, the direction and the speed of the movement of the molecule can be controlled by the relative magnitude and polarity of the voltages as described below.

The device can contain materials suitable for holding liquid samples, in particular, biological samples, and/or materials suitable for nanofabrication. In one aspect, such materials include dielectric materials such as, but not limited to, silicon, silicon nitride, silicon dioxide, graphene, carbon nanotubes, $TiO_2$, $HfO_2$, $Al_2O_3$, or other metallic layers, or any combination of these materials. In some aspects, for example, a single sheet of graphene membrane of about 0.3 nm thick can be used as the pore-bearing membrane.

Devices that are microfluidic and that house two-pore microfluidic chip implementations can be made by a variety of means and methods. For a microfluidic chip comprised of two parallel membranes, both membranes can be simultaneously drilled by a single beam to form two concentric pores, though using different beams on each side of the membranes is also possible in concert with any suitable alignment technique. In general terms, the housing ensures sealed separation of Chambers A-C.

In one aspect, the device includes a microfluidic chip (labeled as "Dual-pore chip") is comprised of two parallel membranes connected by spacers. Each membrane contains a pore drilled by a single beam through the center of the membrane. Further, the device preferably has a Teflon® housing or polycarbonate housing for the chip. The housing ensures sealed separation of Chambers A-C and provides minimal access resistance for the electrode to ensure that each voltage is applied principally across each pore.

More specifically, the pore-bearing membranes can be made with transmission electron microscopy (TEM) grids with a 5-100 nm thick silicon, silicon nitride, or silicon dioxide windows. Spacers can be used to separate the membranes, using an insulator, such as SU-8, photoresist, PECVD oxide, ALD oxide, ALD alumina, or an evaporated metal material, such as Ag, Au, or Pt, and occupying a small volume within the otherwise aqueous portion of Chamber B between the membranes. A holder is seated in an aqueous bath that is comprised of the largest volumetric fraction of Chamber B. Chambers A and C are accessible by larger diameter channels (for low access resistance) that lead to the membrane seals.

A focused electron or ion beam can be used to drill pores through the membranes, naturally aligning them. The pores can also be sculpted (shrunk) to smaller sizes by applying a correct beam focusing to each layer. Any single nanopore drilling method can also be used to drill the pair of pores in the two membranes, with consideration to the drill depth possible for a given method and the thickness of the membranes. Predrilling a micro-pore to a prescribed depth and then a nanopore through the remainder of the membranes is also possible to further refine the membrane thickness.

By virtue of the voltages present at the pores of the device, charged molecules can be moved through the pores between chambers. Speed and direction of the movement can be controlled by the magnitude and polarity of the voltages. Further, because each of the two voltages can be independently adjusted, the direction and speed of the movement of a charged molecule can be finely controlled in each chamber.

One example concerns a target polynucleotide, having a length that is longer than the combined distance that includes the depth of both pores plus the distance between the two pores. For example, a 1000 by dsDNA is about 340 nm in length, and would be substantially longer than the 40 nm spanned by two 10 nm-deep pores separated by 20 nm. In a first step, the polynucleotide is loaded into either the upper or the lower chamber. By virtue of its negative charge under a physiological condition at a pH of about 7.4, the polynucleotide can be moved across a pore on which a voltage is applied. Therefore, in a second step, two voltages, in the same polarity and at the same or similar magnitudes, are applied to the pores to move the polynucleotide across both pores sequentially.

At about the time when the polynucleotide reaches the second pore, one or both of the voltages can be changed. Since the distance between the two pores is selected to be shorter than the length of the polynucleotide, when the polynucleotide reaches the second pore, it is also in the first pore. A prompt change of polarity of the voltage at the first pore, therefore, will generate a force that pulls the polynucleotide away from the second pore.

Assuming that the two pores have identical voltage-force influence and $|V_1|=|V_2|+\delta V$, the value $\delta V>0$ (or $<0$) can be adjusted for tunable motion in the $|V_1|$ (or $V_2$) direction. In practice, although the voltage-induced force at each pore will not be identical with $V_1=V_2$, calibration experiments can identify the appropriate bias voltage that will result in equal pulling forces for a given two-pore chip; and variations around that bias voltage can then be used for directional control.

If, at this point, the magnitude of the voltage-induced force at the first pore is less than that of the voltage-induced force at the second pore, then the polynucleotide will continue crossing both pores towards the second pore, but at a lower speed. In this respect, it is readily appreciated that the speed and direction of the movement of the polynucleotide can be controlled by the polarities and magnitudes of both voltages. As will be further described below, such a fine control of movement has broad applications. For quantitating target polynucleotides, the utility of two-pore device implementations is that during controlled delivery and sensing, the target polynucleotide or payload-bound target polynucleotide can be repeatedly measured, to add confidence to the detection result.

Accordingly, in one aspect, provided is a method for controlling the movement of a charged polymer scaffold through a nanopore device. The method comprises (a) loading a sample comprising a target polynucleotide (e.g., a target polynucleotide amplicon) in one of the upper chamber, middle chamber or lower chamber of the device of any of the above embodiments, wherein the device is connected to one or more power supplies for providing a first voltage between the upper chamber and the middle chamber, and a second voltage between the middle chamber and the lower chamber; (b) setting an initial first voltage and an initial second voltage so that the target polynucleotide moves between the chambers, thereby locating the polymer scaffold across both the first and second pores; and (c) adjusting the first voltage and the second voltage so that both voltages generate force to pull the charged target polynucleotide away from the middle chamber (voltage-competition mode), wherein the two voltages are different in magnitude, under controlled conditions, so that the target polynucleotide scaffold moves across both pores in either direction and in a controlled manner.

In one aspect, the sample containing the target polynucleotide is loaded into the upper chamber and the initial first voltage is set to pull the target polynucleotide from the upper chamber to the middle chamber and the initial second voltage is set to pull the target polynucleotide from the middle chamber to the lower chamber. Likewise, the sample can be initially loaded into the lower chamber, and the target polynucleotide can be pulled to the middle and the upper chambers.

In another aspect, the sample containing the target polynucleotide is loaded into the middle chamber; the initial first voltage is set to pull the charged polymer scaffold from the middle chamber to the upper chamber; and the initial second voltage is set to pull the target polynucleotide from the middle chamber to the lower chamber.

In one aspect, real-time or on-line adjustments to the first voltage and the second voltage at step (c) are performed by active control or feedback control using dedicated hardware and software, at clock rates up to hundreds of megahertz. Automated control of the first or second or both voltages is based on feedback of the first or second or both ionic current measurements.

Sensors

As discussed above, in various aspects, the nanopore device further includes one or more sensors to carry out the detection of the target polynucleotide.

The sensors used in the device can be any sensor suitable for identifying a target polynucleotide amplicon bound or unbound to a payload molecule. For instance, a sensor can be configured to identify the target polynucleotide by measuring a current, a voltage, a pH value, an optical feature, or residence time associated with the polymer. In other aspects, the sensor may be configured to identify one or more individual components of the target polynucleotide or one or more components bound or attached to the target polynucleotide. The sensor may be formed of any component configured to detect a change in a measurable parameter where the change is indicative of the target polynucleotide, a component of the target polynucleotide, or preferably, a component bound or attached to the target polynucleotide. In one aspect, the sensor includes a pair of electrodes placed at two sides of a pore to measure an ionic current across the pore when a molecule or other entity, in particular a target polynucleotide, moves through the pore. In certain aspects, the ionic current across the pore changes measurably when a target polynucleotide segment passing through the pore is bound to a payload molecule. Such changes in current may vary in predictable, measurable ways corresponding with, for example, the presence, absence, and/or size of the target polynucleotide molecule present.

In a preferred embodiment, the sensor comprises electrodes that apply voltage and are used to measure current across the nanopore. Translocations of molecules through the nanopore provides electrical impedance (Z) which affects current through the nanopore according to Ohm's Law, V=IZ, where V is voltage applied, I is current through the nanopore, and Z is impedance. Inversely, the conductance G=1/Z are monitored to signal and quantitate nanopore events. The result when a molecule translocates through a nanopore in an electrical field (e.g., under an applied voltage) is a current signature that may be correlated to the molecule passing through the nanopore upon further analysis of the current signal.

When residence time measurements from the current signature are used, the size of the component can be correlated to the specific component based on the length of time it takes to pass through the sensing device.

In one embodiment, a sensor is provided in the nanopore device that measures an optical feature of the polymer, a component (or unit) of the polymer, or a component bound or attached to the polymer. One example of such measurement includes the identification of an absorption band unique to a particular unit by infrared (or ultraviolet) spectroscopy.

In some embodiments, the sensor is an electric sensor. In some embodiments, the sensor detects a fluorescent signature. A radiation source at the outlet of the pore can be used to detect that signature.

EXAMPLES

The present technology is further defined by reference to the following example and experiments. It will be apparent to those skilled in the art that many modifications may be practiced without departing from the scope of the current invention.

Example 1: Nanopore Detection of DNA

Figure 6:
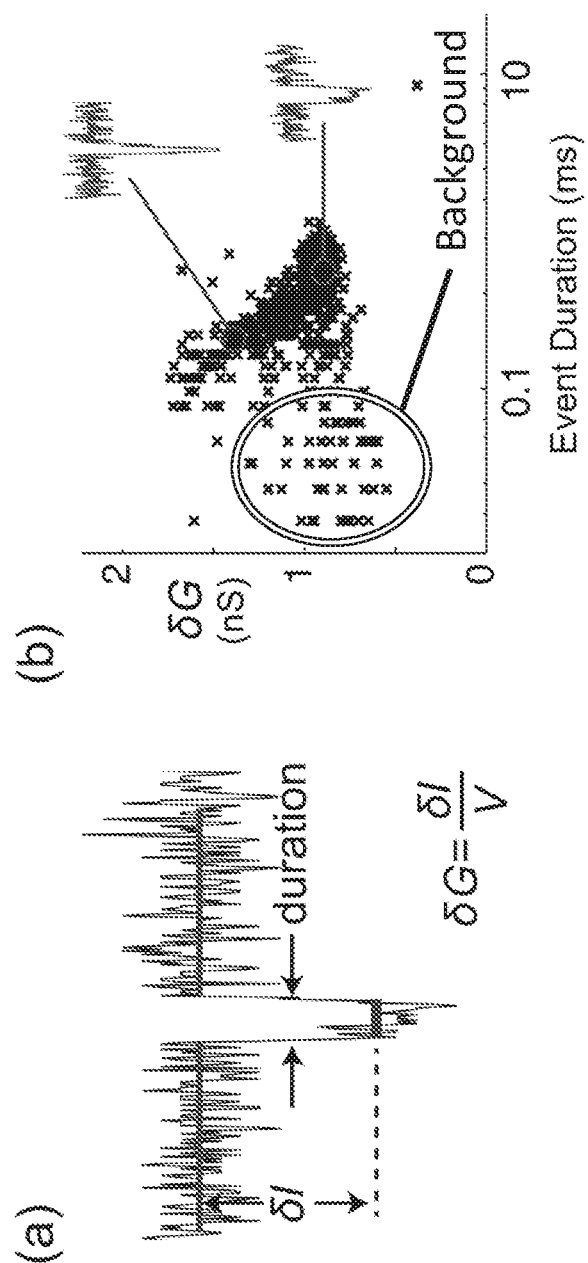
FIG. 6 shows (a) a representative nanopore current event and (b) the nanopore current event population, when detecting 3250 bp DNA with a nanopore, and discriminating polynucleotide events from background events.

A solid-state nanopore is a nano-scale opening formed in a thin solid-state membrane that separates two aqueous volumes. A voltage-clamp amplifier applies a voltage V across the membrane while measuring the ionic current through the open pore. Unlike any other single-molecule sensor, the nanopore device can be packaged into a handheld form factor at very low cost. When a single charged molecule such as a double-stranded DNA (dsDNA) is captured and driven through the pore by electrophoresis, the measured current shifts, and the conductance shift depth ($\delta G = \delta I/V$) and duration are used to characterize the event (FIG. 6a).

In some embodiments, the value $\delta G$ (also labeled $\Delta G$) is computed as the mean current shift divided by voltage. In other embodiments, the value $\delta G$ (also labeled $\Delta G$) is computed as the maximum current shift divided by voltage. Commonly, the duration is computed as the shift width.

After recording many events during an experiment, distributions of the events are analyzed to characterize the corresponding molecule. FIG. 6b shows the event characteristics for 0.1 nM of 3.2 kb dsDNA passing through an 27 nm diameter nanopore at voltage V=100 mV (1M LiCl), producing 744 events recorded in 10 minutes. The two encircled representative events show: a wider and shallower event corresponding to the DNA passing through unfolded; and a faster but deeper event corresponding to the DNA passing through folded. For dsDNA that is ~1 kb and shorter, the DNA passes through the pore only in an unfolded state.

It is common in nanopore experiments for electrical noise spikes to generate false-events (an electrical "background noise"). These false events are faster and shallower than the 3.2 kb events, and thus are easy to discriminate. Background events 1-2 per minute are commonly observed with buffer only, due to transient capacitive changes in the membrane, creating fast (<0.1 ms) shallow (<1.5 nS) events. When using shorter DNA, as detailed in the following examples, background electrical noise false events are difficult to separate from true DNA events, therefore making it difficult to separate true events from false events. While nanopores smaller than 5 nm can make it possible to separate DNA true events from noise false events (Briggs, Kyle, Harold Kwok, and Vincent Tabard-Cossa. "Automated Fabrication of 2-Nm Solid-State Nanopores for Nucleic Acid Analysis." *Small* 10, no. 10 (May 28, 2014): 2077-86. doi:10.1002/sm11.201303602), such pores are likely to clog when other background molecule types (e.g., from sample, or PCR reaction mixtures, or unbound payload molecules) are present even in low abundance. This is because many of the background molecules are equal or larger than 5 nm in size (e.g., monostreptavidin protein acting as a payload is ~5 nm), and therefore can be captured into the pore but cannot pass through the pore when it is 5 nm or smaller. To be tolerant to such background molecules of varying types, we favor pores that are at least 5 nm in diameter. As a consequence, shorter amplicons (e.g., 500 bp or smaller) require a payload attachment to make them sufficiently observable in the (larger) nanopore for quantitation to be possible. On the other hand, amplicons larger than 500 bp (e.g., 1 kb) can be quantitated with larger pores (at least 10 nm and up to 50 nm in diameter) without payload attachment, and in the presence of varying types of background, including from sample (cheek swab, whole blood) and PCR reaction mixtures at varying dilutions.

Example 2: Amplicon Generation and Payload-Attachment Methods

The examples that follow that utilize payload-bound DNA use the following amplicon lengths: 500 bp DNA, 470 bp DNA (comprising the SRY gene), and 362 bp DNA (comprising the SMCY gene).

The SRY (sex determining region Y) gene is located on the Y-chromosome and is therefore unique to males. Lack of the SRY gene (or, more precisely, regions of it) is a common reason for male infertility (Abusheikha, N., A. Lass, and P. Brinsden. "XX males without SRY gene and with infertility: Case report." *Human Reproduction* 16.4 (2001): 717-718) or other health conditions (e.g. Swyer syndrome). Thus, a polymerase chain reaction (PCR) assay can be designed to amplify the portion of the SRY gene that is lacking in sterile males, providing a test for maleness and candidate infertility. If the amplicon is produced, the sample came from a male and contains said region of the SRY gene.

Amplification of a 470 basepair section of the SRY gene was accomplished by mixing a buccal swab from a fertile male with 50 µl of a PCR reaction mixture that contained 1× Terra Direct Buffer (p/n 639287), 0.3 µM SRY forward primer (GAATATTCCCGCTCTCCGGA (SEQ ID NO: 1)), 0.3 µM SRY reverse primer (GCTGGTGCTCCATTCTTGAG (SEQ ID NO: 2)), and 1 µl of PCR Direct Polymerase Terra 639287). This reaction mixture was subjected to a 6 step PCR protocol as follows: 1) 98 C for 2 mins, 2) 98 C for 10 sec, 3) 60 C for 15 sec, 4) 68 C for 1 min, 5) repeat steps 2-4 for 40 cycles, 6) hold at 4 C. To incorporate biotin at the 5' and/or 3' terminal ends of the molecule, primers biotinylated at the 5' end were used in the reaction mixture. This same reaction was also performed using 2 ul of a 1:1000 dilution of a blood drop as starting sample material. To test against non-specific amplification as a negative control, water or a women buccal swab was used as a sample input with the expectation that no product would be generated.

The SMCY gene is located on the Y-chromosome and is therefore unique to males. Loss of SMCY is observed in prostate cancer, and with increasing frequency as the cancer progresses (PERINCHERY, GEETHA, et al. "Deletion of Y-chromosome specific genes in human prostate cancer." *The Journal of urology* 163.4 (2000): 1339-1342).

Amplification of the SMCY gene was accomplished using the exact same protocol described above, but with SMCY gene specific primers (forward primer CCTCCAGACCTGGACAGAAT (SEQ ID NO: 3), reverse primer TGTGGTCTGTGGAAGGTGTCA (SEQ ID NO: 4)). This generated a 362 basepair amplicon.

Post thermocycling, biotinylated DNA (for SRY and SMCY) was tagged with monostreptavidin payload or anti-biotin antibody payload by adding approximately 10-fold excess of payload to available biotin molecules. To establish how much biotinylated DNA (for SRY and SMCY) is generated during an amplification reaction, separate experiments were performed in which PCR product was purified out of PCR reaction mix and quantitated using spectrophotometry.

Figure 8:
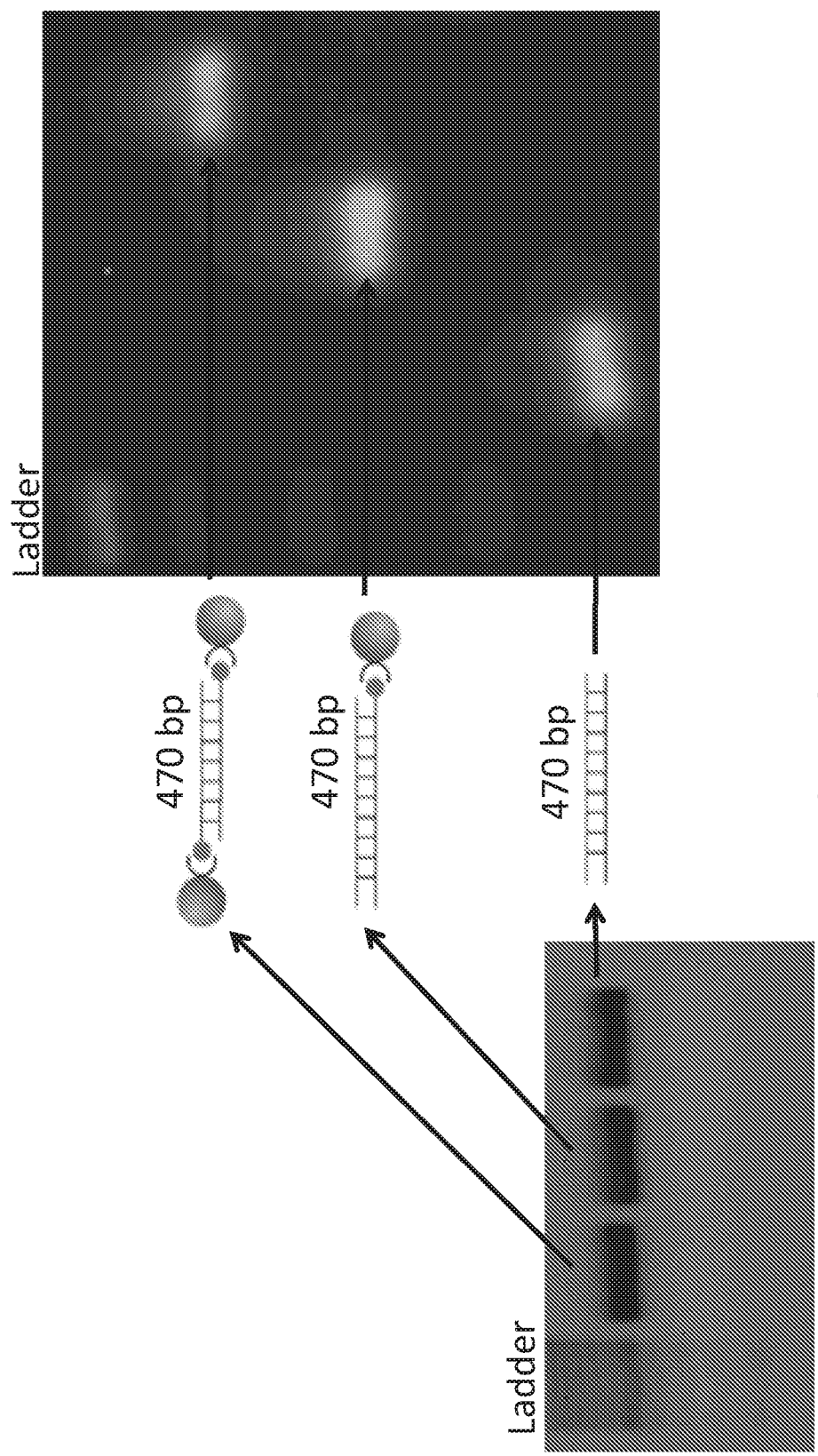
FIG. 8 shows an agarose gel (left) of 470 bp DNA amplified with no primer modifications, with 1 biotin-modified primer, and 2 biotin-modified primers, followed by an agarose gel (right) after monostreptavidin payload attachment.

Consistency in amplification from multiple reactions was demonstrated by running 2% agarose gel with 5 µl of separate PCR reaction products (FIG. 8, left image). Subsequently, incubation with monostreptavidin protein (10× to biotin sites) was performed for attaching the payloads (none, one or two). To confirm PCR product is efficiently bulked by 1 (if one biotin modified primer was used) or 2 (if 2 modified primers were used) monostreptavidin proteins, a 2% agarose gel was run (FIG. 8, right image) for the blood drop source material. Negative control using a female cheek swab as starting material was also verified by running a gel, which produced no observable band (not shown).

Figure 11:
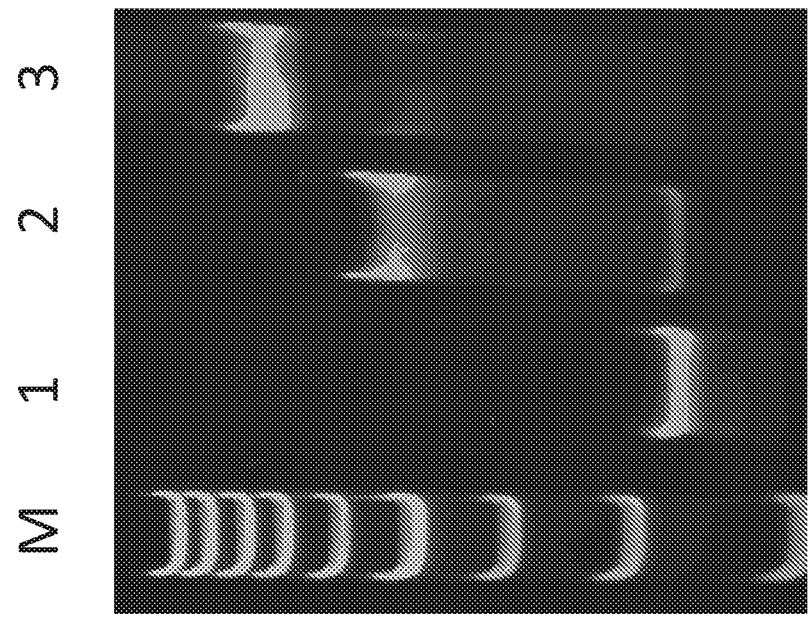
FIG. 11 shows an agarose gel of (1) 470 bp DNA amplified with no primer modifications, (2) DNA with 1 biotin-modified primer, and (3) DNA with 2 biotin-modified primers, after anti-biotin antibody payload attachment.
Figure 15:
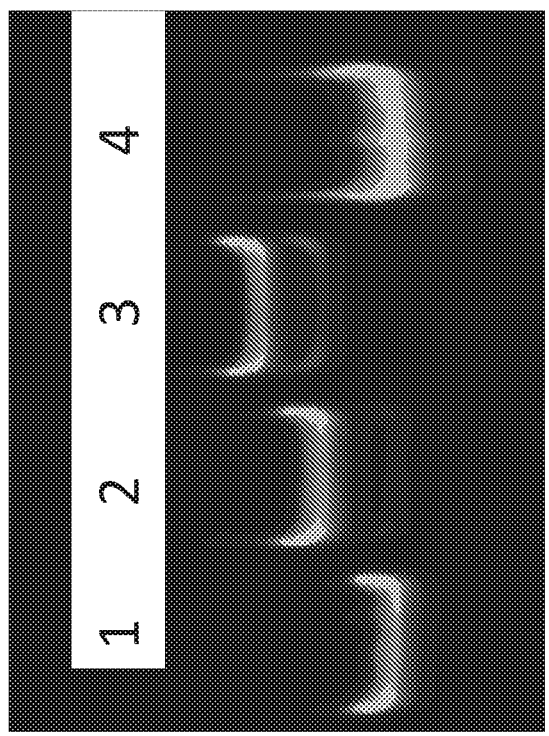
FIG. 15 shows an agarose gel of (1,4) 470 bp DNA (no biotin primer modification), (2) 470 bp DNA-[1 biotin]-[1 monostreptavidin], and (3) 470 bp DNA-[2 biotin]-[2 monostreptavidin], with lanes 1-3 in the presence of 20× excess monostreptavidin showing non-specific payload attachment is absent.

From the buccal swab source material used to generate SRY amplicons, reagents were electrophoresed in a 5% polyacrylamide gel for 80 min at 150 V. The DNA was then stained using a 1× solution of Sybr Green DNA specific fluorescent dye (7.5 ul sample+1.5 ul dye) and imaged using UV light. "M" in all gels, where shown, indicates a 100 bp sizing marker to track the DNA. FIG. 11 shows SRY amplicons run in the following order, lane 1) SRY amplicon, lane 2) SRY amplicon with 1 anti-biotin antibody payload attached, 3) SRY amplicon with 2 anti-biotin payloads attached. Minor lower bands in lanes 2 and 3 indicated SRY with no payload and one payload, respectively. Another gel (FIG. 15) compared SRY with no primer modifications (lane 1) with one biotinylated primer (lane 2) and two biotinylated primers (lane 3) all in the presence of 20× monostreptavidin, showing specificity of the binding reaction (lane 4 is SRY absent monostreptavidin)

Figure 20:
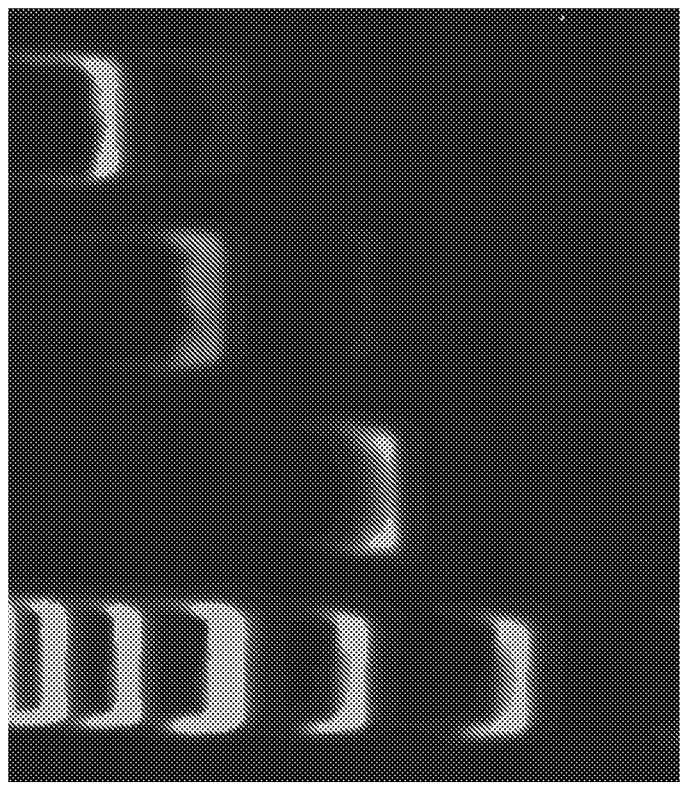
FIG. 20 shows an agarose gel of (1) 362 bp DNA (no biotin primer modification), (2) 362 bp DNA-[1 biotin]-[1 monostreptavidin], and (3) 362 DNA-[2 biotin]-[2 monostreptavidin].

From the buccal swab source material used to generate SMCY amplicons, 5 µl (approximately 100 ng DNA) of PCR reaction was electrophoresed in a 5% polyacrylamide gel for 80 min at 150 V. FIG. 20 shows SMCY amplicons run in the following order, lane 1) SMCY amplicon, lane 2) SMCY amplicon with 1 monostreptavidin payload attached, lane 3) SMCY with 2 monostreptavidin payloads attached.

Post thermocycling and payload attachment (if applicable), samples are diluted into recording buffer resulting in a final SRY or SMCY concentration of 0.1 nM to 1 nM in 1 M LiCl, 10 mM Tris-HCl, 1 mM EDTA, pH 7.5.

Example 3: SRY Gene Detection

Figure 7:
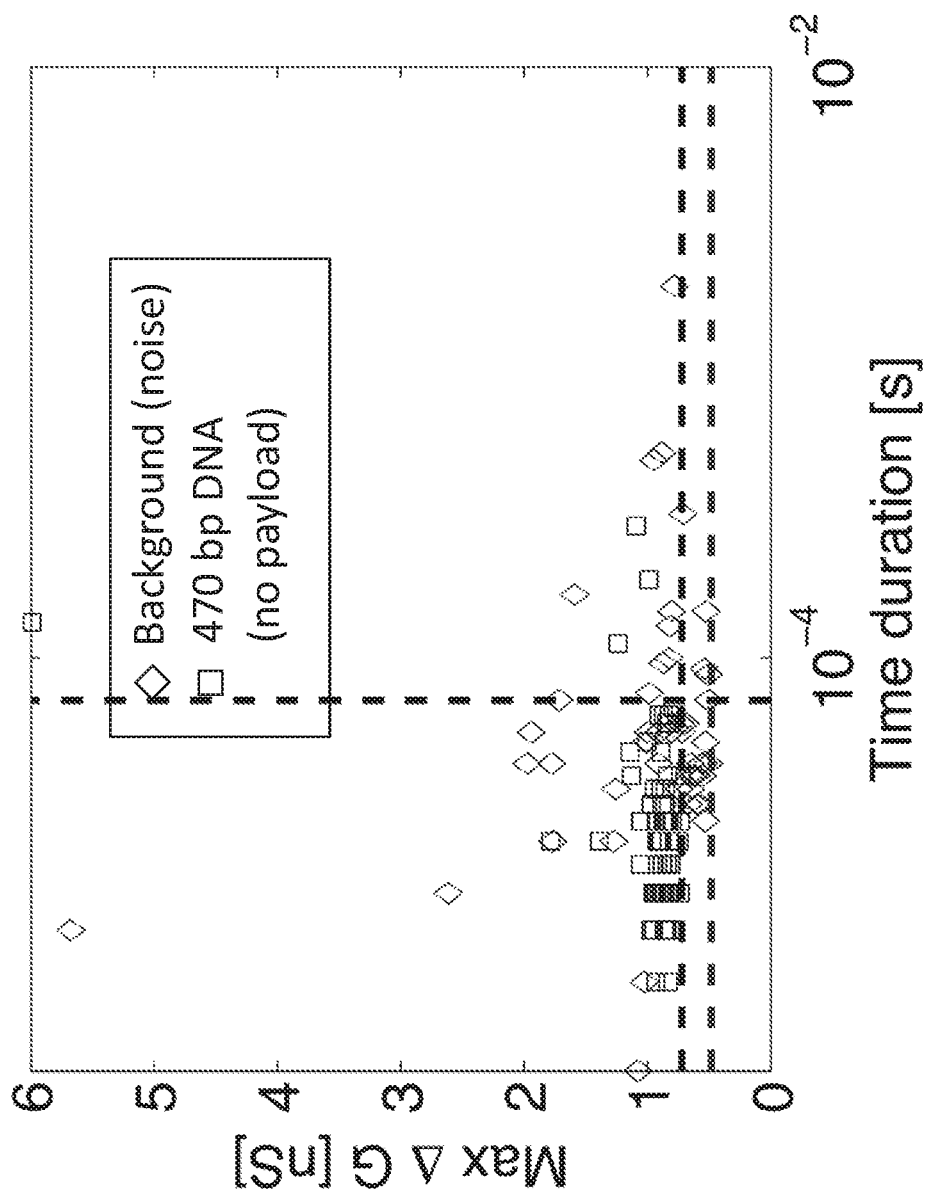
FIG. 7 shows data comparing 470 bp DNA events with background noise events, showing the two could not be discriminated.

SRY amplicon events without payloads attached and electrical noise background false-events are indistinguishable, making the assay too susceptible to false positives. In particular, FIG. 7 shows an event plot of maximum shift vs. duration of individual molecules passing through the pore (100 mV), comparing SRY amplicons with no payload (black) with electrical background events (red). Although the SRY is at 1 nM (a high concentration), most events are missed, and here produced only 3.5 detected events per minute (69 events, over 20 minutes). This overlaps in event rate and distribution with the background event population (47 events, 75 min). Inference of concentration from capture rate is impossible with this inability to detect most DNA events, and inability to discriminate from background. The experiment used a 20 nm pore in a 15 nm membrane.

Figure 9:
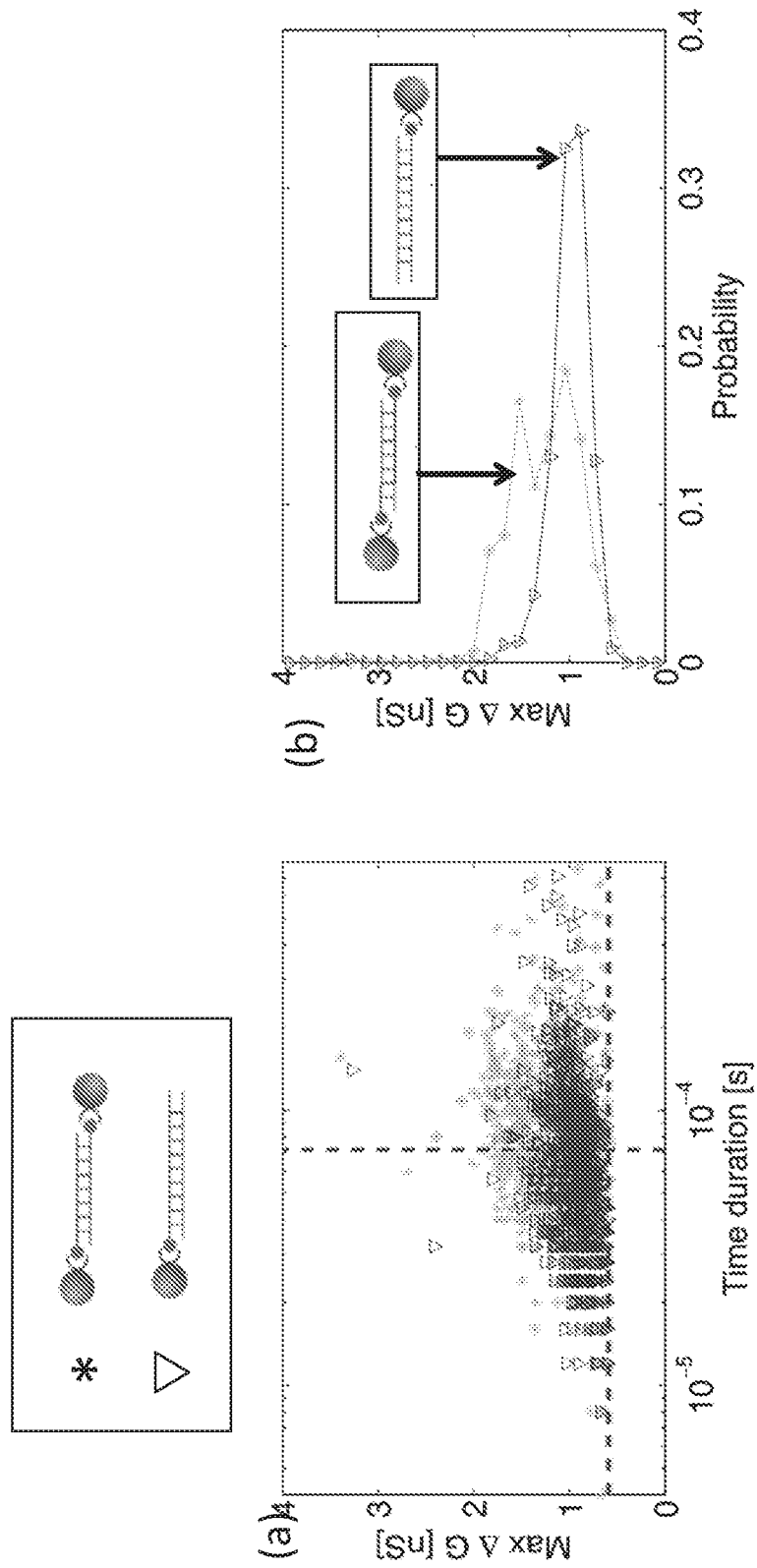
FIG. 9 compares the nanopore current event populations for 470 bp DNA-[1 biotin]-[1 monostreptavidin] and 470 bp DNA-[2 biotin]-[2 monostreptavidin]

One the other hand, SRY amplicons with one and two monostreptavidin protein payloads attached (SRY-1MS and SRY-2MS, respectively) were clearly distinguishable from electrical noise background false-events, by the increase in event rate and in a clearer event distribution that is not produced by noise events. In particular, after gel proofing the payload-attached SRY molecules (FIG. 8), the reagents were tested sequentially on the same nanopore shown in FIG. 7, producing the event distribution plot of maximum shift vs. duration in FIG. 9a. The maximum shift event histogram is shown in FIG. 9b. The SRY-1MS complexes produced 1074 events over 45 minutes, with the percentage of events longer than 0.072 ms at 41.5% (446). The SRY-2MS complexes produced 937 events over 80 minutes, with the percentage of events longer than 0.072 ms equal to 43.9% (411). By comparison, the noise false-events reported 28% longer than 0.072 ms. Additionally, the SRY events without a payload produced only 4.4% of events longer than 0.072 ms.

By applying the framework established in the section "Assigning Statistical Significance to Detection," we can assign statistical confidence to detecting the 1 and 2 payload-bound SRY amplicons. Specifically, background events are considered type 1 and DNA-payload events are considered type 2. An example criterion is to tag an event as type 2 if it is longer than 0.072 ms. The background noise false-positive events can be used to compute q1=0.28 (28%).

The DNA-payload results can be used as a mock detection experiment and to determine if type 2 molecules are present by applying equation (1) of the mathematical framework. For SRY-1MS as the type 2 molecule, the result is $Q(p)-Q_{sd}(p)=0.415-0.037=0.38>0.28$, which means we can say that SRY-1MS molecules are present with 99% confidence. For SRY-2MS as the type 2 molecule, the result is $Q(p)-Q_{sd}(p)=0.439-0.04=0.40>0.28$, which means we can say that SRY-2MS molecules are present with 99% confidence. On the other hand, the SRY event population does not satisfy the criteria in equation (1), and so we cannot say with 99% confidence the SRY molecules are present above background.

Figure 10:
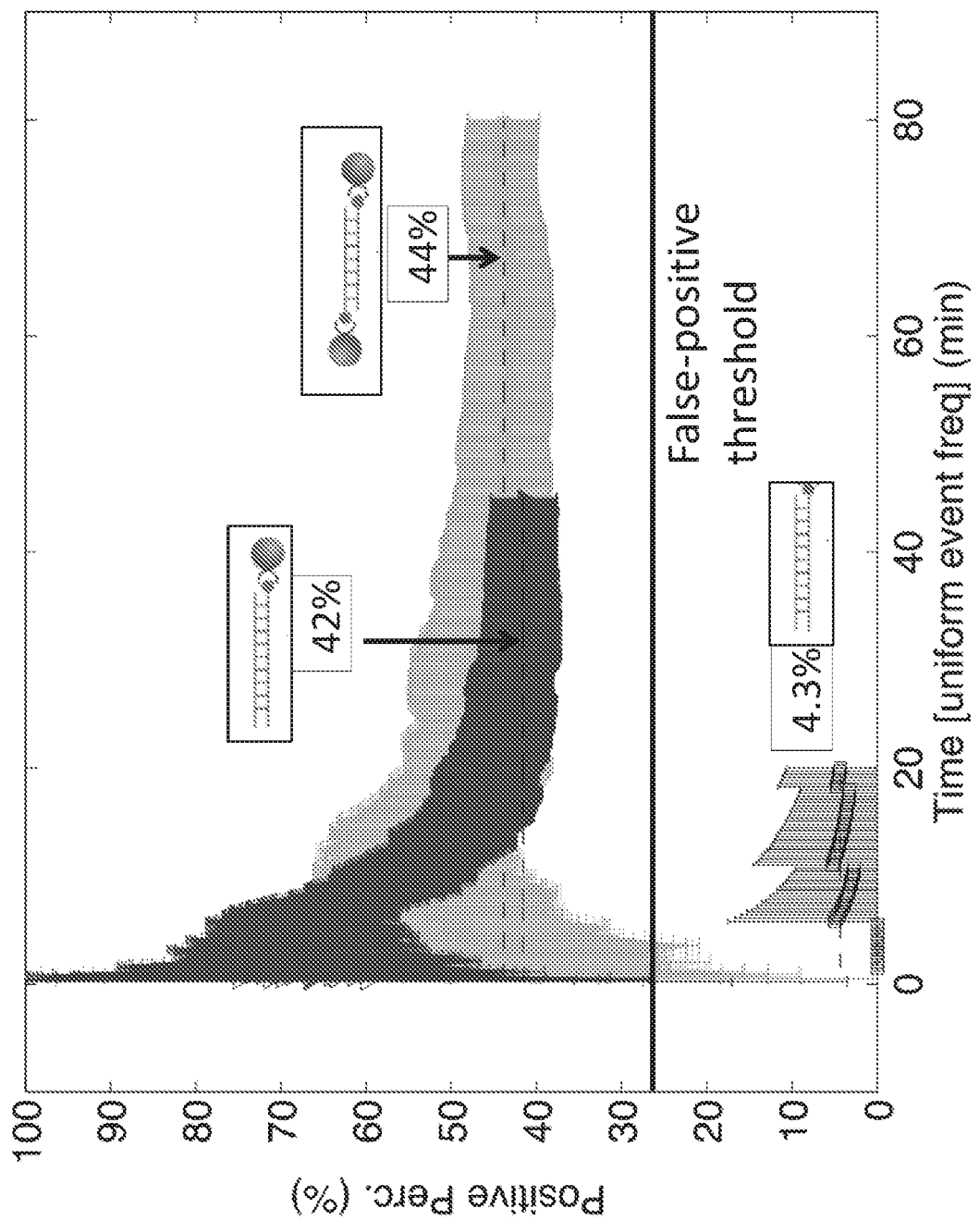
FIG. 10 compares the Positive Percentage detection criteria for 470 bp DNA, 470 bp DNA-[1 biotin]-[1 monostreptavidin] and 470 bp DNA-[2 biotin]-[2 monostreptavidin], against the false-positive threshold established from background (electrical noise) events.

A plot of $Q(p) \pm Q_{sd}(p)$ as a function of recording time is shown for each reagent type (SRY, SRY-1MS, SRY-2MS) in FIG. 10. The trends are also compared to the false-positive threshold established from the background false-positive events. Observe too that the SRY-1MS and SRY-2MS are detected with 99% confidence within the first 5 minutes of recording.

The example criterion of tagging an event as type 2 is if the event duration is longer than 0.072 ms, which yielded positive detection results for both payload-attached SRY molecule types. This result is also maintained while varying the threshold duration value, showing that the result is not dependent on a unique or narrow criteria value range. The same detection result is upheld if the event duration is any value between 0.02 to 0.1 ms.

Additionally, different criteria can be used and the detection result is still preserved. Specifically, consider the criterion of tagging an event as type 2 if max $\delta G>1$ nS. The background noise false-positive events can be used to compute q1=0.23 (23%). With this criterion, for SRY-1MS as the type 2 molecule, the result is $Q(p)-Q_{sd}(p)=0.333-0.037=0.29>0.23$, which means we can say that SRY-1MS molecules are present with 99% confidence. For SRY-2MS as the type 2 molecule, the result is more pronounced since these molecules with 2 payload produce a larger number of deeper events. Specifically, $Q(p)-Q_{sd}(p)=0.581-0.041=0.54>0.23$, which means we can say that SRY-2MS molecules are present with 99% confidence. As before, the SRY event population does not satisfy the criteria in equation (1) (since Q(p)=0.13), and so we cannot say with 99% confidence the SRY molecules are present above background.

The results with the max $\delta G>1$ nS criteria suggest that this criteria could also be used to detect SRY-2MS molecules above a background that includes SRY-1MS molecules. That is, if an assay first used a single MS payload to detect a 1MS-bound target, and subsequently tested for a double MS payload product, the max $\delta G>1$ nS criteria could be used to determine if the 2MS-bound target is present. This provides a form of multiplexing. For this data set, if SRY-1MS is a form of background, then q1=0.333 in the application of equation (1). Since $Q(p)-Q_{sd}(p)=0.581-0.041=0.54>0.333$, we can say that SRY-2MS molecules are present with 99% confidence above a background than includes SRY-1MS molecules.

Example 4: SRY Gene Detection in a Larger Nanopore with a Larger Payload

Figure 12:
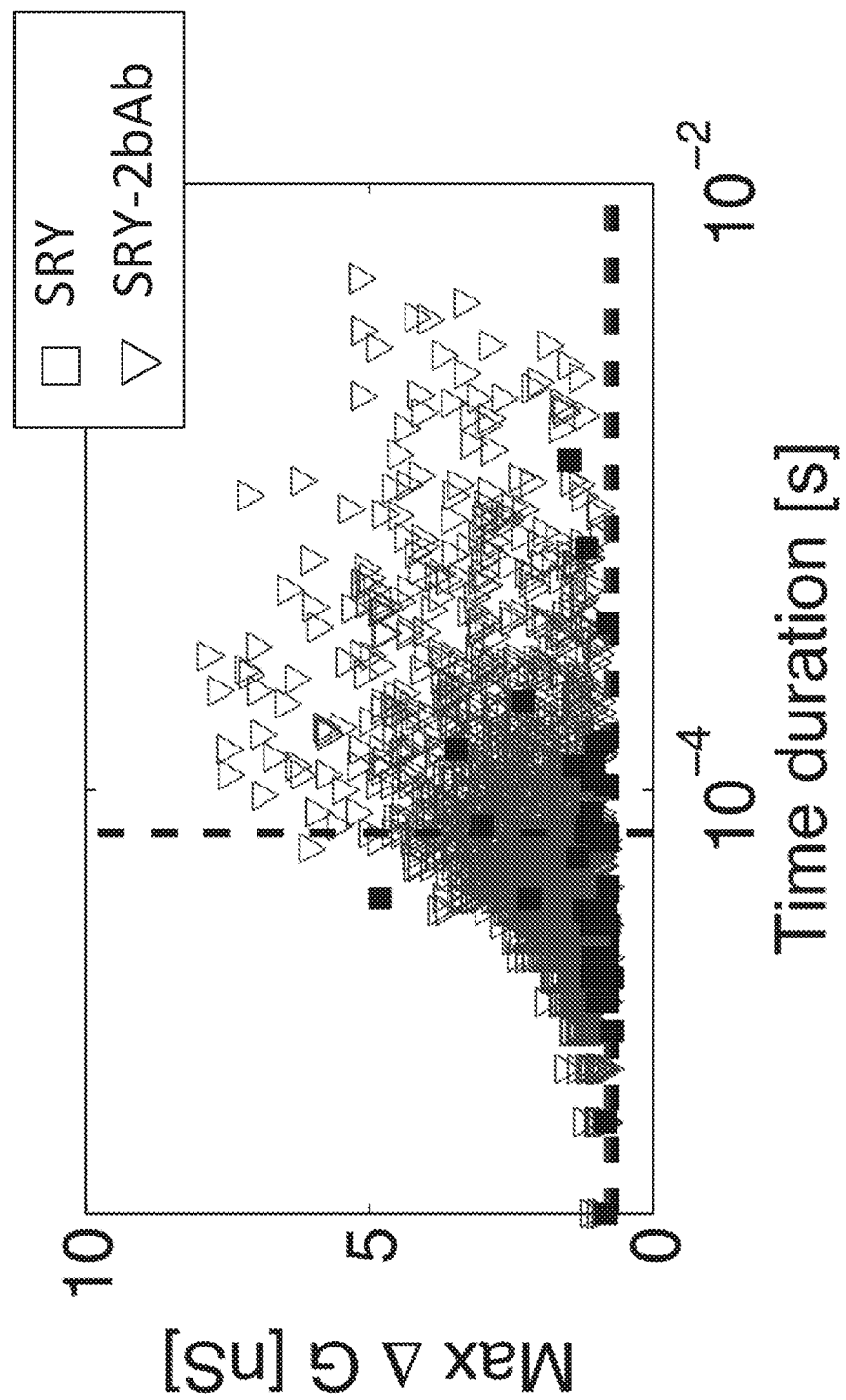
FIG. 12 compares the nanopore current event populations for 470 bp DNA (no payload) with 470 bp DNA-[2 biotin]-[2 anti-biotin antibody].

The following data demonstrates the method of "bulking" amplicons using primers that contain a chemical modification (biotin) and the "bulking" payload is an antibody. Gel images demonstrated confidence in 1 and 2 payload-bound SRY molecules (FIG. 11). The anti-biotin antibody (bAb) is roughly 3× larger (150 kDa) than monostreptavidin (66 kDa), providing a larger payload. With the larger payload, we anticipated and the data showed that the Ab-bound SRY events would have a deeper impedance shift than observed for MS-bound SRY. As an example, the percentage of SRY-2MS events deeper than 1.5 nS is 16.0085% (150/937) and with a 20 nm pore. By comparison, the percentage of SRY-2bAb events deeper than 1.5 nS is 60.023% (1042/1736), and this with a 2× larger pore (45 nm diameter pore, 30 nm membrane). By contrast, SRY without a payload produced only 41 events in 30 min, with only 12.2% of events deeper than 1.5 nS. FIG. 12 shows the event plot of maximum $\delta G$ vs. duration of individual molecules passing through the pore for SRY without a payload (black) and SRY-2bAb (pink). Therefore, larger payloads provide deeper event signatures, and make detection (with 99% confidence) possible even with larger nanopores.

Example 5: Discriminating Amplicons from PCR Background

Figure 13:
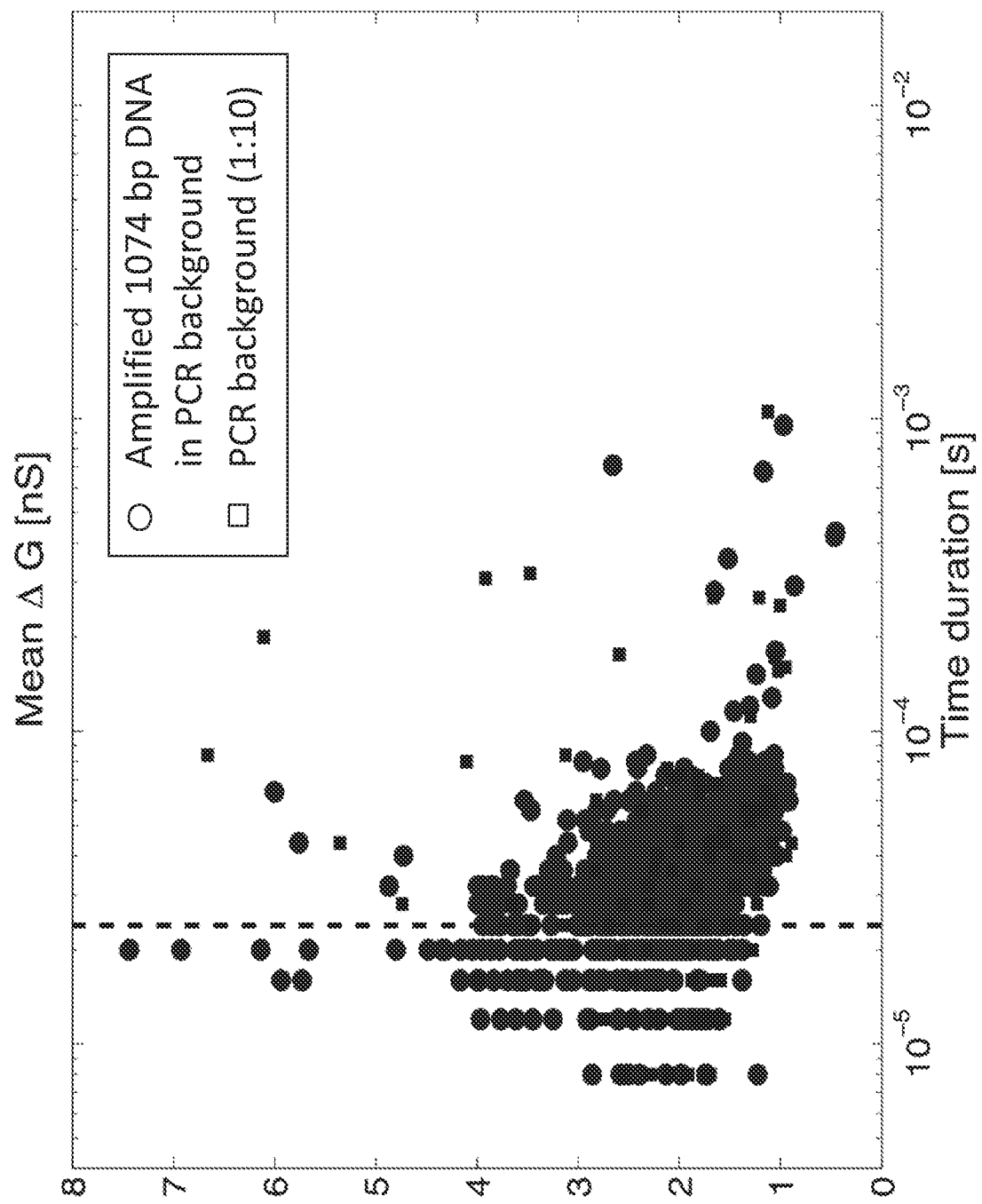
FIG. 13 compares the nanopore current event populations for PCR background at 1:10 dilution versus amplified 1074 bp DNA in the same PCR background.
Figure 14:
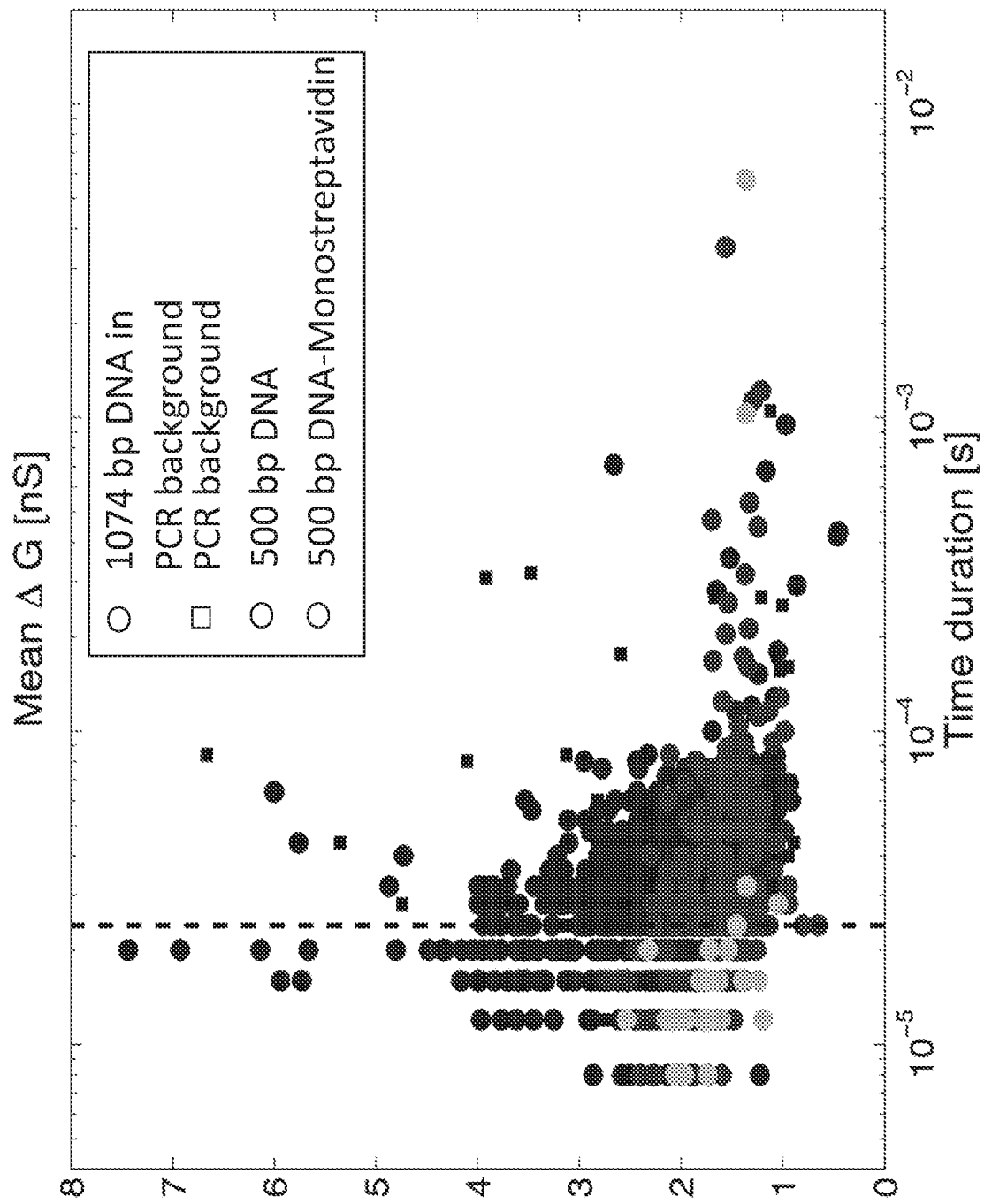
FIG. 14 compares the nanopore current event populations for PCR background at 1:10 dilution, amplified 1074 bp DNA in the same PCR background, amplified 500 bp DNA without a payload, and amplified 500 bp DNA-[1 biotin]-[1 monostreptavidin].

The following example demonstrates that PCR amplicons can be discriminated from background events due to PCR reaction mixture in one of two ways: by using an amplicon of a length at least 1000 bp in length (FIG. 13), or by adding payload (FIG. 14).

FIG. 13 shows an event distribution plot for 1074 bp amplicons at 0.7 nM in the presence of PCR background (blue), and PCR background alone (black) using a 25 nm pore in 22 nm membrane. The 1:10 dilution of PCR background was used in both cases. Dilution can be controlled such that background event rate not too large compared to the expected amplicon rate. With more appreciable and disperse events due to background from PCR, the detectable event rate of the target sequence compared to background becomes the discriminating factor. Since the amplicon is long enough here, detection is viable.

The 0.7 nM of 1074 bp DNA was achieved after 15 cycles of PCR (808 pg of template using a 5.6 scaffold), diluted 1:10 into recording buffer without purification, and produced 1502 events over 10 minutes (2.5 1/sec). The PCR background produced 97 events over 10 minutes (0.17 1/sec). The PCR reaction mixture measured was produced using a reaction that had water instead of template (equivalent volume of water as would have been used if template was added), likewise cycled 15 times, then diluted 1:10 into recording buffer.

PCR background includes non-hybridized primers, dNTPs (deoxynucleotide triphosphates, dATP, dGTP, dCTP, dTTP), polymerase enzyme (e.g. Taq or Pfu), salts (Magnesium chloride, Magnesium Sulfate, Ammonium sulfate, sodium chloride, potassium chloride), BSA (bovine serum albumin-stabilizer), detergent (triton X-100), among other elements that could be present depending on the amplification protocol used.

FIG. 14 shows conceptually how shorter amplicons required payload-attachment in order to be detectable above PCR reaction mixture background. Specifically, 0.2 nM 500 bp amplicon events without (green) and with (red) 1MS payload (single primer has biotin modification at 5' end) are overlayed on the data from FIG. 13. Without a payload, the event rate of DNA without a payload is not appreciable enough (29 events over 30 minutes) compared to PCR background, with most DNA passing through the sensor undetected. With a payload (500 bp-MS), on the other hand, the event rate is appreciable enough for detection (238 events, over 18 minutes), and can be discriminated from background with statistical confidence by identifying a detection criterion around a subset of events enclosed by the DNA-payload event population. Assessing statistical confidence for discrimination of amplicons above PCR background is the focus of the following examples.

Example 6: SRY Gene Detection in Presence of PCR Background

Figure 16:
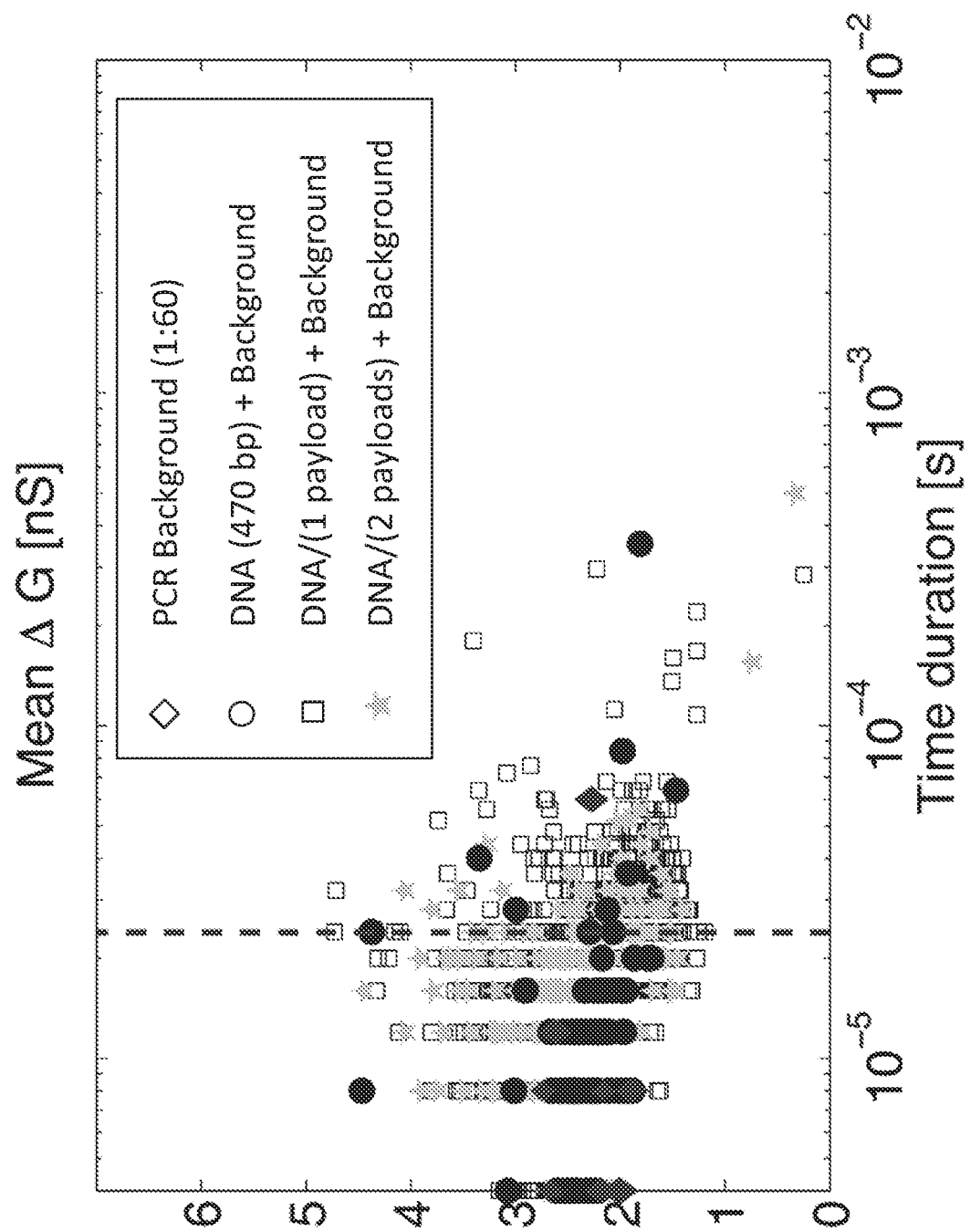
FIG. 16 compares the nanopore current event populations for PCR background alone (1:60 dilution), with 470 bp DNA (no payload), 470 bp DNA-[1 biotin]-[1 monostreptavidin] and 470 bp DNA-[2 biotin]-[2 monostreptavidin] in the presence of PCR background (1:60 dilution).
Figure 17:
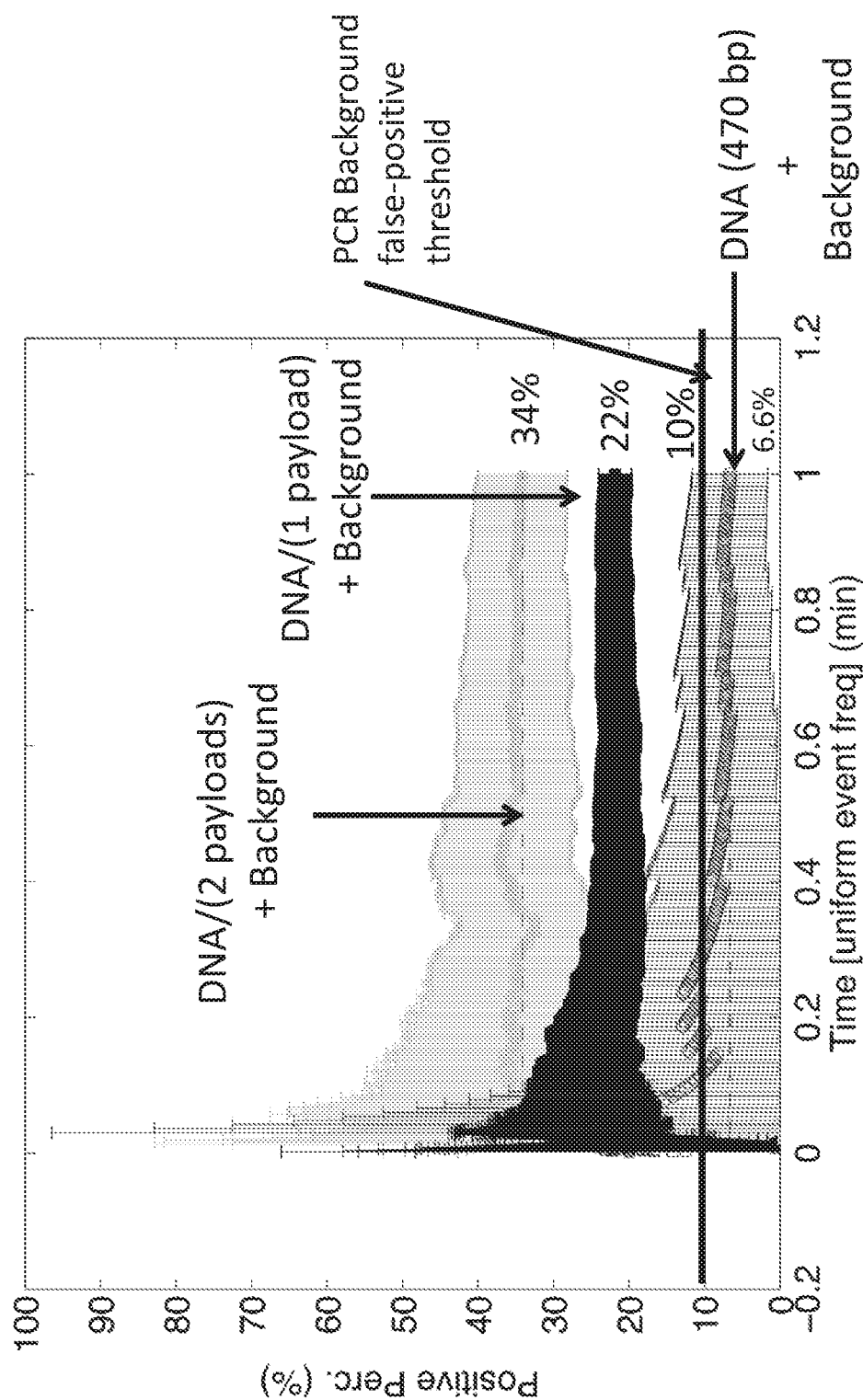
FIG. 17 compares the Positive Percentage detection criteria for 470 bp DNA, 470 bp DNA-[1 biotin]-[1 monostreptavidin] and 470 bp DNA-[2 biotin]-[2 monostreptavidin], against the false-positive threshold established from background events (PCR background 1:60 dilution).

FIGS. 16 and 17 show that SRY-1MS and SRY-2MS can be detected with 99% confidence in the presence of 1:60 dilution of PCR background, whereas SRY alone cannot be discriminated from the PCR background. These results were obtained using a 20 nm pore in 15 nm membrane (100 mV). FIG. 16 shows the event plot of mean $\delta G$ vs. duration of individual molecules passing through the pore, for PCR background alone (red), SRY without a payload (blue), SRY-1MS (black) and SRY-2MS (cyan), with all SRY reagents tested in the presence of 1:60 dilution of PCR background. The PCR background alone produced 10 events in 40 minutes, comparable to the SRY (no biotin, no payload) 73 events in 20 minutes. Although the SRY event rate is modestly higher than background, the event populations overlap too much to be able to detect SRY with confidence. As an example, PCR background and SRY had 10% and 4%, respectively, of events longer than 0.072 ms. By contrast, payload-bound SRY events at 0.5 nM had a significantly higher capture rates, since these molecules are made more observable by virtue of the payload. SRY-1MS produced 1769 events in 34 min, and SRY-2MS produced 326 events in only 6 min. We can also apply the mathematical framework presented to achieve 99% confidence of detection for both of these payload-bound amplicons, as detailed next.

Visually, the event plot in FIG. 16 suggests that the payload-bound events produce a higher percentage of deeper events. From this, we can choose a criterion based on event depth. Specifically, consider the criterion of tagging an event as type 2 if mean $\delta G > 2.7$ nS. The PCR background false-positive events can be used to compute $q1=0.1$ (10%). With this criterion, for SRY-1MS as the type 2 molecule, the result is $Q(p)-Q_{sd}(p)=0.22-0.025=0.19>0.1$, which means we can say that SRY-1MS molecules are present with 99% confidence. For SRY-2MS as the type 2 molecule, the result is more pronounced since these molecules with 2 payload produce a larger number of deeper events. Specifically, $Q(p)-Q_{sd}(p)=0.34-0.067=0.27>0.1$, which means we can say that SRY-2MS molecules are present with 99% confidence. As before, the SRY event population does not satisfy the criteria in equation (1) (since $Q(p)=0.066$), and so we cannot say with 99% confidence the SRY molecules are present above background.

A plot of $Q(p) \pm Q_{sd}(p)$ as a function of recording time is shown for each reagent type in the presence of PCR background at 1:60 dilution in FIG. 17, with normalization of time on the horizontal axis due to the large differences in recording times. The trends are also compared to the false-positive threshold established from the PCR background false-positive events. Both the SRY-1MS and SRY-2MS are detected with 99% confidence within the first 60 seconds of recording.

Example 7: SRY Gene Detection in Presence of PCR and Whole Blood Background

Figure 18:
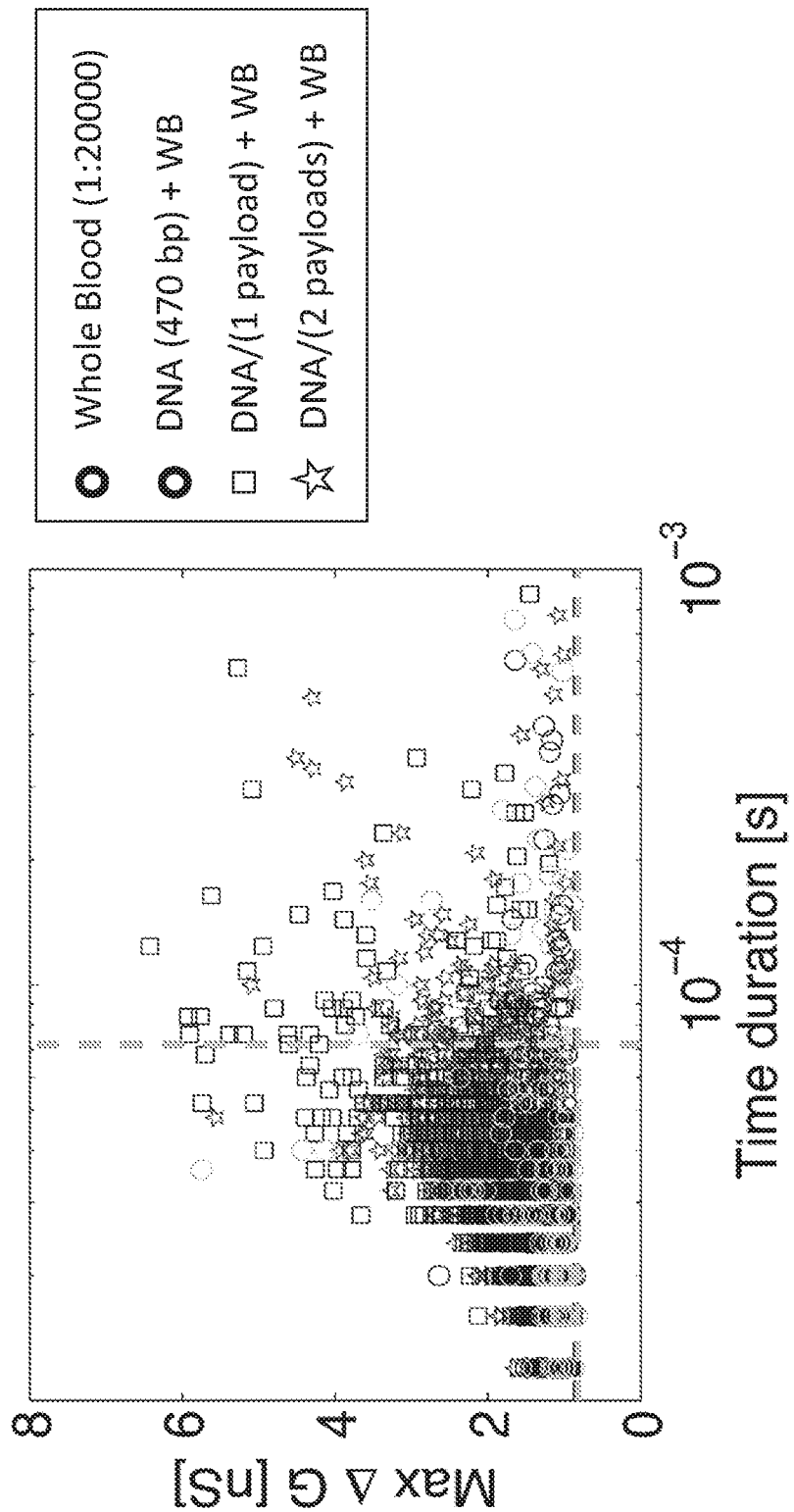
FIG. 18 compares the nanopore current event populations for whole blood background alone (1:20000 dilution), with 470 bp DNA (no payload), 470 bp DNA-[1 biotin]-[1 monostreptavidin] and 470 bp DNA-[2 biotin]-[2 monostreptavidin] in the presence of whole blood background (1:20000 dilution).
Figure 19:
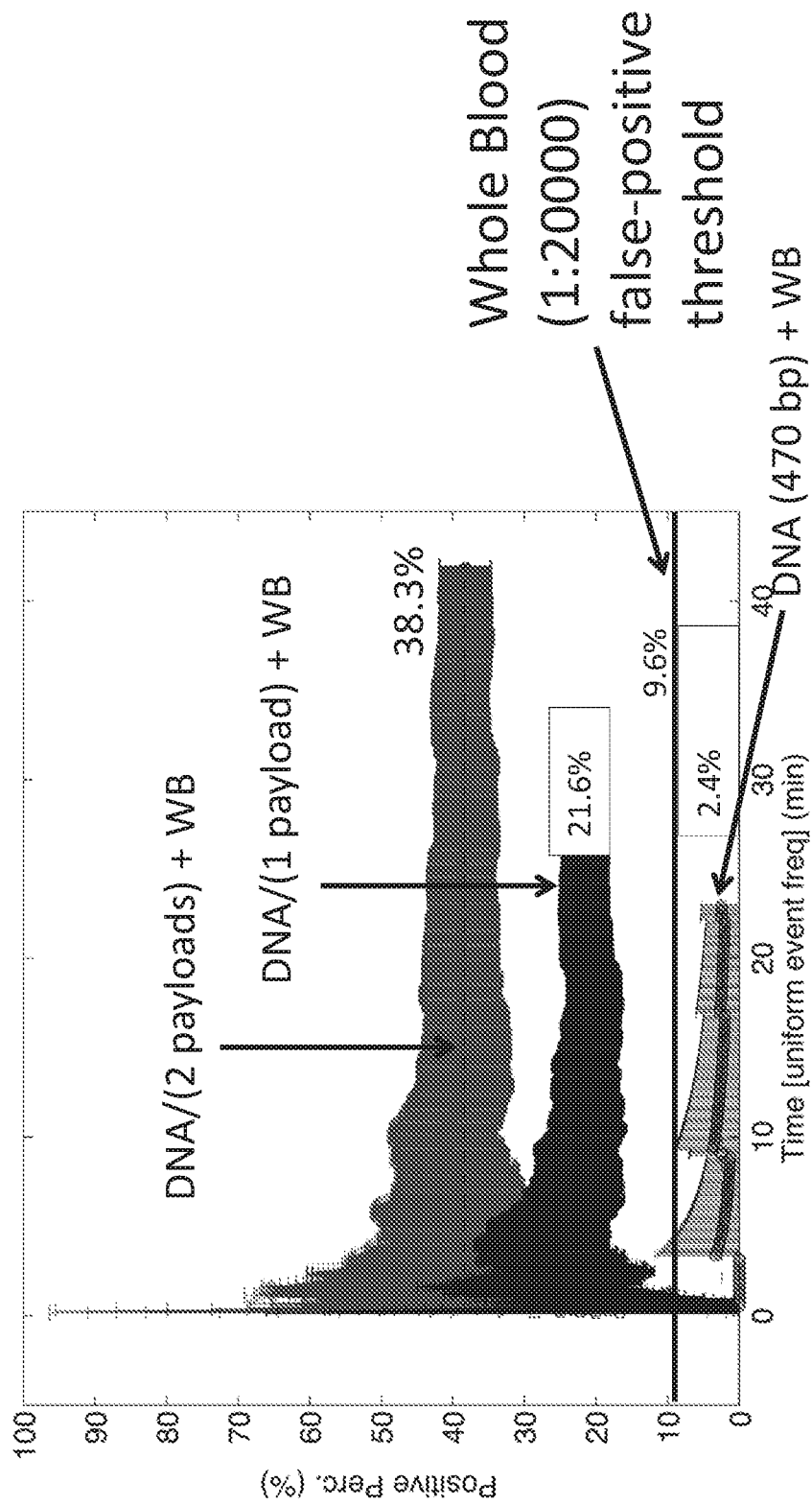
FIG. 19 compares the Positive Percentage detection criteria for 470 bp DNA, 470 bp DNA-[1 biotin]-[1 monostreptavidin] and 470 bp DNA-[2 biotin]-[2 monostreptavidin], against the false-positive threshold established from background events (whole blood background 1:20000 dilution).

FIGS. 18 and 19 show that SRY-1MS and SRY-2MS can be detected with 99% confidence in the presence of two forms of background in concert: the first is in the form of a mock "sample" (a 1:20000 dilution of whole blood), and the second is a 1:100 dilution of PCR reaction reagents used to produce the amplicons. As in other cases considered above, SRY alone cannot be discriminated from this form of background. These results were obtained using a 25 nm pore in 25 nm membrane (100 mV).

A dilution of 1:1000 of whole blood was initially tested, resulting in clogging of the pore after 14 minutes. To resurrect the pore, the dilution was perfused and the pore enlarged using controlled dielectric conditioning, following techniques established in the literature (Beamish, Eric, Harold Kwok, Vincent Tabard-Cossa, and Michel Godin. "Precise Control of the Size and Noise of Solid-State Nanopores Using High Electric Fields." *Nanotechnology* 23, no. 40 (Sep. 14, 2012): 405301-8). Observe that if a small pore were required to detect short amplicons (without payloads), then such clogging events that necessitate pore enlargement would terminate the test and produce no result. Since our payload-attachment method results in amplicon detection even in large pores, clogging events (which can occur frequently, particularly with "messy" samples) that require pore enlargement do not result in a failed tests; instead, the larger pore can tolerate even more background (it is harder to clog a larger pore) and the test result can still be obtained.

FIG. 18 shows the event plot of max $\delta G$ vs. duration of individual molecules passing through the pore. The recorded epochs include: buffer only (12 events, 30 min); Whole Blood (WB) 1:1000 (154 events, 14 min)—not plotted; WB 1:20000 (157 events, 16 min)—plotted (cyan); and DNA (0.5 nM SRY no biotin, in 1:20000 blood dilution) (293 events over 23 minutes). The SRY without payload had a duration and amplitude distribution that is tighter that for the WB alone. For example, WB sets have 20% events longer than 0.072 ms while SRY alone has only 8% (more faster events). Following SRY, SRY-1MS 0.5 nM in 1:20000 WB was tested and produced a significant increase in the number of events: 1093 events over 26 min. This was followed by SRY-2MS 0.5 nM in 1:20000 WB, which produced 1297 events in 42 min (in all cases, 1:100 PCR reaction mixture was also present). As in prior examples, we can apply the mathematical framework presented to achieve 99% confidence of detection for both of the payload-bound amplicons, as detailed next.

Visually, the event plot in FIG. 18 suggests that the payload-bound events produce a higher percentage of deeper events, particularly for the longer events. From this, we can choose a criterion based on event depth and with a minimum duration. Specifically, consider the criterion of tagging an event as type 2 if max $\delta G > 3$ nS and duration >24 us. The 1:20000 WB+1:100 PCR background false-positive events can be used to compute q1=0.096 (9.6%). With this criterion, for SRY-1MS as the type 2 molecule, the result is $Q(p) - Q_{sd}(p) = 0.184 > 0.096$, which means we can say that SRY-1MS molecules are present with 99% confidence. For SRY-2MS as the type 2 molecule, the result is more pronounced since these molecules with 2 payload produce a larger number of deeper events. Specifically, $Q(p) - Q_{sd}(P) = 0.348 > 0.096$, which means we can say that SRY-2MS molecules are present with 99% confidence. As before, the SRY event population without a payload does not satisfy the criteria in equation (1) in the presence of background (since $Q(p) = 0.024$), and so we cannot say with 99% confidence the SRY molecules are present above background.

A plot of $Q(p) \pm Q_{sd}(p)$ as a function of recording time is shown for each reagent type in the presence of 1:20000 WB+1:100 PCR background in FIG. 19. The trends are also compared to the false-positive threshold established from the background false-positive events. Both the SRY-1MS and SRY-2MS are detected with 99% confidence within the first 90 seconds of recording.

Example 8: SMCY Gene Detection in Presence of Non-Target DNA Background

Figure 21:
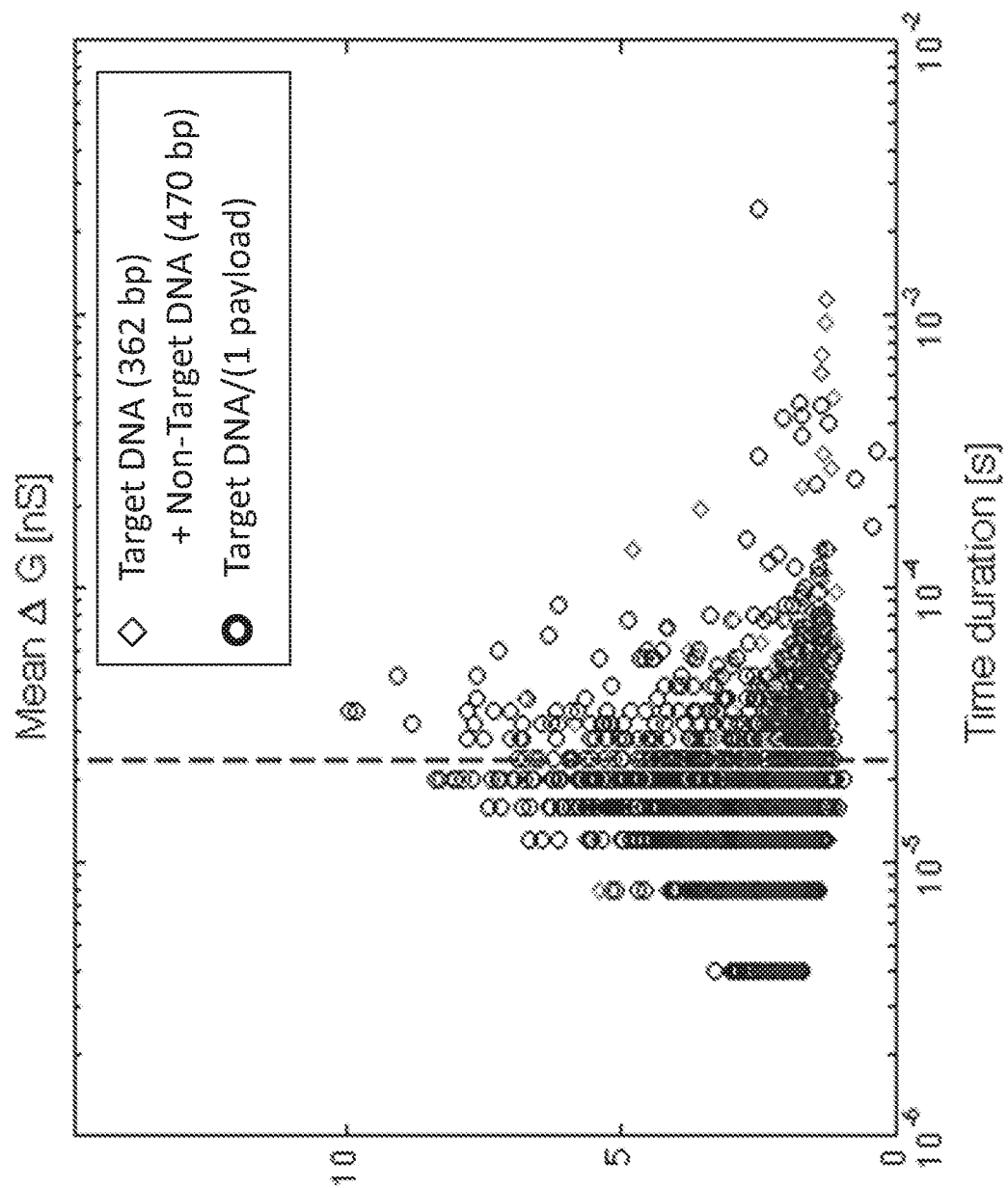
FIG. 21 compares the nanopore current event populations for the combination of 362 bp target DNA and 470 bp non-target DNA (no payloads), with 362 bp target DNA-[1 biotin]-[1 monostreptavidin].
Figure 22:
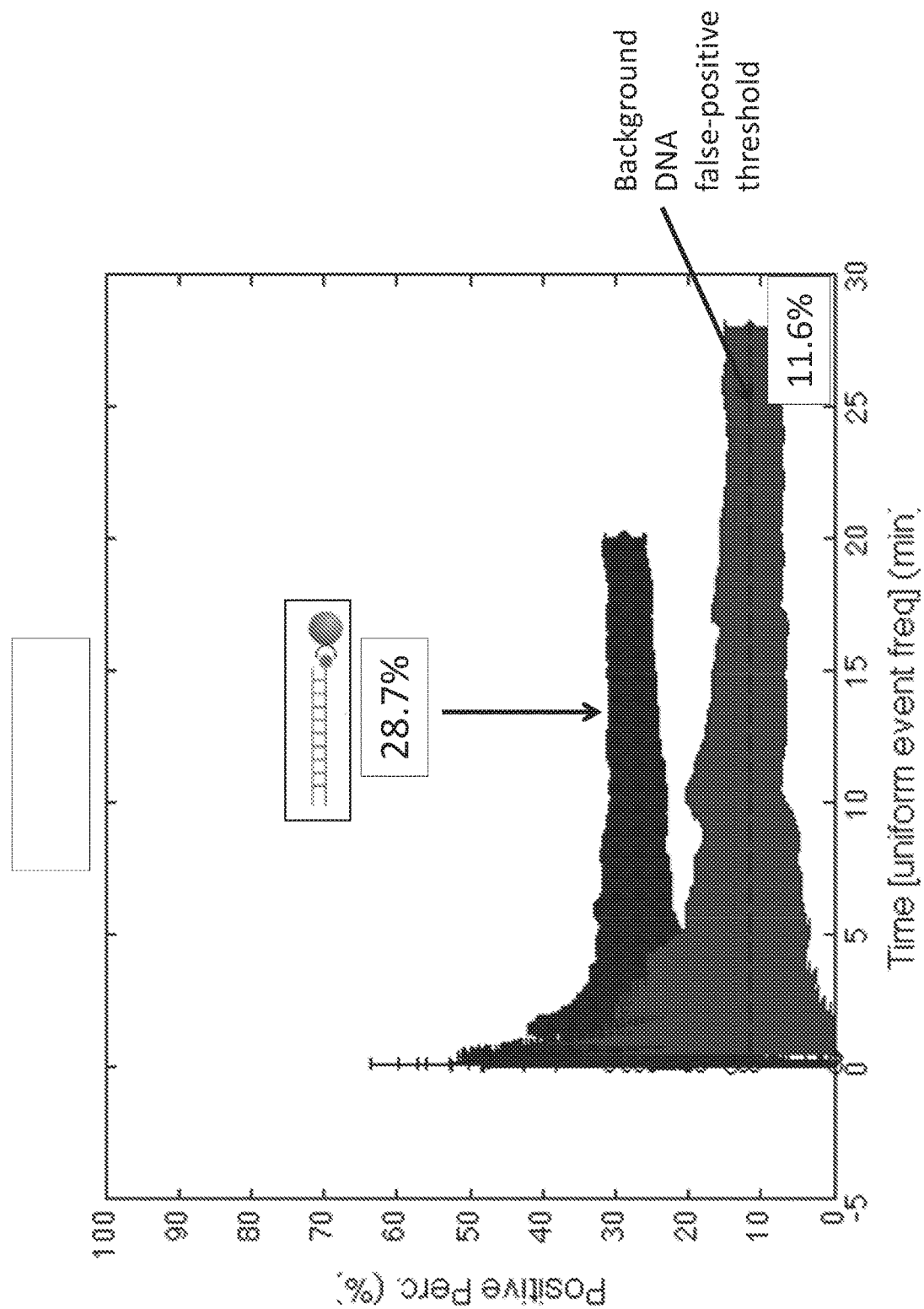
FIG. 22 compares the Positive Percentage detection criteria for 362 bp target DNA-[1 biotin]-[1 monostreptavidin] against the false-positive threshold established from background DNA events (470 bp non-target DNA without payload attached).

FIGS. 21 and 22 show that SMCY-1MS can be detected with 99% confidence in the presence of non-target DNA in abundance as a mock from of background. By contrast, SMCY alone cannot be discriminated from this form of background. These results were obtained using a 21 nm pore in 15 nm membrane (100 mV).

After gel proofing the payload-attached SMCY amplicons (FIG. 20), the following reagents were tested sequentially on the same nanopore. As a mock form of background, we tested SMCY (362 bp) in the presence of an equal concentration of SRY (470 bp) at 0.5 nM total (0.25 nM each). SMCY alone (not shown) could not be discriminated from SRY alone. In particular, the shorter SMCY amplicon had an event rate comparable to electrical background alone, whereas SRY had an event rate about 5× that of electrical noise background events. Thus, the majority of the 560 events recorded over 28 minutes in the SRY+SMCY are likely attributable to SRY, though there is no way to distinguish which events are attributable to either amplicon. To detect the presence of SMCY among this form of background, a biotinylated primer was used at one end and MS attached. At 0.5 nM SMCY-1MS, 1879 events were recorded over 20 minutes.

FIG. 21 shows the event plot of mean $\delta G$ vs. duration of individual molecules passing through the pore. Visually, the event plot suggests that the payload-bound events produce a higher percentage of deeper events. From this, we can choose a criterion of tagging an event as type 2 if max $\delta G > 4$ nS. The SRY+SMCY background false-positive events can be used to compute q1=0.116 (11.6%). With this criterion, for SRY-1MS as the type 2 molecule, the result is $Q(p) - Q_{sd}(p) = 0.287 - 0.026 = 0.26 > 0.116$, which means we can say that SRY-1MS molecules are present with 99% confidence. As before, the SRY event population without a payload does not satisfy the criteria in equation (1) in the presence of background (not shown), and so we cannot say with 99% confidence the SMCY molecules are present above background.

A plot of $Q(p) \pm Q_{sd}(p)$ as a function of recording time is shown for SMCY-1MS compared to non-target DNA (primarily SRY) background in FIG. 22. The SRY-1MS is detected with 99% confidence within the first 2 minutes of recording.

Example 9: Quantitation of Amplicon Concentration

Figure 23:
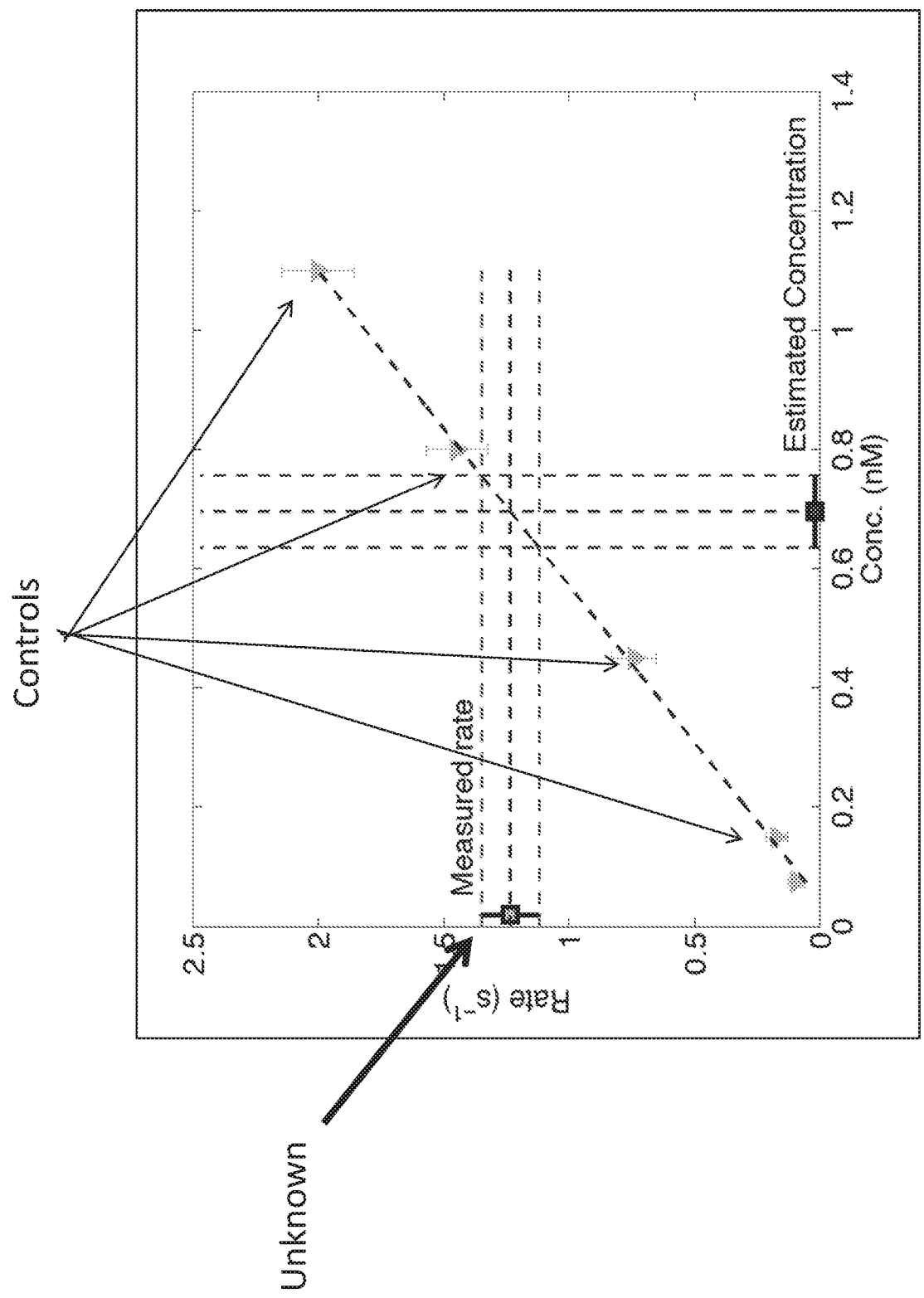
FIG. 23 depicts establishing a linear capture rate vs. concentration trend using controls, and subsequently estimating the unknown concentration of a target polynucleotide by mapping the measured capture rate to the linear trend.

FIG. 23 shows that capture rate is liner with concentration, and that an unknown concentration can be estimated, by using controls to establish the linear trend and mapping a measured rate to the line to estimate concentration. This means using controls that match the capture rate kinetics of the unknown (i.e., use same amplicon length, and with same payload(s) where used). Although there is differences in capture rates between pore sizes, by running the controls prior to the unknown on the same pore, this source of uncertainty is removed.

The data in FIG. 23 was established with a 1074 bp amplicon without a payload, using a 24 nm pore in a 15 nm membrane. The capture rate for each known and unknown concentration is determined by fitting the time-to-capture distribution as an exponential distribution (this is well known in the art of nanopore science, e.g., in Wang, Hongyun, Nicholas Hurt, and William B Dunbar. "Measuring and Modeling the Kinetics of Individual DNA-DNA Polymerase Complexes on a Nanopore." *ACS Nano* 7, no. 5 (May 28, 2013): 3876-86).

The controls were generated using end point PCR was used to create a stock of 1074 bp amplicon. It was purified over silica and quantitated using spectrophotometry. To generate each control, the stock solution was diluted into recording buffer and again measured prior to recording experiments. Standard concentrations used ranged from 0.075 nM to 1.1 nM (0.075 nM, 0.15 nM, 0.8 nM, 1.1 nM). Unknown sample was generated by performing 20 PCR cycles using primers to generate a 1074 amplicon from 100 pg of starting material that was 5600 bp in length. After cycling, the reaction was diluted 1:50 in recording buffer and nanopore experiment performed. The method of fitting to the controls and estimating the unknown while assigning uncertainty to the estimate are presented in the section "Estimating the concentration from measured capture rates." For the estimate in the example, 0.7 nM at 50× dilution corresponds to 35 nM, which is close to the 51 nM value estimated from a spec measurement for the sample prior to dilution.

Example 10: Performance of mnoPCR

Figure 24:
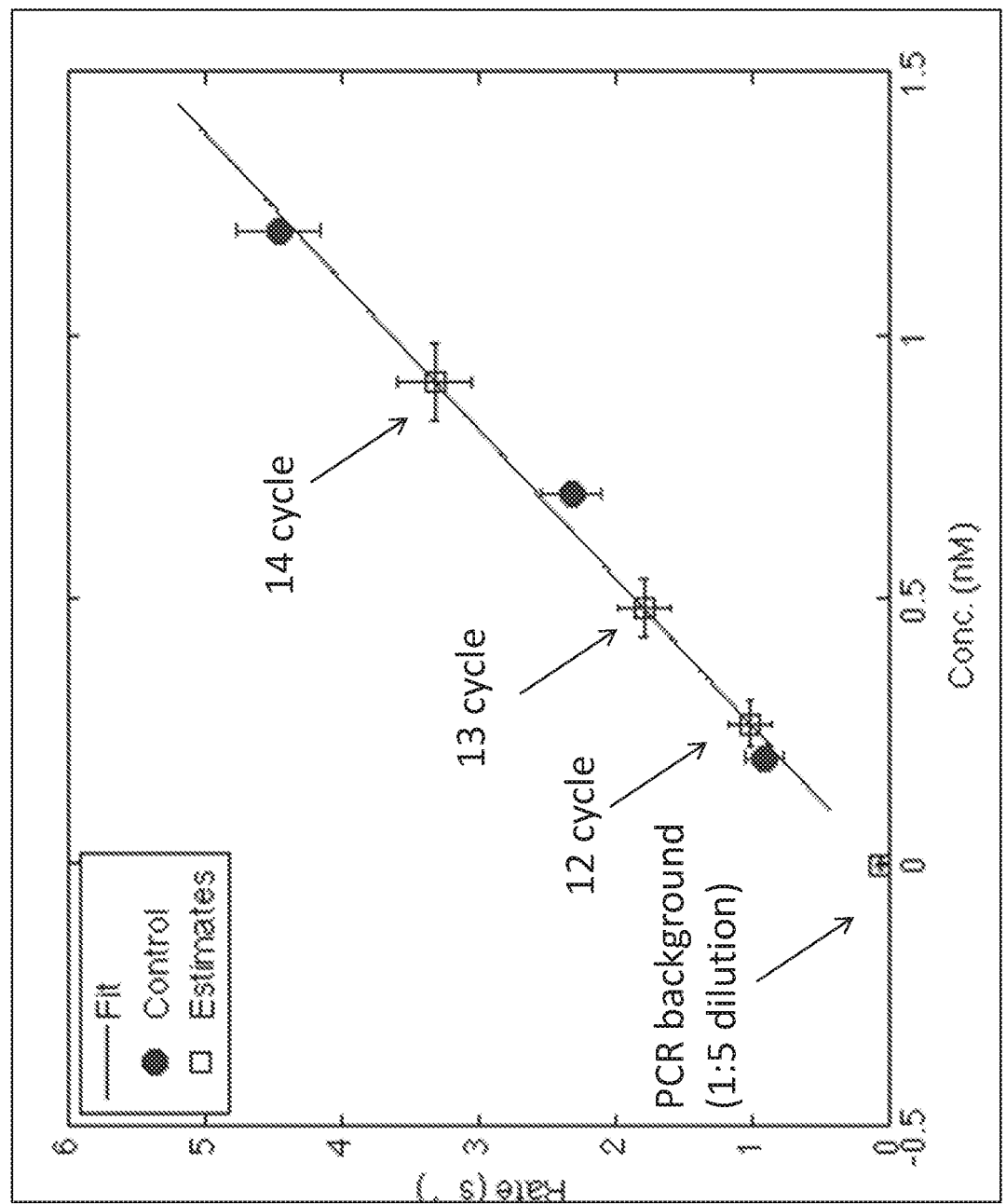
FIG. 24 depicts concentration mapping of 12, 13 and 14 cycle amplicons generated from a PCR reaction to a capture rate vs. concentration trend.
Figure 25:
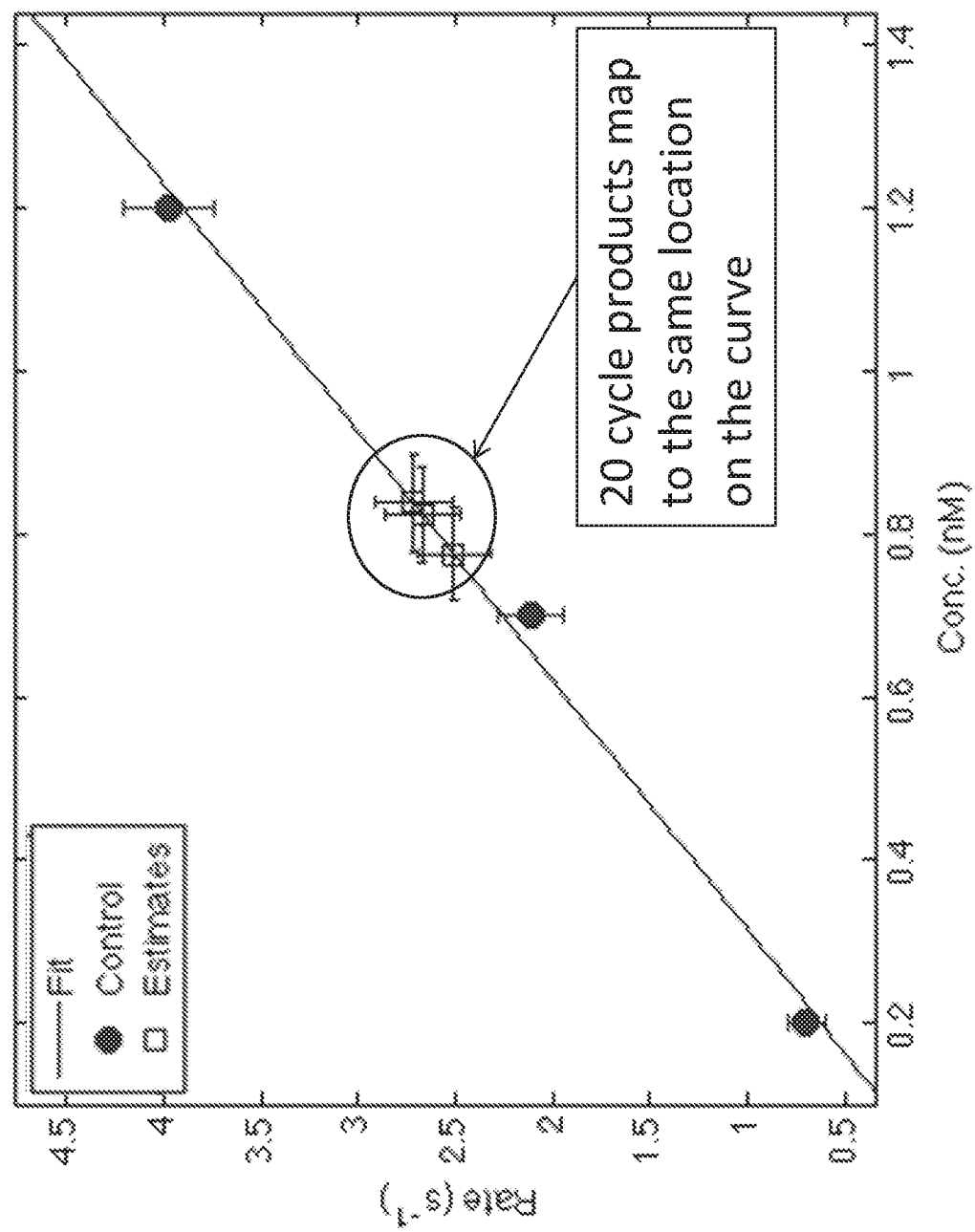
FIG. 25 depicts repeatability of concentration mapping different sets of 20 cycle amplicons generated from separate PCR reactions to a capture rate vs. concentration trend.

FIGS. 24 and 25 present the efficacy of our Integer (m) nanopore (n) observable (o) PCR (mnoPCR) method. For both data sets, the capture rate of three standards of known concentration were first measured using the nanopore to establish a curve to which unknown sample could be mapped. In FIG. 24, a sample of unknown concentration was run after PCR cycle 12, 13, and 14 and the corresponding concentrations estimated. In FIG. 25, accuracy of measurement of unknown samples were then assessed by comparing the capture rate performed of three separate PCR reactions using a common starting material amount and cycle number.

FIG. 24 shows a standard curve from 0.2, 0.7, and 1.2 nM standards and unknowns cycle 12, 13, and 14 mapped to the curve with error bars indicating 99% confidence in the measure (+/−0.46 nM). Recordings were taken in 1 M LiCl, 10 mM Tris, 1 mM EDTA, pH 7.5, at 100 mV and refiltered at 10 kHz. The pore size was 22-25 nm and membrane thickness was 30 nm. The resulting concentrations of unknowns were 1.32 nM, 2.42 nM and 4.56 nM for 12, 13, and 14 cycles, respectively. Consistent with previous examples, background events were <1% of total recorded events. Event plots (not shown) for standards and unknowns showed tight, overlapped grouping, as expected as all of the recorded amplicons are the same length. The plot in FIG. 24 shows the standards (red dots) and unknowns (cycle 12, 13, and 14) in blue, matched to the standard curve. Based on the linearity of the line and error in the measurement of each standard, the reported concentration are 99% accurate within 5%

Measuring after each cycle (or any combination of cycles) as the reaction proceeds allows us to determine at which cycle amplicon is detectable. Additional information can be obtained when measuring amplicon as a reaction precedes, e.g. when reaction is in log phase, the actual efficiency of the PCR reaction (i.e., since the theoretical doubling is often not precisely achieved), end point detection, and accurate comparisons between two or more samples of varying target sequence number. Here, log phase starts at cycle 13 and efficiency per reaction is 1.8× (and not the theoretical 2.0). Detection started at cycle 10.

These data produced a 5% maximum error in estimated concentrations, which inturn suggests that discrimination of 1.1 fold differences in starting material should be possible. This example shows an accurate comparison can be made between two or more samples that may vary in starting template concentration, much like qPCR, but more accurately since the nanopore counts single molecules as opposed to fluorescence from an aggregate collection of molecules.

FIG. 25 presents results of assessing quantitation precision. Specifically, three independent PCR reactions were conducted to generate material, using the same log phase cycle number (20 cycles) and same starting material amount. The concentration estimates were very conserved, demonstrating precision. The results include the estimates: 20 cycle A=54.3 nM; 20 cycle B=57.4 nM; 20 cycle C=58.1 nM. The assay precision=4% (spread/mean). Moreover, precision performance of 1-5% was observed across repeated experiments when cycle number is varied.

Example 11: Inference of Starting Material with mnoPCR

Figure 26:
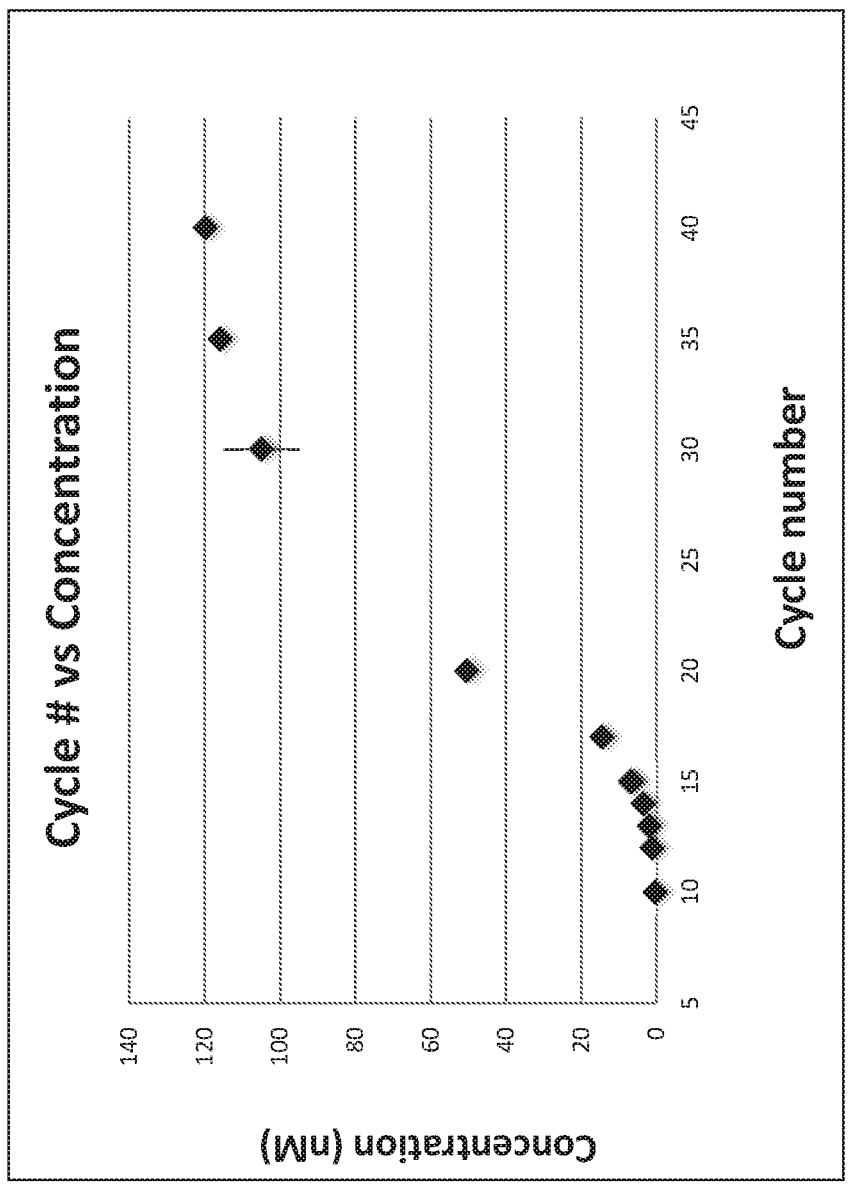
FIG. 26 depicts a sigmoidal trend of estimated concentrations versus PCR cycles 10, 12, 13, 14, 15, 17, 20, 30, 35, 40.

The aggregated data in this example demonstrates a component in a workflow for calculating the starting number of molecules in a sample prior to amplification. Using controls, the mnoPCR method can identify the reaction efficiency and identify when the reaction enters log phase. FIG. 26 shows the sigmoidal curve after measuring a reaction after cycle 10, 12, 13, 14, 15, 17, 20, 30, 35, 40. Specifically, PCR is performed and sample is taken after cycle 10, 12, 13, 14, 15, 17, 20, 30, 35, and 40. Each cycle is independently run in the nanopore. As a control, this can be used to establish the capture rate vs. concentration linear trend; as an unknown, the rate is fitted to the line to determine the amount of product generated after the indicated cycle by the concentration estimation method. Note that only two controls (a high and a low concentration) need be tested to establish the capture rate vs. concentration trend prior to testing a sequence of PCR cycle products. For this control data set, the reaction entered log phase after cycle 15, displayed a sub-optimal doubling of 1.7×, and reached endpoint after cycle 35. In practice, this can serve as a control curve, to be used with the quantitated reaction efficiency performance and the unknown curve to extrapolate the amount of starting material.

Note that with an array of pores sharing a common chamber where amplicons are added (or generated), a lower cycle number can be detected earlier with larger dilutions tolerated, to provide better resolution and spread in the lower concentration end of the curve. This in turn would improve quantitation of unknowns and lower inference errors.

Example 12: Exploring Minimal Dilutions of PCR Reaction Mixture

Figure 27:
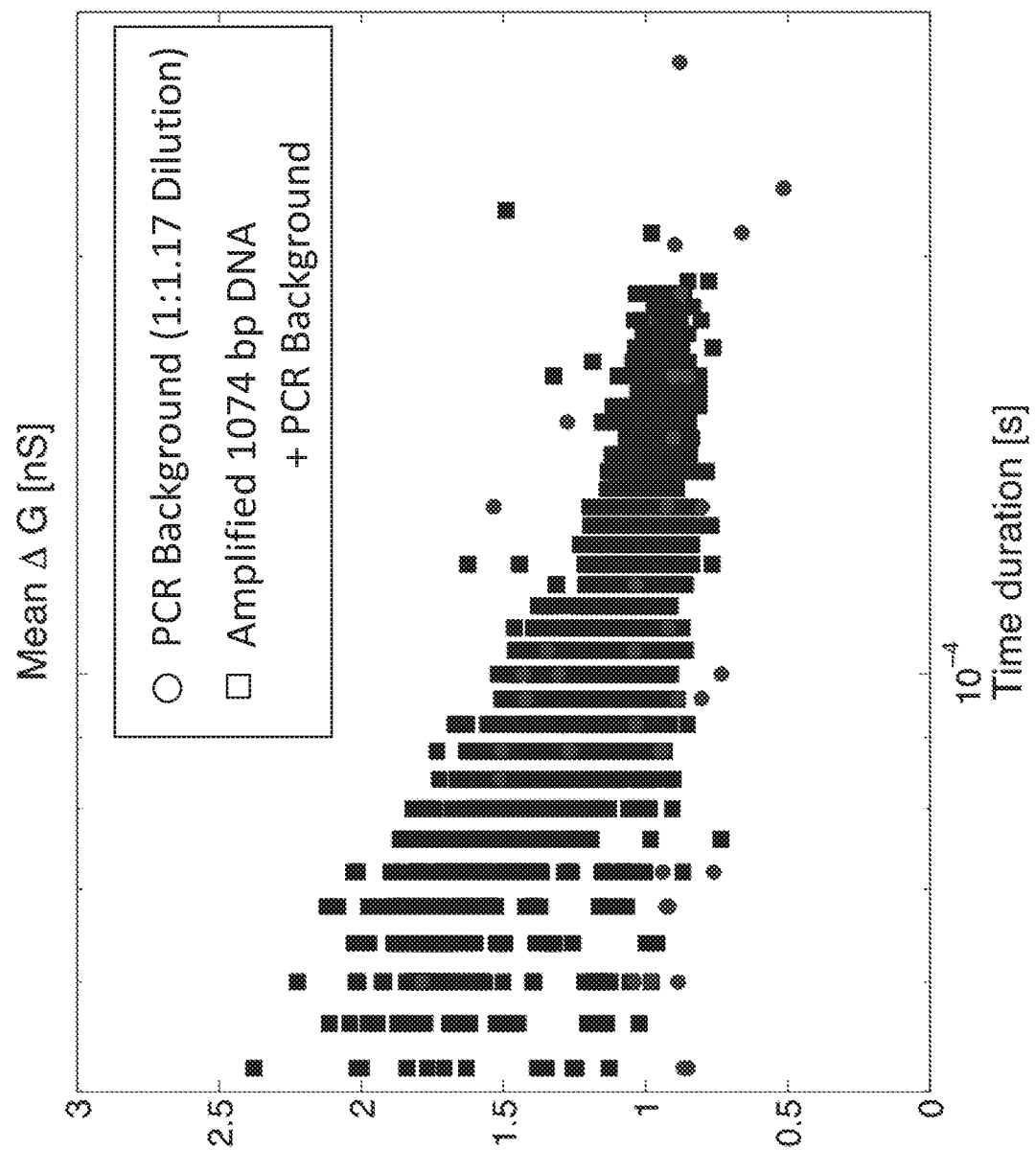
FIG. 27 compares the nanopore current event populations for PCR background at a minimal (1:1.17) dilution versus amplified 1074 bp DNA in the same PCR background.
Figure 28:
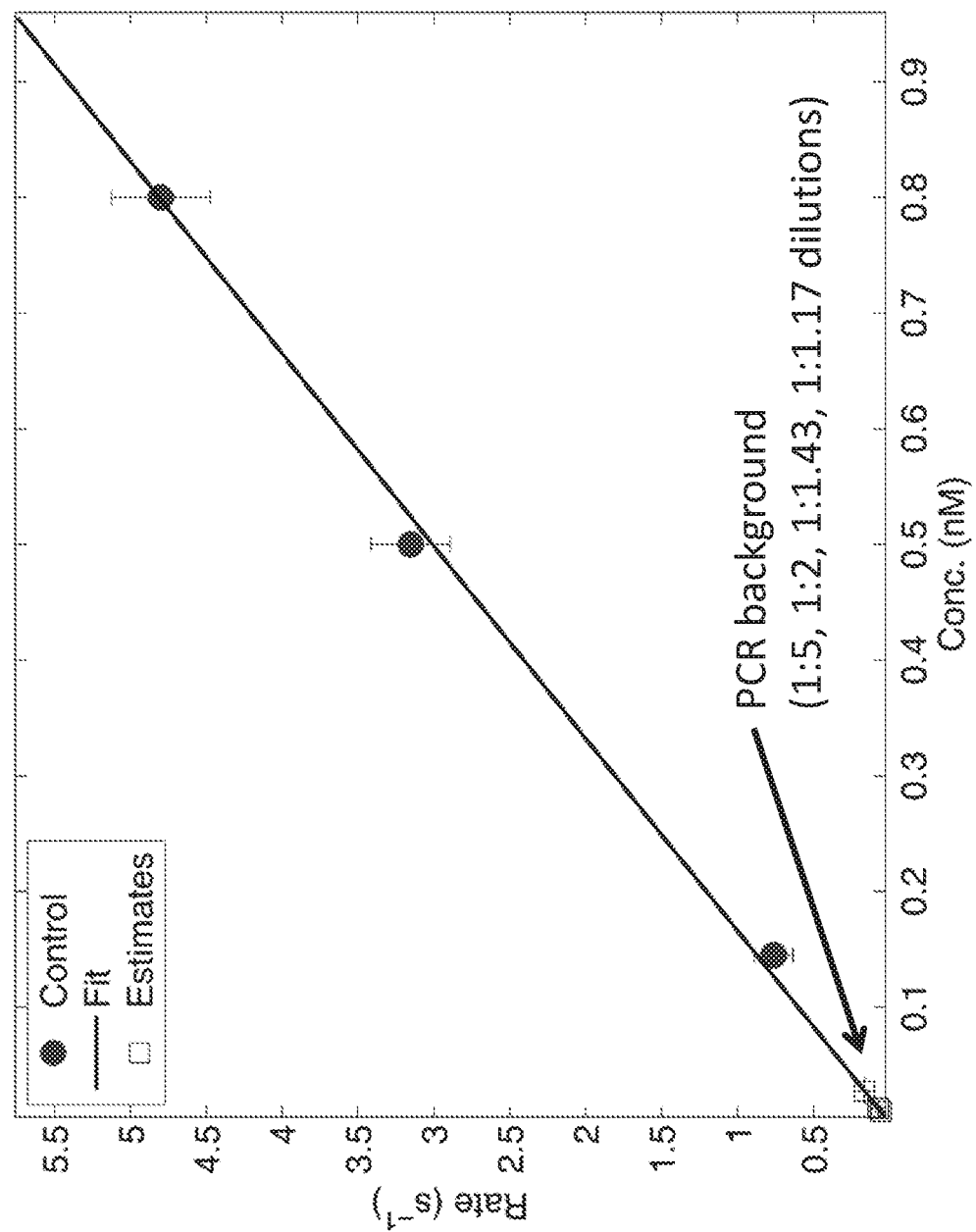
FIG. 28 depicts concentration mapping of negative controls (10 cycles of PCR absent starting template) to a capture rate vs. concentration trend, at dilutions 1:5, 1:2, 1:1.43 and 1:1.17.

FIGS. 27 and 28 explore how little dilution is required while still preserving the fidelity of the mnoPCR method. FIG. 27 shows the event plot of mean δG vs. duration of individual molecules passing through the pore. The plots shows events for PCR reaction mixture (red) after 15 cycles with a negative control (water) at 1:1.17 dilution (85.7% PCR reaction mixture), followed by the same mixture but with a 1074 bp amplicon generated (positive control, 15 cycles) showing a large increase in events (black). While the 1074 bp DNA at 0.5 nM produced 1856 events over 10 minutes, the 85.7% PCR product produced only 39 events over 10 minutes, using a 25 nm pore in a 25 nm membrane. All negative control dilutions considered performed comparably in event rate and spread: 1:5 dilution (20%), 1:2 dilution (50%), 1:1.43 dilution (70%), 1:1.17 dilution (85.7%). FIG. 28 shows that when the negative control PCR product is minimally diluted (1:1.17) it produces enough appreciable events to trigger a less accurate concentration estimation. This effect is minimized when diluting the sample by >30%.

The invention claimed is:

1. A method for detecting the presence or absence of a target polynucleotide sequence of a target polynucleotide in a sample, comprising:
contacting the sample with a set of primers, wherein at least one of said primers is hybridizable to the target polynucleotide comprising said target polynucleotide sequence, and is modified to comprise a conjugation site capable of specifically binding to a payload molecule;
performing an amplification reaction on said sample, wherein said sample comprises said primer set and reagents for amplification, such that an amplicon generated by said amplification reaction comprises said conjugation site;
binding said payload molecule to said conjugation site;
loading said sample into a nanopore device comprising a nanopore, wherein said sample loaded into said device comprises non-target polynucleotides and amplification reaction reagents, wherein said nanopore is at least 5 nm in diameter and that separates an interior space of the nanopore device into two volumes, wherein the nanopore device comprises a sensor having an electrode pair to apply a voltage differential between the two volumes to allow the sensor to measure current flow through the nanopore separating the two volumes; and
detecting current shift events, when present, caused by payload-bound target polynucleotides and unbound background molecules passing through the nanopore;
calculating for each event a conductance shift depth ($\delta G = \delta I/V$) and duration, wherein said conductance shift depth is computed as a mean or maximum current shift divided by voltage;
distinguishing events caused by payload-bound target polynucleotides and unbound background molecules based on the calculated conductance shift depth and duration of each event; and
detecting the presence or absence of said target polynucleotide sequence in said sample based on the presence or absence of events corresponding to payload-bound target polynucleotides.

2. The method of claim 1, wherein said sample is loaded into said device before said amplification.

3. The method of claim 1, wherein said sample is loaded into said device after said amplification.

4. The method of claim 1, wherein said payload molecule is bound to said conjugation site of said amplicon after said amplification.

5. The method of claim 1, wherein said payload molecule is bound to said conjugation site of said primer before said amplification.

6. The method of claim 1, wherein said sample does not undergo a purification step between said amplification and said detection in said nanopore.

7. The method of claim 1, wherein said sample is loaded into said nanopore device at a dilution of at least 1:20000, 1:10000, 1:5000, 1:2000, 1:1000, 1:500, 1:200, 1:100, 1:50, 1:20, 1:10, 1:5, 1:2, 1:1.5, 1:1.2, 1:1.1 or 1:1.05.

8. The method of claim 1, wherein said sample is loaded into said nanopore device without dilution.

9. The method of claim 1, wherein said nanopore is at least 10 nm, 20 nm, 30 nm, 40 nm, or 50 nm in diameter.

10. The method of claim 1, wherein said amplification reaction is selected from the group consisting of: polymerase chain reaction (PCR), reverse transcription PCR, ligation mediated PCR, loop mediated amplification (LAMP), isothermal amplification, strand displacement amplification (SDA), multiple displacement amplification, strand displacement amplification, helicase dependent amplification, nicking enzyme amplification reaction, or recombinant polymerase amplification.

11. The method of claim 1, wherein said amplification reaction is performed in the interior space of the device.

12. The method of claim 1, wherein the target polynucleotide comprises double-stranded deoxyribonucleic acid (dsDNA), single-stranded DNA (ssDNA), peptide nucleic acid (PNA), single-stranded ribonucleic acid (ssRNA), DNA/RNA hybrid, or double-stranded ribonucleic acid (dsRNA).

13. The method of claim 1, wherein the target polynucleotide is a naturally-occurring polynucleotide.

14. The method of claim 1, wherein the target polynucleotide is an artificially synthesized polynucleotide.

15. The method of claim 14, wherein the conjugation site is located at or near the 5' end of the said amplicon.

16. The method of claim 1, wherein the target polynucleotide is a recombinant polynucleotide.

17. The method of claim 1, wherein the payload molecule is selected from the group consisting of: a dendrimer, double stranded DNA, single stranded DNA, a DNA aptamer, a fluorophore, a protein, an antibody, a polypeptide, a nanobead, a nanorod, a nanotube, nanoparticle, fullerene, a PEG molecule, a liposome, or a cholesterol-DNA hybrid.

18. The method of claim 1, wherein said payload molecule comprises an electrical charge.

19. The method of claim 18, wherein said charged payload molecule is selected form the group consisting of: a peptide, an amino acid, a charged nanoparticle, a synthetic molecule, a nucleotide, a polynucleotide, a metal, or an ion.

20. The method of claim 18, wherein the sensitivity or specificity of detection of the presence of absence of the target polynucleotide is increased when said target polynucleotide is bound to said charged payload molecule as compared to unbound target polynucleotide.

21. The method of claim 1, wherein the sensitivity or specificity of detection of the presence or absence of the target polynucleotide is increased when said target polynucleotide is bound to said payload molecule as compared to unbound target polynucleotide.

22. The method of claim 1, wherein the conjugation site and the payload molecule are bound via a covalent bond.

23. The method of claim 22, wherein said covalent bond is formed by click chemistry.

24. The method of claim 23, wherein said click chemistry is copper catalyzed.

25. The method of claim 23, wherein said click chemistry is copper free.

26. The method of claim 1, wherein the conjugation site and the payload molecule are bound via a non-covalent bond.

27. The method of claim 26, wherein said non-covalent bond is a hydrogen bond, an ionic bond, a van der Waals interaction, a hydrophobic interaction, a polar bond, a cation-pi interaction, a planar stacking interaction, or a metallic bond.

28. The method of claim 1, wherein the conjugation site is located at the 3' or the 5' end of the said primer.

29. The method of claim 1, wherein the conjugation site comprises a chemical group, a reactive group, a small molecule, or a peptide.

30. The method of claim 29, wherein the small molecule comprises biotin.

31. The method of claim 29, wherein the reactive group comprises dibenzocyclooctyl (DBCO) or azide.

32. The method of claim 1, wherein two or more payload molecules are bound to said amplicon.

33. The method of claim 1, wherein said device comprises at least two nanopores in series, and wherein said amplicon bound to said payload molecule is simultaneously in said at least two nanopores during translocation.

34. A method for detecting the presence or absence of a target polynucleotide sequence suspected to be present in a sample, comprising:
  contacting the sample with a set of primers, wherein at least one of said primers is hybridizable to the target polynucleotide comprising said target polynucleotide sequence, and is bound to a payload molecule;
  performing an amplification reaction on said sample, wherein said sample comprises said primer set and reagents for amplification, such that an amplicon comprising said target polynucleotide sequence generated by said amplification reaction will be bound to said payload molecule;
  loading said sample into a nanopore device comprising a nanopore, wherein said sample loaded into said device comprises non-target polynucleotides and amplification reaction reagents, wherein said nanopore is at least 5 nm and separates an interior space of the device into two volumes, wherein the nanopore device comprises a sensor having an electrode pair to apply a voltage differential between the two volumes to allow the sensor to measure current flow through the nanopore separating the two volumes; and
  detecting current shift events, when present, caused by payload-bound target polynucleotides and unbound background molecules passing through the nanopore;
  calculating for each event a conductance shift depth ($\delta G = \delta I/V$) and duration, wherein said conductance shift depth is computed as a mean or maximum current shift divided by voltage;
  distinguishing events caused by payload-bound target polynucleotides and unbound background molecules based on the calculated conductance shift depth and duration of each event; and
  detecting the presence or absence of said target polynucleotide sequence in said sample based on the presence or absence of events corresponding to payload-bound target polynucleotides.

35. The method of claim 34, wherein said sample is loaded into said device before said amplification.

36. The method of claim 34, wherein said sample is loaded into said device after said amplification.

37. The method of claim 34, wherein said sample does not undergo a purification step between said amplification and said detection in said nanopore.

38. The method of claim 34, wherein said sample is loaded into said nanopore device ata dilution of 1:10000, 1:1000, 1:500, 1:200, 1:100, 1:50, 1:20, 1:10, 1:5, 1:2, 1:1.5, 1:1.2, 1:1.1 or 1:1.05.

39. The method of claim 34, wherein said sample is loaded into said nanopore device without dilution.

40. The method of claim 34, wherein said nanopore is at least 10 nm, 20 nm, 30 nm, 40 nm, or 50 nm in diameter.

41. The method of claim 34, wherein said amplification reaction is selected from the group consisting of: polymerase chain reaction (PCR), reverse transcription PCR, ligation mediated PCR, loop mediated amplification (LAMP), isothermal amplification, strand displacement amplification (SDA), multiple displacement amplification, strand displacement amplification, helicase dependent amplification, nicking enzyme amplification reaction, or recombinant polymerase amplification.

42. The method of claim 34, wherein said amplification reaction is performed in the interior space of the device.

43. The method of claim 34, wherein the target polynucleotide comprises double-stranded deoxyribonucleic acid (dsDNA), single-stranded DNA (ssDNA), peptide nucleic acid (PNA), single-stranded ribonucleic acid (ssRNA), DNA/RNA hybrid, or double-stranded ribonucleic acid (dsRNA).

44. The method of claim 34, wherein the target polynucleotide is a naturally-occurring polynucleotide.

45. The method of claim 34, wherein the target polynucleotide is an artificially synthesized polynucleotide.

46. The method of claim 34, wherein the target polynucleotide is a recombinant polynucleotide.

47. The method of claim 34, wherein the payload molecule is selected from the group consisting of: a dendrimer, double stranded DNA, single stranded DNA, a DNA aptamer, a fluorophore, a protein, an antibody, a polypeptide, a nanobead, a nanorod, a nanotube, nanoparticle, fullerene, a PEG molecule, a liposome, or a cholesterol-DNA hybrid.

48. The method of claim 34, wherein said payload molecule comprises an ionic charge.

49. The method of claim 48, wherein said charged payload molecule is selected form the group consisting of: a peptide, an amino acid, a charged nanoparticle, a synthetic molecule, a nucleotide, a polynucleotide, a metal, or an ion.

50. The method of claim 48, wherein the sensitivity or specificity of detection of the presence or absence of the target polynucleotide is increased when said target polynucleotide is bound to said charged payload molecule as compared to unbound target polynucleotide.

51. The method of claim 34, wherein the sensitivity or specificity of detection of the presence of absence of the target polynucleotide is increased when said target polynucleotide is bound to said payload molecule as compared to unbound target polynucleotide.

52. The method of claim 34, wherein the primer and the payload molecule are bound via a covalent bond.

53. The method of claim 34, wherein the primer and the payload molecule are bound via a non-covalent bond.

54. The method of claim 34, wherein the payload molecule is bound at the 3' or the 5' end of the said primer.

55. The method of claim 34, wherein two or more payload molecules are bound to said primer.

56. The method of claim 34, wherein the amplicon and the payload molecule are bound via a covalent bond.

57. The method of claim 34, wherein the amplicon and the payload molecule are bound via a non-covalent bond.

58. The method of claim 34, wherein two or more payload molecules are bound to said amplicon.

59. The method of claim 34, wherein said device comprises at least two nanopores in series, and wherein said amplicon bound to said payload molecule is simultaneously in said at least two nanopores during translocation.

\* \* \* \* \*

UNITED STATES PATENT AND TRADEMARK OFFICE
CERTIFICATE OF CORRECTION

| | | |
|---|---|---|
| PATENT NO. | : 11,098,348 B2 | Page 1 of 1 |
| APPLICATION NO. | : 15/547434 | |
| DATED | : August 24, 2021 | |
| INVENTOR(S) | : Morin et al. | |

It is certified that error appears in the above-identified patent and that said Letters Patent is hereby corrected as shown below:

On the Title Page

Item (58), in Column 2, under "Field of Classification Search", Line 3, delete "C12Q 33/48721" and insert -- G01N 33/48721 --

In the Claims

In Column 39, in Claim 19, Line 39, delete "form" and insert -- from --

In Column 40, in Claim 38, Line 63, delete "ata" and insert -- at a --

In Column 42, in Claim 49, Line 2, delete "form" and insert -- from --

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 1
gaatattccc gctctccgga                                                      20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctggtgctc cattcttgag                                                      20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cctccagacc tggacagaat                                                      20

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtggtctgt ggaaggtgtc a                                                    21
```